US011969325B2

(12) United States Patent
Ashraf et al.

(10) Patent No.: US 11,969,325 B2
(45) Date of Patent: Apr. 30, 2024

(54) ABSORBENT ARTICLE WITH FUNCTION-FORMED TOPSHEET, AND METHOD FOR MANUFACTURING

(71) Applicant: The Procter & Gamble Company, Cincinnati, OH (US)

(72) Inventors: Arman Ashraf, Mason, OH (US); Kelyn Anne Arora, Cincinnati, OH (US); Misael Omar Aviles, Cincinnati, OH (US); Lennie CruzMurphy, Cincinnati, OH (US); Antonius Lambertus DeBeer, Loveland, OH (US); Adrien Grenier, Frankfurt am Main (DE); John Lee Hammons, Hamilton, OH (US); Emma Lynn Sartini, Covington, KY (US); Paul Thomas Weisman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 966 days.

(21) Appl. No.: 16/445,986

(22) Filed: Jun. 19, 2019

(65) Prior Publication Data

US 2019/0380887 A1 Dec. 19, 2019

Related U.S. Application Data

(63) Continuation-in-part of application No. 15/879,474, filed on Jan. 25, 2018, now Pat. No. 10,655,257.
(Continued)

(51) Int. Cl.
*A61F 13/513* (2006.01)
*A61F 13/15* (2006.01)
(Continued)

(52) U.S. Cl.
CPC .. *A61F 13/51305* (2013.01); *A61F 13/15707* (2013.01); *A61F 13/15764* (2013.01);
(Continued)

(58) Field of Classification Search
CPC .......... A61F 13/51305; A61F 13/15707; A61F 13/15764; A61F 13/47; A61F 13/51108;
(Continued)

(56) References Cited

U.S. PATENT DOCUMENTS 1,065,525 A 6/1913 Henkel
3,113,225 A 12/1963 Claus et al.
(Continued)

FOREIGN PATENT DOCUMENTS

CA 2158790 A1 3/1996
CN 1107738 A 9/1995
(Continued)

OTHER PUBLICATIONS

PCT International Search Report and Written Opinion, dated Sep. 23, 2016 (6 pages).
(Continued)

*Primary Examiner* — Jessica Arble
(74) *Attorney, Agent, or Firm* — Christian M. Best; William E. Gallagher

(57) ABSTRACT

An absorbent article is disclosed. The article includes a topsheet formed of a section of formed nonwoven web material having an ordered arrangement of zones, each zone comprising one or more attenuated regions adjacent to one or more built-up regions, wherein the attenuated regions have a first average basis weight and the built-up regions have a second average basis weight, wherein the first average basis weight is less than the second average basis weight, the difference in basis weights corresponding to disposition of the filaments according to the ordered
(Continued)

arrangement. The attenuated region(s) may be included within a configuration of one or more channel portions on the topsheet. Alternatively or in combination, the attenuated region(s) may be included within a hinge portion extending along a wing portion of the topsheet.

20 Claims, 24 Drawing Sheets

Related U.S. Application Data

(60) Provisional application No. 62/687,043, filed on Jun. 19, 2018.

(51) Int. Cl.
*A61F 13/47* (2006.01)
*A61F 13/51* (2006.01)
*A61F 13/511* (2006.01)
*A61F 13/514* (2006.01)
*A61F 13/53* (2006.01)
*A61F 13/84* (2006.01)

(52) U.S. Cl.
CPC ........ *A61F 13/47* (2013.01); *A61F 13/51108* (2013.01); *A61F 13/51113* (2013.01); *A61F 13/51121* (2013.01); *A61F 13/51394* (2013.01); *A61F 13/51456* (2013.01); *A61F 13/53* (2013.01); *A61F 13/8405* (2013.01); *A61F 2013/15406* (2013.01); *A61F 2013/15861* (2013.01); *A61F 2013/51059* (2013.01); *A61F 2013/8497* (2013.01)

(58) Field of Classification Search
CPC .......... A61F 13/51113; A61F 13/51121; A61F 13/51394; A61F 13/51456; A61F 13/53; A61F 13/8405; A61F 2013/15406; A61F 2013/15861; A61F 2013/51059; A61F 2013/8497

See application file for complete search history.

(56) References Cited

U.S. PATENT DOCUMENTS

| | | |
|---|---|---|
| 3,423,266 A | 1/1969 | Davies et al. |
| 3,508,722 A | 4/1970 | Kohl |
| 3,562,041 A | 2/1971 | Robertson |
| 3,575,782 A | 4/1971 | Hansen |
| 3,692,618 A | 9/1972 | Dorschner et al. |
| 3,733,238 A | 5/1973 | Long et al. |
| 3,802,817 A | 4/1974 | Matsuki et al. |
| 3,860,003 A | 1/1975 | Buell |
| 4,100,324 A | 7/1978 | Anderson et al. |
| 4,333,979 A | 6/1982 | Sciaraffa et al. |
| 4,525,905 A | 7/1985 | Bogucki-Land |
| 4,610,678 A | 9/1986 | Weisman et al. |
| 4,673,402 A | 6/1987 | Weisman et al. |
| 4,695,278 A | 9/1987 | Lawson |
| 4,704,115 A | 11/1987 | Buell |
| 4,741,941 A | 5/1988 | Englebert et al. |
| 4,795,454 A | 1/1989 | Dragoo |
| 4,834,735 A | 5/1989 | Alemany et al. |
| 4,854,984 A | 8/1989 | Ball et al. |
| 4,888,231 A | 12/1989 | Angstadt |
| 4,909,803 A | 3/1990 | Aziz et al. |
| 4,940,464 A | 7/1990 | Van Gompel et al. |
| 4,970,104 A | 11/1990 | Radwanski |
| 5,003,676 A | 4/1991 | Mcfalls |
| 5,060,881 A | 10/1991 | Bogucki-Land |
| 5,092,861 A | 3/1992 | Nomura et al. |
| 5,110,403 A | 5/1992 | Ehlert |
| 5,167,897 A | 12/1992 | Weber et al. |
| 5,246,433 A | 9/1993 | Hasse et al. |
| 5,334,289 A | 8/1994 | Trokhan et al. |
| 5,360,420 A | 11/1994 | Cook et al. |
| 5,393,360 A | 2/1995 | Bridges et al. |
| 5,413,849 A | 5/1995 | Austin et al. |
| 5,508,102 A | 4/1996 | Georger et al. |
| 5,514,523 A | 5/1996 | Trokhan et al. |
| 5,562,646 A | 10/1996 | Goldman et al. |
| 5,569,234 A | 10/1996 | Buell et al. |
| 5,575,874 A | 11/1996 | Griesbach, III et al. |
| 5,599,335 A | 2/1997 | Goldman et al. |
| 5,599,420 A | 2/1997 | Yeo et al. |
| 5,628,097 A | 5/1997 | Benson et al. |
| 5,643,588 A | 7/1997 | Roe et al. |
| 5,643,653 A | 7/1997 | Griesbach, III et al. |
| 5,669,894 A | 9/1997 | Goldman et al. |
| 5,674,216 A | 10/1997 | Buell et al. |
| 5,702,551 A | 12/1997 | Huber et al. |
| 5,725,927 A | 3/1998 | Zilg et al. |
| 5,762,641 A | 6/1998 | Bewick-sonntag |
| 5,775,380 A | 7/1998 | Roelstraete et al. |
| 5,858,504 A | 1/1999 | Fitting |
| 5,887,322 A | 3/1999 | Hartzheim et al. |
| 5,895,623 A | 4/1999 | Trokhan et al. |
| 5,897,545 A | 4/1999 | Kline et al. |
| 5,916,661 A | 6/1999 | Benson et al. |
| 5,957,908 A | 9/1999 | Kline et al. |
| 5,964,973 A | 10/1999 | Heath et al. |
| 5,968,025 A | 10/1999 | Roe et al. |
| 6,036,796 A | 3/2000 | Halbert et al. |
| 6,043,168 A | 3/2000 | Colman et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,139,941 A | 10/2000 | Jankevics et al. |
| 6,153,209 A | 11/2000 | Vega et al. |
| 6,248,195 B1 | 6/2001 | Schmitz |
| 6,291,039 B1 | 9/2001 | Combe et al. |
| 6,319,239 B1 | 11/2001 | Daniels et al. |
| 6,319,455 B1 | 11/2001 | Kauschke et al. |
| 6,331,268 B1 | 12/2001 | Kauschke et al. |
| 6,331,345 B1 | 12/2001 | Kauschke et al. |
| 6,361,638 B2 | 3/2002 | Takai et al. |
| 6,383,431 B1 | 5/2002 | Dobrin et al. |
| 6,395,957 B1 | 5/2002 | Chen et al. |
| 6,410,129 B2 | 6/2002 | Zhang et al. |
| 6,426,444 B2 | 7/2002 | Roe et al. |
| 6,436,512 B1 | 8/2002 | Kauschke et al. |
| 6,508,641 B1 | 1/2003 | Kubik |
| 6,545,197 B1 | 4/2003 | Muller et al. |
| 6,554,815 B1 | 4/2003 | Umebayashi |
| 6,586,652 B1 | 7/2003 | Roe et al. |
| 6,617,016 B2 | 9/2003 | Zhang et al. |
| 6,627,787 B1 | 9/2003 | Roe et al. |
| 6,632,504 B1 | 10/2003 | Gillespie et al. |
| 6,645,330 B2 | 11/2003 | Pargass et al. |
| 6,673,418 B1 | 1/2004 | DeOlivera et al. |
| 6,676,054 B2 | 1/2004 | Heaney et al. |
| 6,790,798 B1 | 9/2004 | Suzuki et al. |
| 6,818,802 B2 | 11/2004 | Takai et al. |
| 6,821,301 B2 | 11/2004 | Azuse et al. |
| 6,825,393 B2 | 11/2004 | Roe et al. |
| 6,861,571 B1 | 3/2005 | Roe et al. |
| 7,008,685 B2 | 3/2006 | Groitzsch et al. |
| 7,118,558 B2 | 10/2006 | Wu et al. |
| 7,306,582 B2 | 12/2007 | Adams |
| 7,465,367 B2 | 12/2008 | Day |
| 7,507,463 B2 | 3/2009 | Noda et al. |
| 7,553,535 B2 | 6/2009 | Noda et al. |
| 7,569,039 B2 | 8/2009 | Matsuda et al. |
| 7,582,348 B2 | 9/2009 | Ando et al. |
| 7,642,398 B2 | 1/2010 | Jaerpenberg et al. |
| 7,662,462 B2 | 2/2010 | Noda et al. |
| 7,708,849 B2 | 5/2010 | McCabe |
| 7,777,094 B2 | 8/2010 | Mori et al. |
| 7,861,756 B2 | 1/2011 | Jenquin et al. |
| 7,878,447 B2 | 2/2011 | Hartzheim |

(56) References Cited

U.S. PATENT DOCUMENTS

| | | |
|---|---|---|
| 7,897,240 B2 | 3/2011 | Noda et al. |
| 7,901,393 B2 | 3/2011 | Matsuda et al. |
| 7,905,446 B2 | 3/2011 | Hartzheim |
| 7,954,213 B2 | 6/2011 | Mizutani et al. |
| 7,955,549 B2 | 6/2011 | Noda et al. |
| 8,017,534 B2 | 9/2011 | Harvey et al. |
| 8,093,161 B2 | 1/2012 | Bansal et al. |
| 8,143,177 B2 | 3/2012 | Noda et al. |
| 8,183,431 B2 | 5/2012 | Noda et al. |
| 8,186,296 B2 | 5/2012 | Brown et al. |
| 8,226,625 B2 | 7/2012 | Turner et al. |
| 8,273,941 B2 | 9/2012 | Uematsu et al. |
| 8,304,600 B2 | 11/2012 | Noda et al. |
| 8,308,706 B2 | 11/2012 | Fukae |
| 8,377,554 B2 | 2/2013 | Martin et al. |
| 8,388,594 B2 | 3/2013 | Turner et al. |
| 8,440,043 B1 | 5/2013 | Schneider et al. |
| 8,551,608 B2 | 10/2013 | Kawakami et al. |
| 8,574,209 B2 | 11/2013 | Nishitani et al. |
| 8,585,666 B2 | 11/2013 | Weisman et al. |
| 8,647,319 B2 | 2/2014 | Een et al. |
| 8,729,332 B2 | 5/2014 | Takahashi et al. |
| 8,758,569 B2 | 6/2014 | Aberg et al. |
| 8,778,127 B2 | 7/2014 | Schneider et al. |
| 8,853,108 B2 | 10/2014 | Ahoniemi et al. |
| 8,865,965 B2 | 10/2014 | Sato et al. |
| 8,906,275 B2 | 12/2014 | Davis et al. |
| 9,005,392 B2 | 4/2015 | Schneider et al. |
| 9,039,855 B2 | 5/2015 | Schneider et al. |
| 9,050,213 B2 | 6/2015 | LaVon et al. |
| 9,095,477 B2 | 8/2015 | Yamaguchi et al. |
| 9,156,229 B2 | 10/2015 | Yoda et al. |
| 9,156,648 B2 | 10/2015 | Yamamoto |
| 9,168,182 B2 | 10/2015 | Hargett et al. |
| 9,198,804 B2 | 12/2015 | Nakamura et al. |
| 9,205,005 B2 | 12/2015 | Kikuchi et al. |
| 9,226,861 B2 | 1/2016 | LaVon et al. |
| 9,248,054 B2 | 2/2016 | Brown et al. |
| 9,265,672 B2 | 2/2016 | Brown et al. |
| 9,295,590 B2 | 3/2016 | Brown et al. |
| 9,440,043 B2 | 9/2016 | Arora et al. |
| 9,453,303 B2 | 9/2016 | Aberg et al. |
| 9,486,371 B2 | 11/2016 | Wirtz et al. |
| 9,539,735 B2 | 1/2017 | Ferguson et al. |
| 9,732,454 B2 | 8/2017 | Davis et al. |
| 9,758,339 B2 | 9/2017 | Yanez, Jr. et al. |
| 9,795,520 B2 | 10/2017 | Kaneko et al. |
| 9,877,876 B2 | 1/2018 | Huang et al. |
| 9,903,070 B2 | 2/2018 | Mourad et al. |
| 9,944,047 B2 | 4/2018 | Burt et al. |
| 10,190,244 B2 | 1/2019 | Ashraf et al. |
| 10,577,722 B2 | 3/2020 | Ashraf et al. |
| 10,596,045 B2 | 3/2020 | Koshijima et al. |
| 2001/0029141 A1 | 10/2001 | Mizutani et al. |
| 2001/0030014 A1 | 10/2001 | Kwok |
| 2002/0046802 A1 | 4/2002 | Tachibana et al. |
| 2002/0103469 A1 | 8/2002 | Chen et al. |
| 2002/0134067 A1 | 9/2002 | Heaney et al. |
| 2002/0153271 A1 | 10/2002 | McManus et al. |
| 2002/0177829 A1 | 11/2002 | Fell et al. |
| 2002/0193032 A1 | 12/2002 | Newkirk et al. |
| 2003/0078553 A1 | 4/2003 | Wada |
| 2003/0087056 A1 | 5/2003 | Ducker et al. |
| 2003/0093045 A1 | 5/2003 | Erdman |
| 2003/0119404 A1 | 6/2003 | Belau et al. |
| 2003/0125687 A1 | 7/2003 | Gubernick et al. |
| 2003/0144643 A1 | 7/2003 | Jarpenberg et al. |
| 2003/0203162 A1 | 10/2003 | Fenwick et al. |
| 2003/0203691 A1 | 10/2003 | Fenwick et al. |
| 2003/0211802 A1 | 11/2003 | Keck et al. |
| 2003/0233082 A1 | 12/2003 | Kline et al. |
| 2004/0006323 A1 | 1/2004 | Hall et al. |
| 2004/0059309 A1 | 3/2004 | Nortman |
| 2004/0097895 A1 | 5/2004 | Busam et al. |
| 2004/0121120 A1 | 6/2004 | Gray |
| 2004/0127875 A1 | 7/2004 | Hammons et al. |
| 2004/0127883 A1 | 7/2004 | Cowell et al. |
| 2004/0133180 A1 | 7/2004 | Mori et al. |
| 2004/0158212 A1 | 8/2004 | Ponomarenko et al. |
| 2004/0158217 A1 | 8/2004 | Wu et al. |
| 2004/0219854 A1 | 11/2004 | Groitzsch et al. |
| 2004/0230171 A1 | 11/2004 | Ando et al. |
| 2004/0254554 A1 | 12/2004 | Mavinkurve et al. |
| 2005/0013975 A1 | 1/2005 | Brock et al. |
| 2005/0107764 A1 | 5/2005 | Matsuda et al. |
| 2005/0136773 A1* | 6/2005 | Yahiaoui ............... D06M 15/03 442/394 |
| 2005/0148971 A1 | 7/2005 | Kuroda et al. |
| 2005/0230037 A1 | 10/2005 | Jenquin et al. |
| 2006/0047260 A1 | 3/2006 | Ashton et al. |
| 2006/0069373 A1 | 3/2006 | Schlinz et al. |
| 2006/0087053 A1 | 4/2006 | O'Donnell et al. |
| 2006/0089616 A1 | 4/2006 | Belau et al. |
| 2006/0105075 A1 | 5/2006 | Otsubo |
| 2006/0189954 A1 | 8/2006 | Kudo et al. |
| 2006/0270302 A1 | 11/2006 | Ando et al. |
| 2006/0286343 A1* | 12/2006 | Curro .................. D04H 11/08 428/172 |
| 2007/0026753 A1 | 2/2007 | Neely et al. |
| 2007/0045143 A1 | 3/2007 | Clough et al. |
| 2007/0045144 A1 | 3/2007 | Wheeler et al. |
| 2007/0131335 A1 | 6/2007 | Zhou et al. |
| 2007/0141311 A1 | 6/2007 | Mleziva et al. |
| 2007/0167929 A1 | 7/2007 | Fossum et al. |
| 2007/0179466 A1 | 8/2007 | Tremblay et al. |
| 2007/0298214 A1 | 12/2007 | Noda et al. |
| 2007/0298667 A1 | 12/2007 | Noda et al. |
| 2008/0045915 A1* | 2/2008 | Noda .................. D04H 1/70 604/385.01 |
| 2008/0149292 A1 | 6/2008 | Scherb |
| 2008/0161768 A1 | 7/2008 | Baba et al. |
| 2008/0287897 A1 | 11/2008 | Guzman Reyes et al. |
| 2009/0240222 A1 | 9/2009 | Tomoko et al. |
| 2009/0312730 A1 | 12/2009 | LaVon et al. |
| 2010/0022151 A1 | 1/2010 | Malowaniec |
| 2010/0036346 A1 | 2/2010 | Hammons et al. |
| 2010/0048072 A1 | 2/2010 | Kauschke |
| 2010/0075103 A1 | 3/2010 | Miyamoto |
| 2010/0076394 A1 | 3/2010 | Hayase et al. |
| 2010/0248575 A1 | 9/2010 | Malz |
| 2010/0307668 A1 | 12/2010 | Lange et al. |
| 2011/0118689 A1 | 5/2011 | Een et al. |
| 2011/0250378 A1 | 10/2011 | Eaton et al. |
| 2012/0004633 A1 | 1/2012 | R. Marcelo et al. |
| 2012/0061015 A1 | 3/2012 | Lavon et al. |
| 2012/0061016 A1 | 3/2012 | Lavon et al. |
| 2012/0095429 A1 | 4/2012 | Kobayashi et al. |
| 2012/0196091 A1 | 8/2012 | Mizutani et al. |
| 2012/0296303 A1 | 11/2012 | Ng et al. |
| 2013/0032656 A1 | 2/2013 | Yamamoto |
| 2013/0072887 A1 | 3/2013 | LaVon et al. |
| 2013/0112584 A1 | 5/2013 | Gaspari et al. |
| 2013/0139960 A1 | 6/2013 | Maruyama et al. |
| 2013/0171421 A1 | 7/2013 | Weisman et al. |
| 2013/0199696 A1 | 8/2013 | Schneider et al. |
| 2013/0199707 A1 | 8/2013 | Schneider |
| 2013/0211356 A1 | 8/2013 | Nishikawa et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0261589 A1 | 10/2013 | Fujkawa et al. |
| 2013/0306226 A1 | 11/2013 | Zink et al. |
| 2013/0320584 A1 | 12/2013 | Davis et al. |
| 2014/0000794 A1 | 1/2014 | Hamilton et al. |
| 2014/0018759 A1 | 1/2014 | Jayasinghe et al. |
| 2014/0041797 A1 | 2/2014 | Schneider |
| 2014/0045401 A1 | 2/2014 | Kunihiro et al. |
| 2014/0127460 A1 | 5/2014 | Xu et al. |
| 2014/0148773 A1 | 5/2014 | Brown et al. |
| 2014/0234575 A1 | 8/2014 | Mitsuno et al. |
| 2014/0235127 A1 | 8/2014 | DeJesus et al. |
| 2014/0257231 A1 | 9/2014 | Wang et al. |

(56) References Cited

U.S. PATENT DOCUMENTS

| | | |
|---|---|---|
| 2014/0276517 A1 | 9/2014 | Chester et al. |
| 2014/0296815 A1 | 10/2014 | Takken et al. |
| 2014/0305570 A1 | 10/2014 | Matsunaga et al. |
| 2014/0324009 A1 | 10/2014 | Lee et al. |
| 2014/0343525 A1 | 11/2014 | Roh et al. |
| 2014/0377506 A1 | 12/2014 | Eckstein et al. |
| 2014/0377513 A1 | 12/2014 | Galie et al. |
| 2015/0083309 A1 | 3/2015 | Long et al. |
| 2015/0173967 A1 | 6/2015 | Kreuzer et al. |
| 2015/0230995 A1 | 8/2015 | Kaneko et al. |
| 2015/0282999 A1 | 10/2015 | Arizti et al. |
| 2015/0320613 A1 | 11/2015 | Seitz et al. |
| 2015/0320619 A1 | 11/2015 | Seitz et al. |
| 2015/0328056 A1 | 11/2015 | Een et al. |
| 2015/0351972 A1 | 12/2015 | Bing-Wo |
| 2016/0058624 A1 | 3/2016 | Hohm et al. |
| 2016/0058627 A1 | 3/2016 | Barnes et al. |
| 2016/0067119 A1 | 3/2016 | Weisman et al. |
| 2016/0074256 A1* | 3/2016 | Strube .................. B32B 5/142 428/171 |
| 2016/0100989 A1 | 4/2016 | Seitz et al. |
| 2016/0100997 A1 | 4/2016 | Seitz et al. |
| 2016/0106633 A1 | 4/2016 | Nagata et al. |
| 2016/0129661 A1 | 5/2016 | Arora et al. |
| 2016/0136009 A1 | 5/2016 | Weisman et al. |
| 2016/0228305 A1 | 8/2016 | Gualtieri et al. |
| 2016/0331600 A1 | 11/2016 | Polidori et al. |
| 2016/0355950 A1 | 12/2016 | Young et al. |
| 2017/0000695 A1 | 1/2017 | Castillo et al. |
| 2017/0002486 A1 | 1/2017 | Castillo et al. |
| 2017/0014281 A1 | 1/2017 | Xie et al. |
| 2017/0014291 A1 | 1/2017 | Tao et al. |
| 2017/0027774 A1 | 2/2017 | Ashraf et al. |
| 2017/0029993 A1 | 2/2017 | Ashraf et al. |
| 2017/0029994 A1 | 2/2017 | Ashraf et al. |
| 2017/0056256 A1 | 3/2017 | Smith et al. |
| 2017/0065461 A1 | 3/2017 | Schneider |
| 2017/0079852 A1 | 3/2017 | Fujima et al. |
| 2017/0119595 A1 | 5/2017 | Carla et al. |
| 2017/0121873 A1 | 5/2017 | Kimura et al. |
| 2017/0191198 A1 | 7/2017 | Ashraf et al. |
| 2017/0258650 A1 | 9/2017 | Rosati et al. |
| 2017/0258651 A1 | 9/2017 | Hammons |
| 2017/0319403 A1 | 11/2017 | Bewick-Sonntag et al. |
| 2017/0342617 A1 | 11/2017 | Castillo |
| 2017/0319403 A1 | 12/2017 | Lakso et al. |
| 2018/0002848 A1 | 1/2018 | Burt et al. |
| 2018/0092784 A1 | 4/2018 | Wade et al. |
| 2018/0140473 A1 | 5/2018 | Koshijima et al. |
| 2018/0168874 A1 | 6/2018 | LaVon et al. |
| 2018/0168875 A1 | 6/2018 | LaVon et al. |
| 2018/0168876 A1 | 6/2018 | LaVon et al. |
| 2018/0168877 A1 | 6/2018 | Schneider et al. |
| 2018/0168878 A1 | 6/2018 | Schneider et al. |
| 2018/0168879 A1 | 6/2018 | Schneider et al. |
| 2018/0168880 A1 | 6/2018 | Schneider et al. |
| 2018/0168885 A1 | 6/2018 | Zink, II et al. |
| 2018/0168887 A1 | 6/2018 | LaVon et al. |
| 2018/0168889 A1 | 6/2018 | LaVon et al. |
| 2018/0168890 A1 | 6/2018 | LaVon et al. |
| 2018/0168891 A1 | 6/2018 | Wise et al. |
| 2018/0168892 A1 | 6/2018 | LaVon et al. |
| 2018/0168893 A1 | 6/2018 | Ashraf et al. |
| 2018/0169964 A1 | 6/2018 | Schneider et al. |
| 2018/0170026 A1 | 6/2018 | Schneider et al. |
| 2018/0170027 A1 | 6/2018 | Schneider et al. |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf et al. |
| 2019/0003079 A1 | 1/2019 | Ashraf et al. |
| 2019/0003080 A1 | 1/2019 | Ashraf et al. |
| 2019/0070041 A1 | 3/2019 | Schneider et al. |
| 2019/0070042 A1 | 3/2019 | LaVon et al. |
| 2019/0112737 A1 | 4/2019 | Ashraf et al. |
| 2019/0298586 A1 | 10/2019 | Ashraf et al. |
| 2019/0298587 A1 | 10/2019 | Ashraf et al. |
| 2019/0246196 A1 | 12/2019 | Han et al. |
| 2019/0374392 A1 | 12/2019 | Ninomiya et al. |
| 2019/0374404 A1 | 12/2019 | Ninomiya et al. |
| 2020/0054501 A1 | 2/2020 | Seto et al. |
| 2020/0155370 A1 | 5/2020 | Ohtsubo |
| 2020/0155371 A1 | 5/2020 | Ohtsubo |
| 2020/0206040 A1 | 7/2020 | Andrews et al. |
| 2020/0214901 A1 | 7/2020 | Andrews et al. |
| 2020/0298545 A1 | 9/2020 | Andrews et al. |
| 2020/0360198 A1 | 11/2020 | Ashraf et al. |
| 2020/0397629 A1 | 12/2020 | Aviles et al. |
| 2020/0397630 A1 | 12/2020 | Arora et al. |

FOREIGN PATENT DOCUMENTS

| | | |
|---|---|---|
| CN | 1276196 A | 12/2000 |
| CN | 1342446 A | 4/2002 |
| CN | 1348514 A | 5/2002 |
| CN | 1685009 | 10/2005 |
| CN | 1685099 A | 10/2005 |
| CN | 1731965 A | 2/2006 |
| CN | 1778702 A | 5/2006 |
| CN | 1934306 A | 3/2007 |
| CN | 101410078 A | 4/2009 |
| CN | 101746057 A | 6/2010 |
| CN | 102448418 A | 5/2012 |
| CN | 103502004 A | 1/2014 |
| CN | 104507436 A | 4/2015 |
| CN | 105073079 A | 11/2015 |
| CN | 204931997 U | 1/2016 |
| CN | 105395319 A | 3/2016 |
| CN | 105997351 A | 10/2016 |
| CN | 107809987 A | 3/2018 |
| CN | 108348372 A | 7/2018 |
| EP | 0973470 A1 | 1/2000 |
| EP | 0989218 A1 | 3/2000 |
| EP | 1305248 A2 | 5/2003 |
| EP | 1452157 A1 | 9/2004 |
| EP | 1473148 A1 | 11/2004 |
| EP | 1393701 B1 | 7/2013 |
| EP | 2660377 | 4/2014 |
| EP | 3056176 A1 | 8/2016 |
| EP | 3092997 B1 | 8/2017 |
| EP | 3251642 A1 | 12/2017 |
| EP | 3257488 A1 | 12/2017 |
| EP | 3563817 A1 | 11/2019 |
| JP | H03213543 A | 9/1991 |
| JP | H0430847 A | 2/1992 |
| JP | H06254117 A | 9/1994 |
| JP | H0871107 A | 3/1996 |
| JP | H08132576 A | 5/1996 |
| JP | H1176298 A | 3/1999 |
| JP | 2000026015 A | 1/2000 |
| JP | 2002035029 A | 2/2002 |
| JP | 2002178428 A | 6/2002 |
| JP | 2002238934 A | 8/2002 |
| JP | 2002248127 A | 9/2002 |
| JP | 2003103740 A | 4/2003 |
| JP | 2004229857 A | 8/2004 |
| JP | 2004237410 A | 8/2004 |
| JP | 2004254862 A | 9/2004 |
| JP | 2004298362 A | 10/2004 |
| JP | 2005320636 A | 11/2005 |
| JP | 2006149747 A | 6/2006 |
| JP | 2006149749 A | 6/2006 |
| JP | 2006204673 A | 8/2006 |
| JP | 2007190397 A | 8/2007 |
| JP | 2008029749 A | 2/2008 |
| JP | 2008055198 A | 3/2008 |
| JP | 2008105425 A | 5/2008 |
| JP | 2008148942 A | 7/2008 |
| JP | 2008179128 A | 8/2008 |
| JP | 2008194493 A | 8/2008 |
| JP | 2008229006 A | 10/2008 |
| JP | 2008229007 A | 10/2008 |
| JP | 2008253290 A | 10/2008 |

(56) References Cited

FOREIGN PATENT DOCUMENTS

| | | |
|---|---|---|
| JP | 2008260131 A | 10/2008 |
| JP | 2008264480 A | 11/2008 |
| JP | 2008272250 A | 11/2008 |
| JP | 2008272253 A | 11/2008 |
| JP | 2008296585 A | 12/2008 |
| JP | 2009000161 A | 1/2009 |
| JP | 2009000173 A | 1/2009 |
| JP | 2009039341 A | 2/2009 |
| JP | 2009056156 A | 3/2009 |
| JP | 2009172231 A | 8/2009 |
| JP | 2009240804 A | 10/2009 |
| JP | 2009241607 A | 10/2009 |
| JP | 2010005918 A | 1/2010 |
| JP | 2010131833 A | 6/2010 |
| JP | 2011-015707 | 1/2011 |
| JP | 2011178124 A | 9/2011 |
| JP | 2011225000 A | 11/2011 |
| JP | 2012050882 A | 3/2012 |
| JP | 2012050883 A | 3/2012 |
| JP | 2012105908 A | 6/2012 |
| JP | 2012115358 A | 6/2012 |
| JP | 5124187 B2 | 11/2012 |
| JP | 5124188 B2 | 11/2012 |
| JP | 2013138795 A | 7/2013 |
| JP | 2014-097257 | 5/2014 |
| JP | 2014-188042 | 10/2014 |
| JP | 2015171501 A | 10/2015 |
| JP | 2016013687 A | 1/2016 |
| JP | 2016016536 A | 2/2016 |
| JP | 5942819 B2 | 6/2016 |
| JP | 2016112217 A | 6/2016 |
| JP | 2016193199 A | 11/2016 |
| JP | 6149635 B2 | 6/2017 |
| JP | 2017528612 A | 9/2017 |
| JP | 2017222970 A | 12/2017 |
| JP | 2018102641 A | 7/2018 |
| JP | 2019024947 A | 2/2019 |
| JP | 2019083863 A | 6/2019 |
| JP | 2020054741 A | 4/2020 |
| JP | 2020054742 A | 4/2020 |
| JP | 2020054744 A | 4/2020 |
| JP | 2020054745 A | 4/2020 |
| JP | 2022117131 A | 8/2022 |
| RU | 2424256 C2 | 7/2011 |
| WO | 2006057369 A1 | 6/2006 |
| WO | 2008123348 A1 | 10/2008 |
| WO | 2011137962 A1 | 11/2011 |
| WO | WO201286730 | 6/2012 |
| WO | WO 2003-015681 | 2/2013 |
| WO | WO201318846 | 2/2013 |
| WO | 2013091150 A1 | 6/2013 |
| WO | WO2013/084977 | 6/2013 |
| WO | WO201399625 | 7/2013 |
| WO | WO2013145966 | 10/2013 |
| WO | 2014084168 A1 | 6/2014 |
| WO | 2014196669 A2 | 12/2014 |
| WO | 2015002331 A2 | 1/2015 |
| WO | 2016056092 A1 | 4/2016 |
| WO | 2016056093 A1 | 4/2016 |
| WO | 2016063346 A1 | 4/2016 |
| WO | 2016067387 A1 | 5/2016 |
| WO | 2016071981 A1 | 5/2016 |
| WO | 2016075974 A1 | 5/2016 |
| WO | 2016098416 A1 | 6/2016 |
| WO | 2016104412 A1 | 6/2016 |
| WO | 2016104422 A1 | 6/2016 |
| WO | 2016158499 A1 | 10/2016 |
| WO | 2016158746 A1 | 10/2016 |
| WO | 2016208502 A1 | 12/2016 |
| WO | 2016208513 A1 | 12/2016 |
| WO | 2017004309 A1 | 1/2017 |
| WO | WO 2017-105997 | 6/2017 |
| WO | WO2017110695 | 6/2017 |
| WO | 2018064595 A1 | 4/2018 |
| WO | 2018154680 A1 | 8/2018 |
| WO | 2018154682 A1 | 8/2018 |
| WO | 2018167836 A1 | 9/2018 |
| WO | 2019150802 A1 | 8/2019 |
| WO | 2019246194 A1 | 12/2019 |
| WO | 2019246196 A1 | 12/2019 |

OTHER PUBLICATIONS

PCT International Search Report, dated May 16, 2017 (6 pages).
PCT International Search Report, dated Jul. 31, 20115 (9 pages).
PCT International Search Report, dated Mar. 13, 2018 (5 pages).
PCT International Search Report, dated Apr. 11, 2018 (5 pages).
PCT International Search Report, dated Jan. 31, 2017 (12 pages).
PCT International Search Report, dated May 16, 2018 (5 pages).
PCT International Search Report, dated Jan. 31, 2017 (13 pages).
PCT International Search Report, dated Mar. 6, 2017 (5 pages).
PCT International Search Report, dated Apr. 11, 2019 (5 pages).
All Office Actions U.S. Appl. No. 15/221,624.
All Office Actions U.S. Appl. No. 15/221,625.
All Office Actions U.S. Appl. No. 15/221,626.
All Office Actions U.S. Appl. No. 15/221,628.
All Office Actions U.S. Appl. No. 15/840,455.
All Office Actions U.S. Appl. No. 15/879,474.
All Office Actions U.S. Appl. No. 15/879,477.
All Office Actions U.S. Appl. No. 15/879,480.
All Office Actions U.S. Appl. No. 15/879,485.
All Office Actions U.S. Appl. No. 15/881,910.
All Office Actions U.S. Appl. No. 16/019,724.
All Office Actions U.S. Appl. No. 16/019,785.
All Office Actions U.S. Appl. No. 16/214,526.
3D Nonwovens Developments for textured nonwovens; Detlef Frey; http://web.archive.org/web/20170919080326/https://www.reicofil.com/en/pages/3d_nonwovens, Sep. 19, 2017.
International Search Report and Written Opinion, PCT/US2019/037892.
All Office Actions, U.S. Appl. No. 16/445,838.
All Office Actions, U.S. Appl. No. 16/446,052.
All Office Actions, U.S. Appl. No. 16/446,118.
All Office Actions, U.S. Appl. No. 16/446,156.
All Office Actions; U.S. Appl. No. 17/935,951, filed Sep. 28, 2022.
U.S. Unpublished U.S. Appl. No. 17/935,951, filed Sep. 28, 2022, to Arman Ashraf et al.
All Office Actions; U.S. Appl. No. 18/331,240, filed Jun. 8, 2023.
U.S. Unpublished U.S. Appl. No. 18/331,240, filed Jun. 8, 2023, to Arman Ashraf et al.
All Office Actions; U.S. Appl. No. 18/487,172, filed Oct. 16, 2023.
U.S. Unpublished U.S. Appl. No. 18/487,172, filed Oct. 16, 2023, to Kelyn Anne Arora et al.

\* cited by examiner

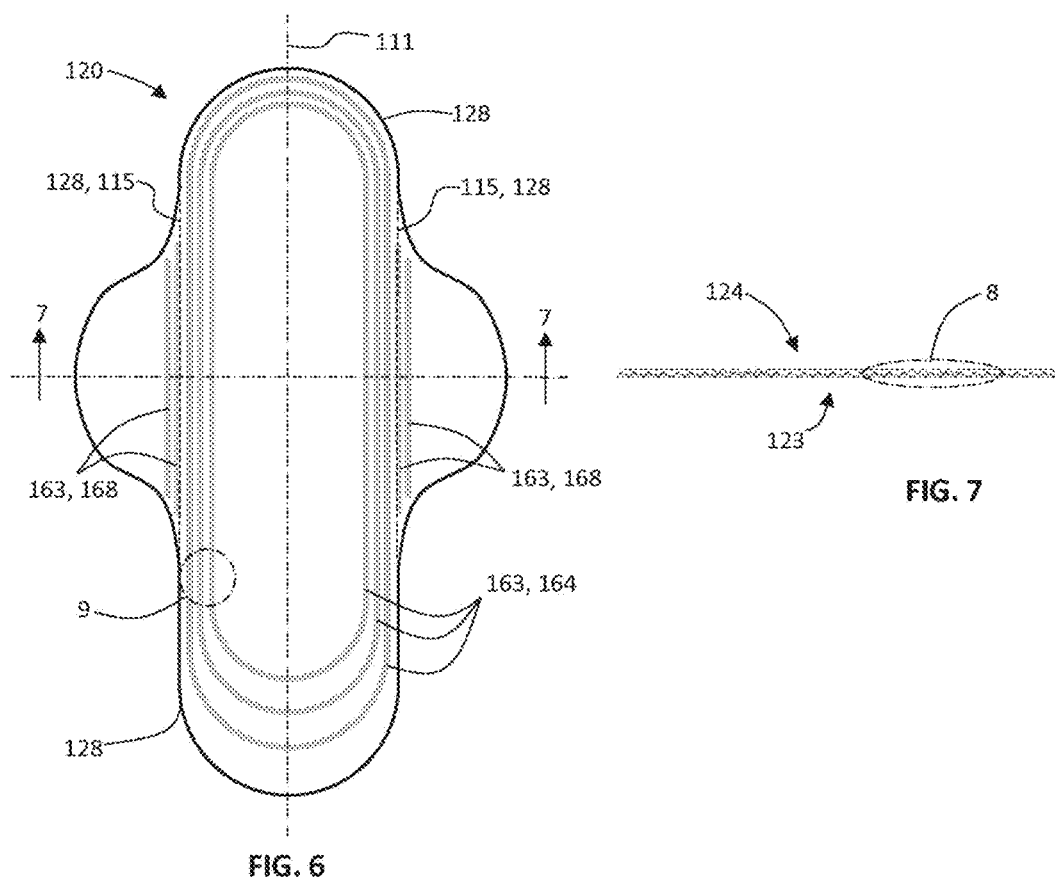
FIG. 6
FIG. 7
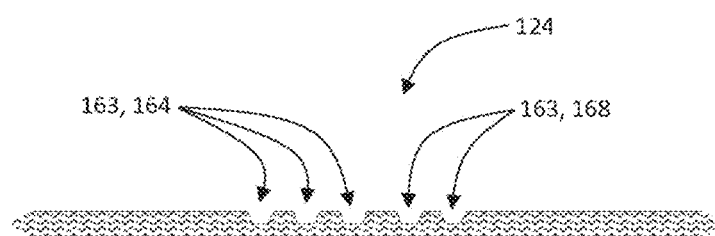
FIG. 8

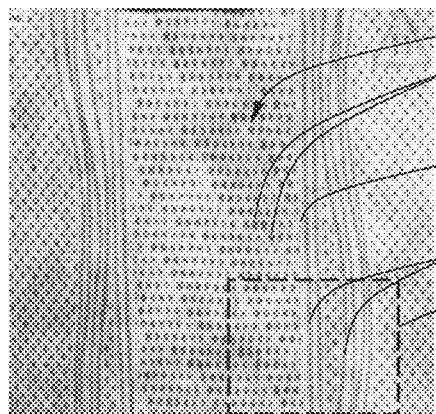
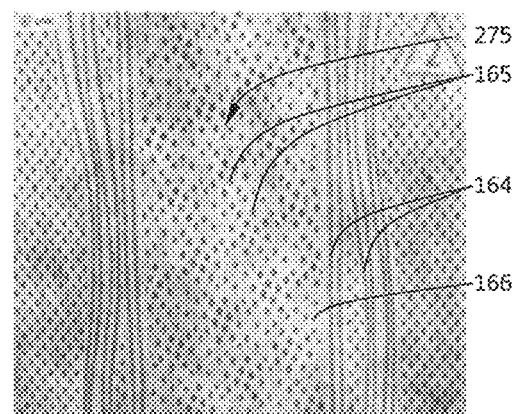
FIG. 26A  FIG. 26B
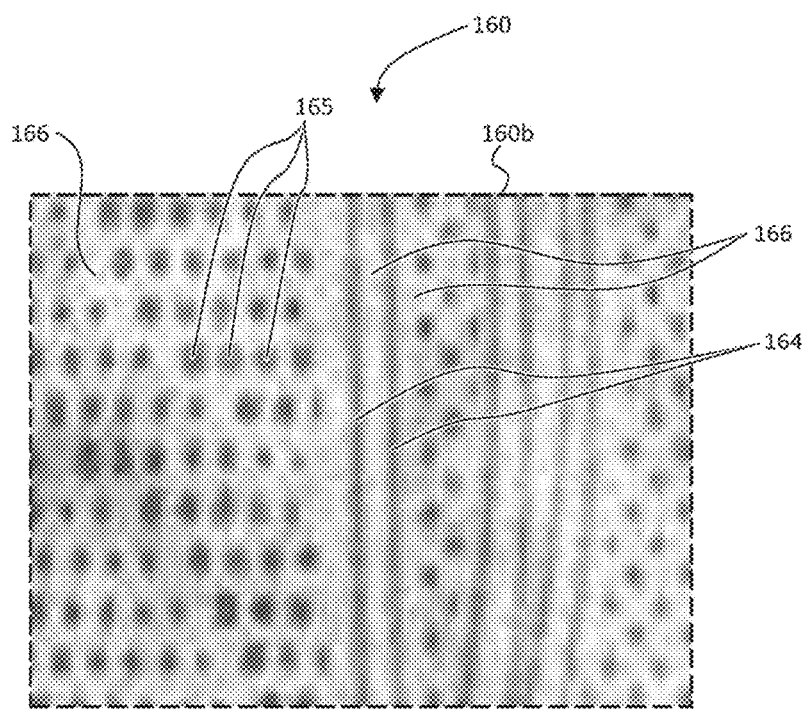
FIG. 27

ABSORBENT ARTICLE WITH FUNCTION-FORMED TOPSHEET, AND METHOD FOR MANUFACTURING

CROSS REFERENCE TO RELATED APPLICATIONS

This application claims the benefit of U.S. provisional Application No. 62/687,043, filed Jun. 19, 2018, and is a continuation-in-part of application Ser. No. 15/879,474, filed Jan. 25, 2018, the substances of which are incorporated herein by reference.

FIELD OF THE INVENTION

The present disclose relates to disposable absorbent articles such as feminine hygiene pads, and particularly articles and pads having topsheets having structural features formed therein.

BACKGROUND OF THE INVENTION

Wearable disposable absorbent articles such as feminine hygiene pads, adult incontinence pads and disposable diapers typically include a topsheet of material adapted to serve as the wearer-facing outer layer of an envelope structure that contains absorbent material. Typically the topsheet is adapted to be liquid permeable such that liquid body exudates may pass therethrough, to reach the absorbent material contained in the envelope structure, and be absorbed and retained by the absorbent material until the time the article is removed and discarded. Generally it is desired that the topsheet serve to readily receive aqueous fluid such as urine or menstrual fluid, conduct the fluid in a z-direction therethrough, and release or desorb it to an absorbent structure disposed adjacently beneath the topsheet.

For combined purposes of cost effectiveness, wearer comfort and functionality, topsheets of many currently-marketed absorbent articles are made of nonwoven web material formed in some portion, or entirely, of filaments spun from polymer resins. Through a number of technologies currently known, various types of nonwovens may be manufactured to have sufficient liquid permeability, suitably soft feel to the skin, and mechanical strength making them suitable for forming topsheets. Nonwoven web materials ("nonwovens") may be formed of synthetic fibers, such as but not limited to fibers spun from polyolefins, polyesters, polyamides, etc., or combinations thereof. Nonwovens may be formed using various processes that form a cohesive fabric-like web in which the fibers are "continuous" (of relatively long, variable and indefinite lengths) or staple fibers (fibers cut into relatively short and substantially uniform lengths).

Various attempts have been made to make nonwovens used to form topsheets visually appealing to wearers/users, to impart them with an appearance of having functionally beneficial attributes, and/or to impart them with actually functionally beneficial attributes. Such attempts have included printing with decorative or functionally suggestive print designs; or embossing and/or bonding to impart decorative, functionally suggestive or even actually functional surface topographical features. These attempts involve transformations generally occurring downstream of formation of a batt of filaments, and have been of limited effect with respect to imparting a perceivably dramatic set of three-dimensional topographical features and/or imparting beneficial functionality. Accordingly, there is room for improvement in cost-effective techniques for imparting three-dimensional structural features to nonwoven web materials to be used to make topsheets. Additionally, currently available absorbent articles with nonwoven topsheets have left room for improvement in providing for rapid acceptance and movement of fluid down into the absorbent structure following discharge, avoidance of fluid retention in the topsheet, and rewetting.

SUMMARY OF THE INVENTION

The invention is an absorbent article (in some examples, a feminine hygiene pad) including a liquid permeable topsheet, the topsheet having features formed therein via a disposition of filaments that form attenuated regions adjacent to built-up regions according to an ordered arrangement. The attenuated regions have a first average basis weight and the built-up regions have a second average basis weight greater than the first average basis weight, the difference in basis weights corresponding to disposition of the filaments according to the ordered arrangement. In some examples the attenuated regions are comprised by a configuration of one or more channel portions that predominately circumscribe a discharge locus on the topsheet along a longitudinal axis. The low basis weight attenuated regions of the channel portions with adjacent higher basis weight built-up regions serve a distribution and containment function wherein discharged fluid can move along the channel portions and also move in a z-direction through the topsheet (to an absorbent structure beneath), while fluid movement across the topsheet along x and y directions beyond the channel portions is inhibited by the built-up regions outside the channel portions. In combination or in other examples that include feminine hygiene pads, the attenuated regions may be comprised by hinge portion(s) along wing portions. The hinge portions can both visually indicate a wing folding location/line and facilitate bending of the wing portions therealong.

BRIEF DESCRIPTION OF THE DRAWINGS

FIG. 6 is a plan view of an example of a topsheet for an absorbent article in the form of a feminine hygiene pad.

FIG. 7 is a schematic lateral cross section of the topsheet of FIG. 6, taken along a lateral axis.

FIG. 8 is an expanded schematic view of the portion of the cross section identified as "8" in FIG. 7.

FIGS. 26A and 26B are grayscale reproductions of photographs of samples of nonwoven web material having discrete low bulk portions, channel portions and built-up regions.

FIG. 27 is an enlarged view of the zone 160 identified in FIG. 26A.

DESCRIPTION OF EXAMPLES

Definitions

Figure 1:
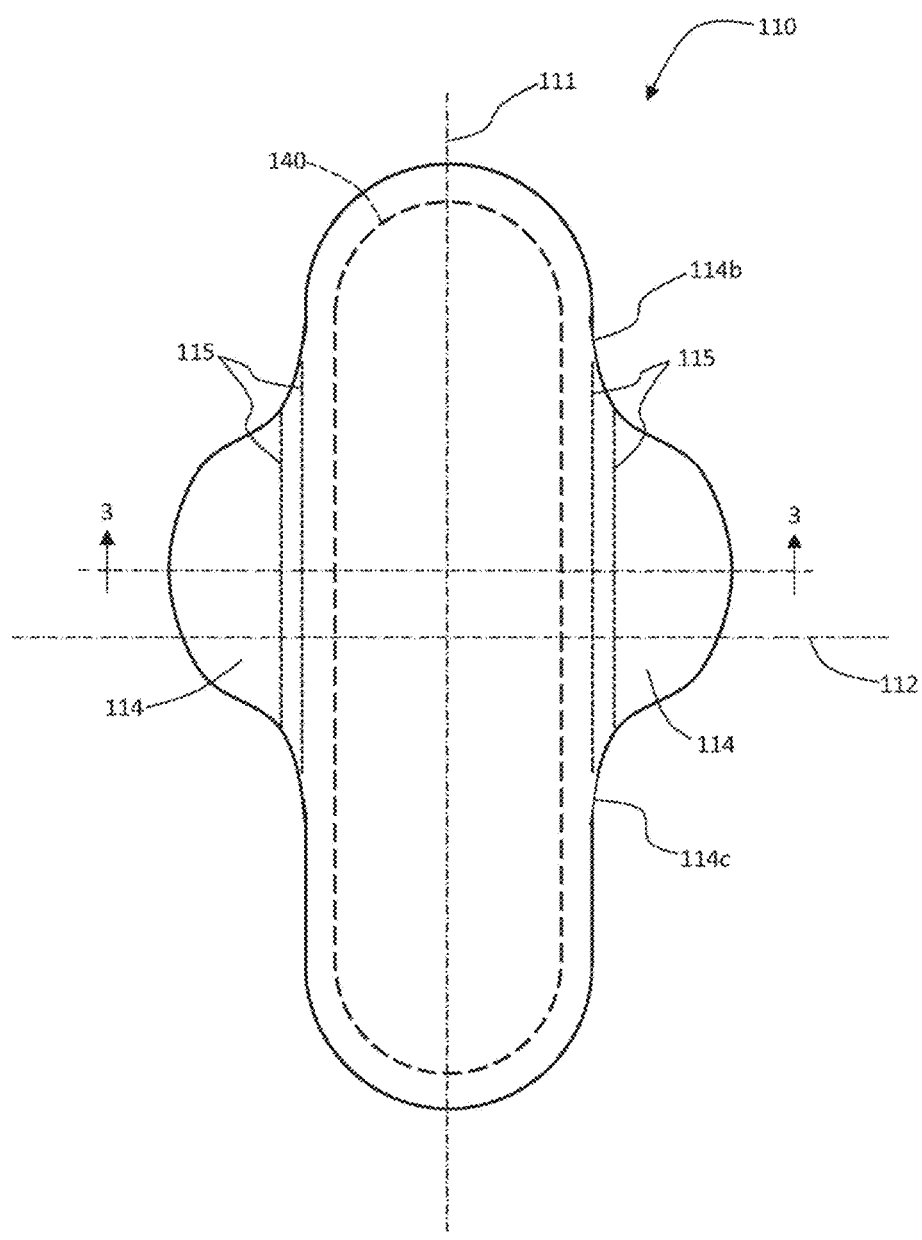
FIG. 1 is a plan view of an example of an absorbent article in the form of a feminine hygiene pad.
Figure 2:
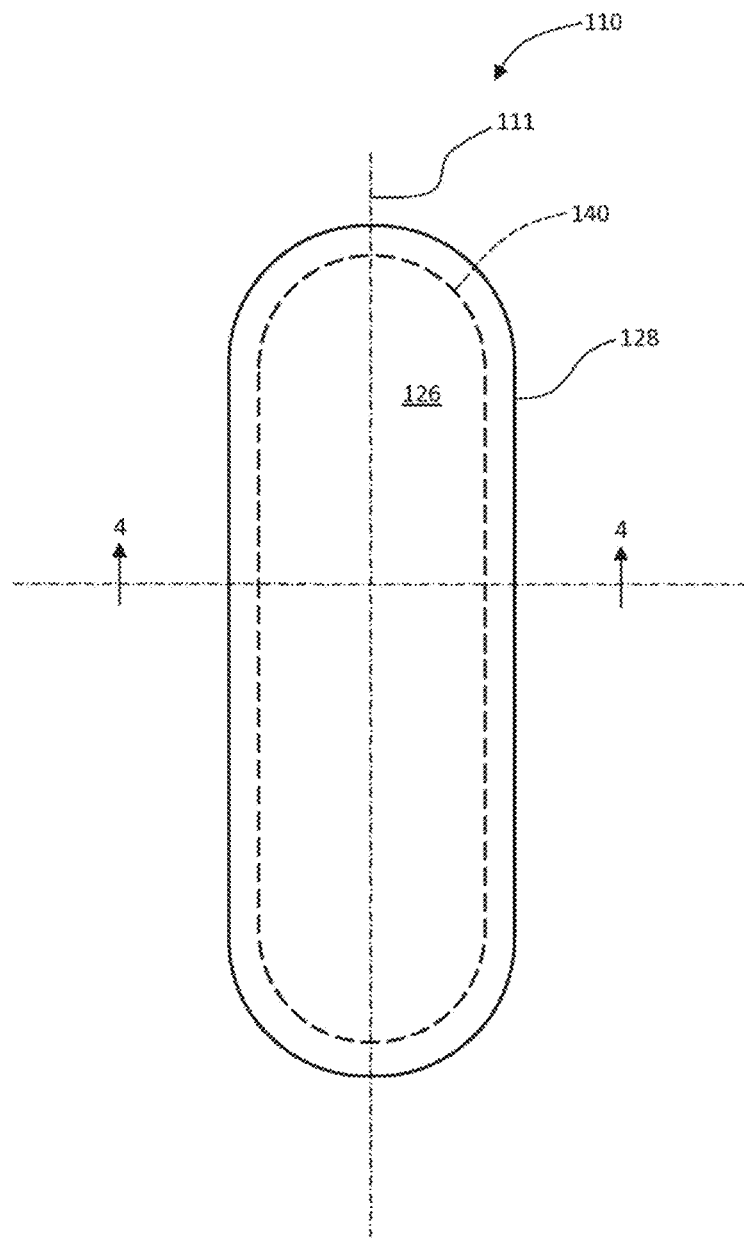
FIG. 2 is a plan view of the pad of FIG. 1, shown with wing portions turned under and thereby depicting an in-use wear-facing portion.

With respect to a nonwoven web material formed partially or entirely of fibers and/or filaments, a "bond" is a three-dimensional zone within the material in which a plurality of the filaments are held together in a unitary mass created by one or a combination of a deposit of adhesive applied to the material, thermal fusing caused by localized application of heating energy to the material (for example, heat from defined bonding protrusions on a heated bonding roller, or ultrasonic vibratory energy from a sonotrode in combination with a bonding roller with defined bonding protrusions), or plastic deformation and entanglement or intermeshing caused by localized application of pressure (for example, by a bonding roller with defined bonding protrusions) to the material in the z-direction. A bond has a two-dimensional profile along the x-y plane approximated by the large surfaces of the web material, as well as a z-direction dimension. When bonds are created via use of a bonding roller with defined bonding protrusions, the two-dimensional profiles of the bonds will approximately reflect the shape(s) of the bonding protrusions.

"Fiber" as used herein means an elongate particulate having a length less than 5.08 cm (2 in.). In the field of nonwoven web manufacturing, fibers are typically considered discontinuous in nature. Non-limiting examples of fibers include natural fibers such as wood pulp, cotton and bamboo fibers, and synthetic staple fibers (which may be manufactured by chopping filaments) such as polypropylene, polyethylene, polyester, copolymers thereof, rayon, lyocell, glass fibers and polyvinyl alcohol fibers.

"Filament" as used herein means an elongate particulate having a length equal to or greater than 5.08 cm (2 in.). In the field of nonwoven web manufacturing, filaments are typically considered to be of indefinite length and/or be substantially continuous in nature with respect to nonwoven web materials in which they appear, in contrast to fibers, it being recognized that they cannot be of infinite length. Non-limiting examples of filaments include meltblown and/or spunbond filaments. Non-limiting examples of polymers that may be spun into filaments include natural polymers, such as starch, starch derivatives, cellulose, such as rayon and/or lyocell, and cellulose derivatives, hemicellulose, hemicellulose derivatives, and synthetic polymers including, but not limited topolyvinyl alcohol filaments and/or polyvinyl alcohol derivative filaments, and thermoplastic polymers such as polyesters, nylons, polyolefins such as polypropylene, polyethylene, and copolymers thereof, and biodegradable or compostable thermoplastics such as polylactic acid, polyhydroxyalkanoate, polyesteramide, and polycaprolactone; bio-sourced or bi-derived polymers (such as but not limited to bio-sourced polyethylene); and recycled polymeric materials (such as but not limited to recycled PET). Spun filaments may be monocomponent or multicomponent, for example, bicomponent.

The "region basis weight" of a region of a section of formed nonwoven web material means the weight in grams of the region of interest, divided by its surface area on one side, measured by any appropriate measurement technique including but not necessarily limited to the Localized Basis Weight measurement method described herein.

"Intensive properties" of a region of a nonwoven web material include basis weight; aggregate total of the lengths of all fibers and/or filaments present per unit surface area of the material lying along an x-y plane (referred to herein as fiber and/or filament "area density"); caliper/thickness in the z-direction; and density (mass per unit volume).

"Lateral," with respect to a feminine hygiene pad, adult incontinence pad, or disposable diaper, refers to the direction perpendicular to the longitudinal direction, and from side-to-side of the article from the wearer's perspective.

"Longitudinal," with respect to a feminine hygiene pad, adult incontinence pad, or disposable diaper, refers to the direction from front-to-rear or from rear-to-front of the article from the wearer's perspective.

"Nonwoven," with respect to a fabric of web of material, means a fabric or web formed predominately of fibers, filaments or a combination thereof, which are not knitted or woven, but rather are laid down and accumulated into a batt and then consolidated and held together in a coherent fabric web of material by entangling, a dispersed binding agent, a pattern of discrete bonds formed by localized deposits of adhesive, localized thermal fusing, localized plastic deformation and entanglement between fibers or filaments caused by localized applications of pressure, or a combination thereof.

"Ordered arrangement," with respect to a section of formed nonwoven web material having a regular (repeating) pattern or configuration of zones that each include adjacent regions of differing intensive properties, or an irregular (non-repeating) pattern or configuration of zones that each include adjacent regions of differing intensive properties, along a surface of the material, means an arrangement of such zones that is recognizable by a person of ordinary skill in the art of nonwoven web manufacturing as an ordered, non-random arrangement or pattern, as contrasted with a random, unordered accumulation and distribution of filaments and/or fibers. As will be recognized by persons of ordinary skill in the art relevant to this disclosure, an ordered arrangement of such zones will result from process steps and equipment used to manufacture the nonwoven web material, configured to repeatably effect the ordered arrangement in the nonwoven web material. An ordered arrangement of zones in a nonwoven web material may reflect an ordered arrangement of features of forming equipment, such as an ordered arrangement of features on a forming belt.

"Visually discernible" means visible and visually detectable from a distance of approximately 0.5 meter or more, to the naked eye of an ordinary observer having 20/20 vision, under indoor office lighting conditions deemed appropriate for reading printed text media.

A "zone" is a zone of a nonwoven web material comprising at least first and second adjacent regions thereof, the first and second adjacent regions having differences in one or a combination of basis weight, caliper, density (mass/volume), and/or fiber and/or filament area density.

A "region" is a sub-portion of a "zone", defined by and distinguished from other sub-portions of the zone by one or a combination of a difference in basis weight, caliper, density (mass/volume), and/or fiber and/or filament area density.

An ordered arrangement of "attenuated regions" of relatively low basis weight in a nonwoven material, wherein filaments are present in relatively low numbers, is distinguishable from an ordered arrangement of apertures or holes through a nonwoven material, in that "attenuated regions" in an ordered arrangement have randomly and varyingly located and varyingly oriented filaments passing thereacross between portions of an adjacent built-up region(s) of relatively higher basis weight, whereas apertures or holes in an ordered arrangement will have an identifiable, consistent absence of filaments passing thereacross between neighboring unapertured portions.

A "discrete" low bulk portion or "discrete" attenuated region means one that is entirely surrounded (in an x-y plane) by a continuous area of built-up region, and has a largest dimension in the x-y plane no greater than 1 cm.

"z-direction," with respect to a nonwoven web material or portion thereof lying along an x-y plane, means the direction orthogonal to the x-y plane. "z-direction," with respect to a forming belt used to manufacture a nonwoven web material moving through a working location of belt travel lying along an x-y plane, means the direction orthogonal to the x-y plane.

"Liquid-permeable" and "liquid-impermeable" refer to the penetrability of materials in the context of the intended usage of disposable absorbent articles. Specifically, the term "liquid-permeable" refers to a layer or a layered structure having pores, openings, and/or interconnected void spaces that permit aqueous liquid such as water, urine, or synthetic urine to pass through its thickness in the absence of a forcing pressure. Conversely, the term "liquid-impermeable" refers to a layer or a layered structure through the thickness of which aqueous liquid such as water, urine, or synthetic urine cannot pass in the absence of a forcing pressure (aside from natural forces such as gravity). A layer or a layered structure that is liquid-impermeable according to this definition may be permeable to liquid vapor, i.e., may be "vapor-permeable."

With respect to a component of a wearable absorbent article constructed of a plurality of components, a "wearer-facing" component is the component disposed closest to the wearer's skin when the article is worn, and an "outward-facing" component is the component disposed furthest from the wearer's skin. With respect to two opposing major surfaces of a web, sheet or batt component of a wearable absorbent article, the "wearer-facing" surface is the surface facing the wearer's skin when the article is worn, and the opposing "outward-facing" surface is the surface facing away from the wearer's skin.

Absorbent Articles

Referring to FIGS. 1-4, a wearable absorbent article may have the form of a feminine hygiene pad 110. Pad 110 has a longitudinal axis 111 and a lateral axis 112 and may include a wearer-facing, liquid-permeable topsheet 120, outward-facing, liquid-impermeable backsheet 130, and an absorbent structure 140 disposed between and enveloped by the topsheet and backsheet. It will be recognized that adult incontinence pads, disposable absorbent pants and disposable diapers also may include this general structure.

Figure 3:
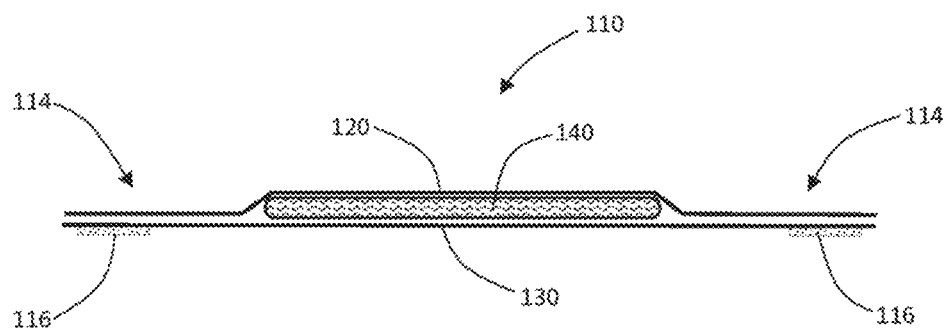
FIG. 3 is a schematic lateral cross section view of the pad of FIG. 1, taken along a lateral axis.
Figure 4:
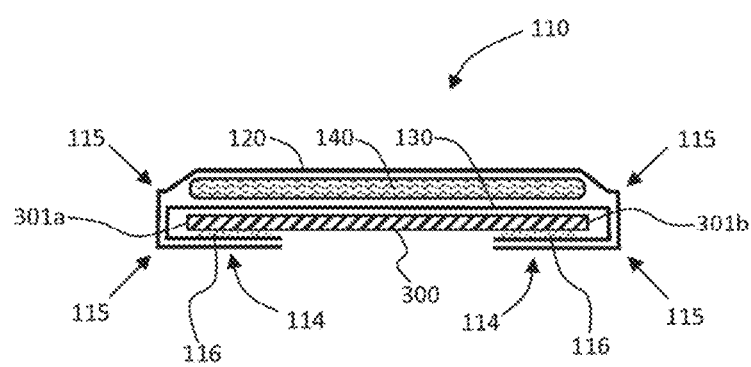
FIG. 4 is a schematic lateral cross section view of the pad with wing portions folded under as depicted in FIG. 2, taken along a lateral axis, shown associated with a crotch portion of a pair of underpants.
Figure 5A:
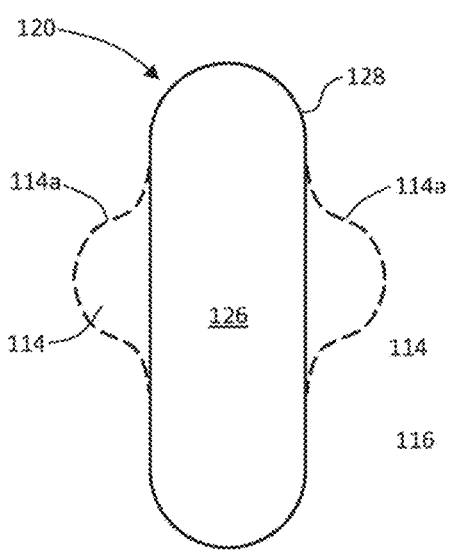
FIGS. 5A-5D are plan views of non-exclusive examples of topsheets of various shapes.
Figure 5B:
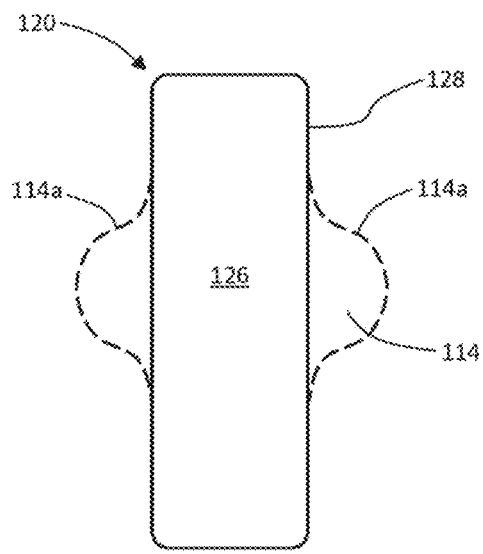
Figure 5C:
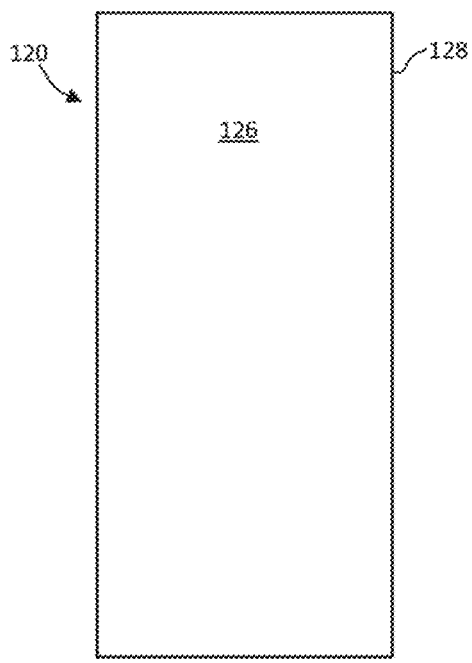
Figure 5D:
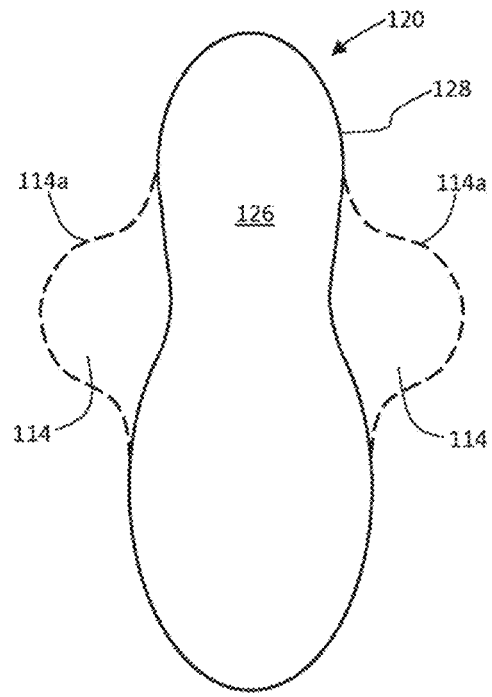

Many currently marketed feminine hygiene pads 110 include wing portions such as depicted wing portions 114. Some currently marketed adult incontinence pads also include wing portions of similar positioning and configuration. Wing portions 114 may be portions of one or both of the topsheet and backsheet materials, without any substantial portion of the absorbent structure 140 or quantity of absorbent material between them, which extend laterally away from the longitudinal axis 111. Referring to FIGS. 3 and 4, wing portions 114 may be provided to allow the user to place the pad 110 inside the user's underpants over the crotch portion 300 thereof, and fold and wrap the wing portions 114 over the insides of the respective left and right leg opening edges 301a, 301b of the underpants, through the leg openings and about the outer surface of the underpants in the crotch region. Wing portions 114 may be provided with deposited patches of adhesive 116 to allow the user to adhere the wing portions 114 to the outer surface of the underpants in the crotch portion 300, helping hold the pad in place within the underpants during wear, and protecting the underpants about the leg opening edges from staining by exudates. When included and used for these purposes, wing portions 114 are required to flex and/or fold along approximately longitudinal wing fold lines 115 (see FIGS. 1 and 4). For purposes herein, a wing portion 114 of a feminine hygiene pad 110 may be identified as a portion that includes no substantial portion of the absorbent structure 140 and no substantial quantity of absorbent material therewithin, the portion having a profile that extends laterally away from the longitudinal axis 111 of the pad, beginning approximately at a forward inflection point 114b where the outer perimeter changes direction, away from a direction approximately parallel the longitudinal axis toward a direction perpendicular to the longitudinal axis, and ending approximately at a rearward inflection point 114c where the outer perimeter approaches the longitudinal axis and then changes direction away from a direction perpendicular the longitudinal axis, toward a direction to parallel to the longitudinal axis, where inflection points 114b, 114c are the two points along the perimeter that are closer to the longitudinal axis than any other points along the perimeter of the wing portion. See, e.g., FIG. 1. The wing portion may be substantially delineated from the main portion of the pad by a line connecting the two inflection points 114b, 114c.

When wing portions 114 of a pad 110 are folded for use as described above, the topsheet has an in-use wearer-facing surface 126 that does not include the wing portions 114. In-use wearer-facing surface 126 has an outer perimeter 128. In other types of pads and diapers, wing portions 114 may be omitted, in which circumstance the in-use wearer-facing surface 126 of the topsheet and the outer perimeter 128 may be coextensive. Various non-limiting examples of possible topsheets with in-use wearer-facing portions 126 and outer perimeters 128 thereof are illustrated in FIGS. 5A-5D. As suggested in FIGS. 5A, 5B and 5D, wing portions 114 with outer edges 114a may be included, or may be omitted, depending upon the style of article desired to be provided. As suggested in FIG. 5C, some types of wearable absorbent articles such as disposable diapers may have topsheets 120 with a simple rectangular shape.

Formed Topsheet Features

Referring now to FIGS. 6-10, a topsheet 120 for an absorbent article such as a feminine hygiene pad may be formed of a section of formed nonwoven web material imparted with certain features to enhance visual appearance and provide beneficial functionality. A topsheet 120 formed of a section of formed nonwoven web material may be provided with one or more attenuated regions 163 defining channel portions 164. Channel portions 164 may be disposed to the inside of, proximate to, and may approximately parallel, outer perimeter 128 of in-use wearer-facing portion. Although depicted as defining continuous oval- or stadium-shapes in FIG. 6, channel portions 164 may be discontinuous, and may be present only along the sides, only along the ends, or portions or intervals, of in-use wearer-facing portion 126 of topsheet 120 with outer perimeter 128.

For purposes of reducing the chances of exudate fluid migration across the topsheet to the edges thereof, it may be desired that the configuration of channel portion(s) 164 have certain features.

In some examples, it may be desired than any configuration of channel portion(s) 164 that is present, not have a portion that extends continuously along a path from an area proximate a discharge locus out to any edge of the topsheet. Avoiding inclusion of such a channel portion will avoid creating a channel for discharged fluid to migrate to an edge of the topsheet or in-use wearer-facing portion 126 thereof, with the attendant possibility of leakage of discharged fluid off the pad.

In non-limiting examples such as depicted in FIGS. 22 and 23A-23K, it may be desired that a configuration of channel portion(s) 164 be substantially symmetric about longitudinal axis 111 of the topsheet 120 and/or of the article 110.

In some examples such as some types and/or sizes of feminine hygiene pads and baby diapers, it may be desired that a configuration of channel portion(s) 164 be longitudinally centered about a lateral discharge locus 112b that is offset from the lateral axis 112 of the article (as identified in FIG. 1), such that the configuration of channel portion(s) 164 is not longitudinally centered or symmetric about lateral axis 112.

For a feminine hygiene pad, for example, this configuration may be desired where it is preferred that the pad be placed within the user's underpants such that a greater proportion of absorbent structure surface area within the x-y plane be located rearward of the expected discharge locus 112b (which is the location on the article expected to first receive a discharge of fluid during normal use of the article, located along the longitudinal axis 111 and at the midpoint of the longitudinal dimension of the configuration of channel portion(s) 164). For example, for some types and sizes of feminine hygiene pads, it may be desired that the greater proportion of absorbent structure surface area be located to the rear of the expected discharge locus 112b on the topsheet (where the discharge locus 112b is the location on the topsheet expected to be most proximate the user's vaginal opening during use/wear). In such examples it may be preferred that the greater proportion of absorbent structure surface area be located rearward of the discharge locus because discharged menstrual fluid often moves rearward through a pad as a result of proximity of the pad to the user's body as held in place by underpants, anatomical features and typical ranges of body positions and movements during use/wear. When the configuration of channel portion(s) 164 is visually discernible when formed as described herein, its visible location may serve to guide the user in appropriately locating and placing the pad within the user's underpants for use/wear. In some examples, any wing portions 114 included may be approximately longitudinally centered about the lateral discharge locus 112b, as suggested by way of non-limiting example in FIG. 22.

In other examples, it may be desired that the configuration of channel portion(s) 164 be longitudinally centered about the lateral axis 112 of the article, and for some examples, be symmetric about the lateral axis 112. In such examples, the expected discharge locus may be at the intersection between the longitudinal axis 111 and lateral axis 112.

Figure 24A:
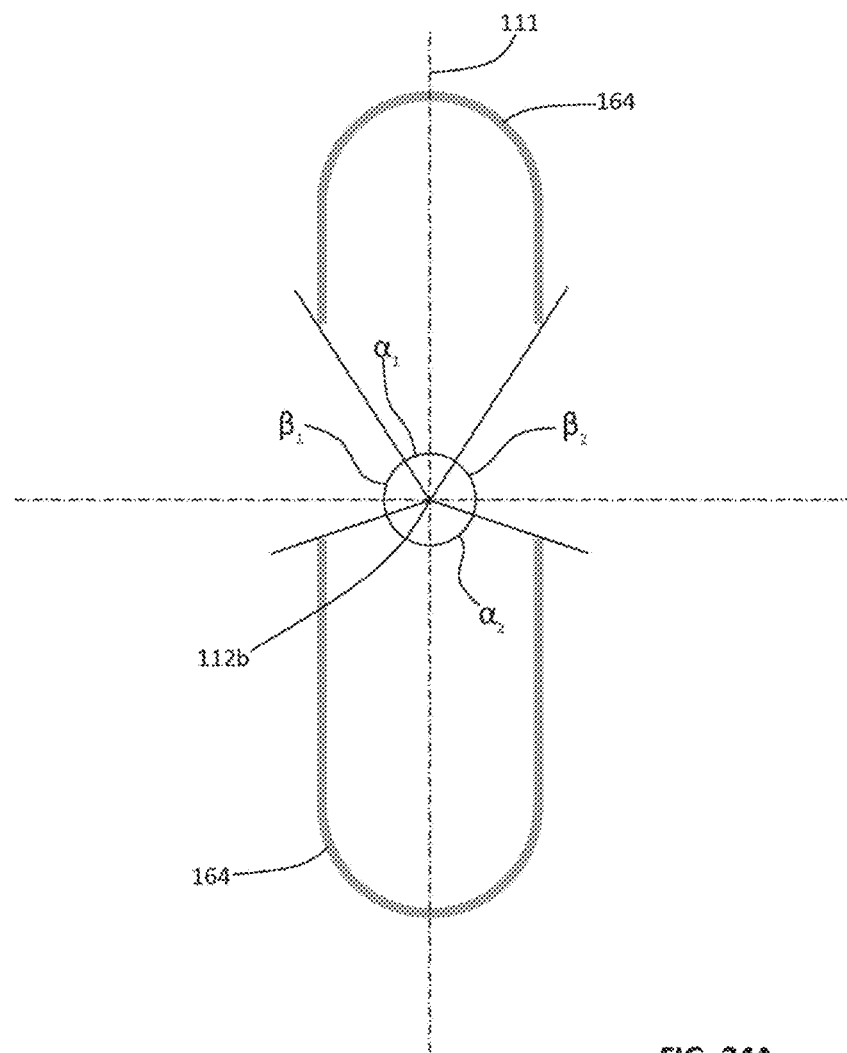
FIGS. 24A-24E are plan views of examples of configurations of channel portions for a topsheet, shown with geometric references for determining whether the configurations predominately circumscribe a discharge locus on the topsheet.
Figure 24B:
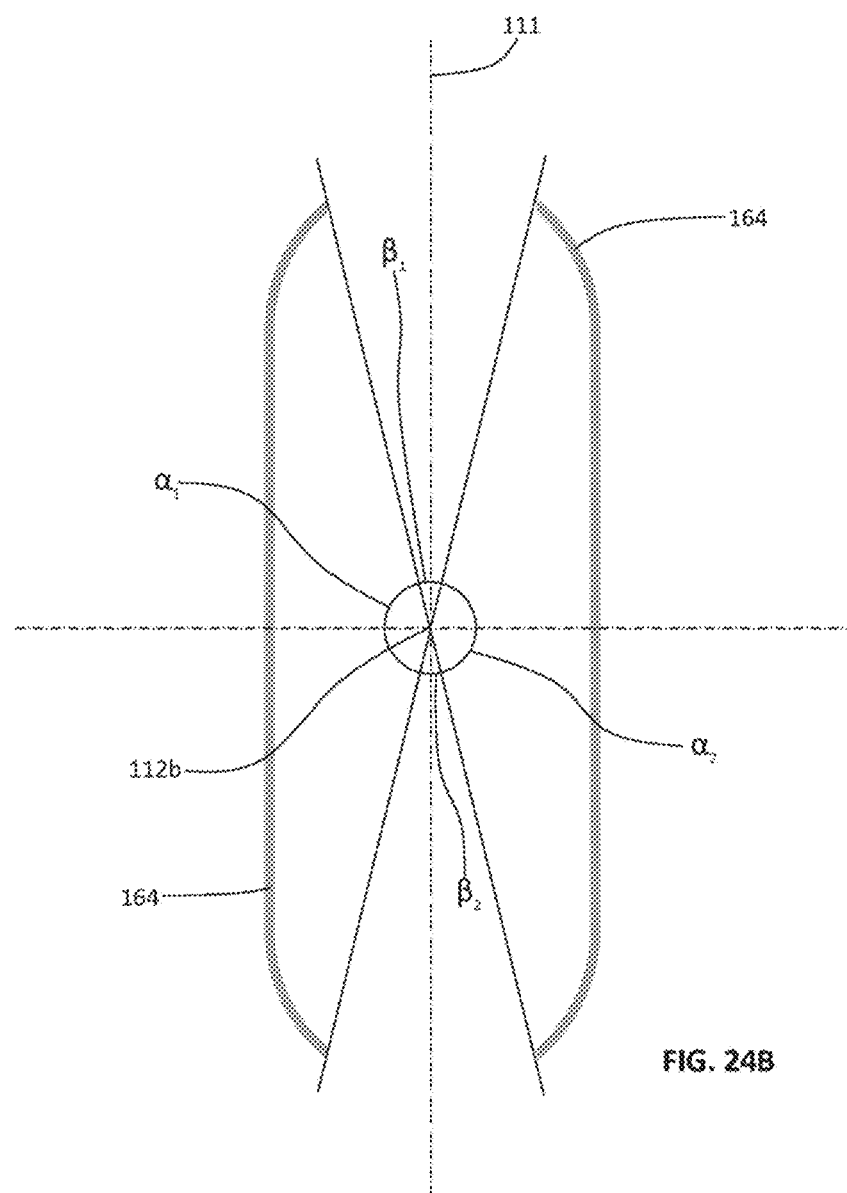
Figure 24C:
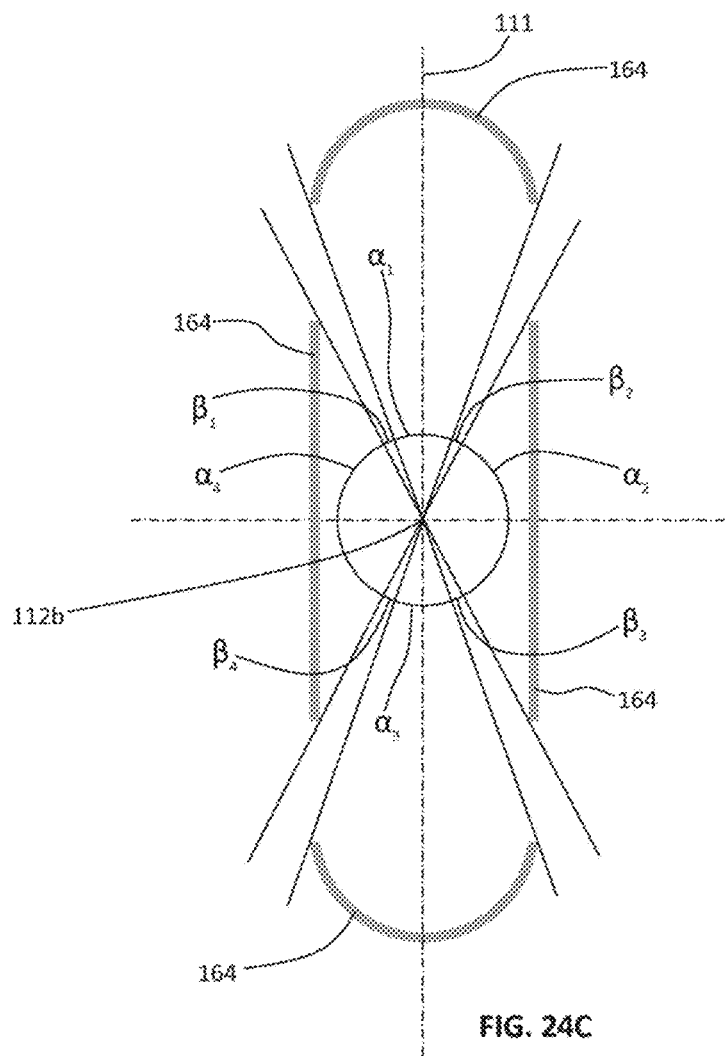

In many circumstances, it may be desired that a configuration of one or more channel portions 164 occupy one or more paths that, individually or in combination, predominately circumscribe a discharge locus 112b. Referring to FIGS. 24A-24C, for purposes herein, a path or plurality of paths of a configuration of channel portions 164 "predominately circumscribe" a discharge locus 112b, when a ray drawn in the x-y plane along the pad surface, originating at a discharge locus 112b and extending radially outwardly in the x-y plane therefrom, will intersect a channel portion 164 when drawn in any of a predominately greater number of possible angular positions about a 360-degree circle with its center at the discharge locus 112b. Referring to FIGS. 24A-24C, by way of illustration, angles $\alpha$ delineate angular portions of a circle within which any ray extending from the center thereof will intersect a channel portion 164; and angles $\beta$ delineate angular portions of the circle within which any ray extending from the center will not intersect a channel portion 164. Thus, each of the illustrative examples of channel portion 164 configurations shown in FIGS. 24A-24C predominately circumscribe a discharge locus 112b, because the total of the angles $\alpha$ is greater than the total of the angles $\beta$, i.e., total of angles $\alpha$ is greater than 180 degrees. For FIGS. 24A and 24B, $$(\alpha_1+\alpha_2)>+(\beta_1+\beta_2);$$

and for FIG. 24C, $$(\alpha_1+\alpha_2+\alpha_3+\alpha_4)>+(\beta_1+\beta_2+\beta_3+\beta_4).$$

For purposes of identifying a discharge locus 112*b* and determining whether a configuration of channel portion(s) 164 predominately circumscribes it, a discharge locus 112*b* may lie anywhere on or approximately on longitudinal axis 111, at any point therealong that is predominately circumscribed by a configuration of channel portion(s) 164 as described above and is within the middle third of the length of the topsheet along the longitudinal axis 111. To illustrate, referring to FIG. 24E, a discharge locus 112$b_A$ is predominately circumscribed by channel portion 164 because angle $\alpha_A$ is greater than angle $\beta_A$, where such a discharge locus 112$b_A$ may be identified along longitudinal axis 111 within the middle third (⅓Lm) of length L. The condition is satisfied in any example in which such a discharge locus such as locus 112$b_A$ may be identified, despite the possibility, with some configurations of channel portions 164, of identifying alternate locations such as location 112$b_B$ along axis 111 where, e.g., angle $\alpha_B$ is less than angle $\beta_B$.

Figure 24D:
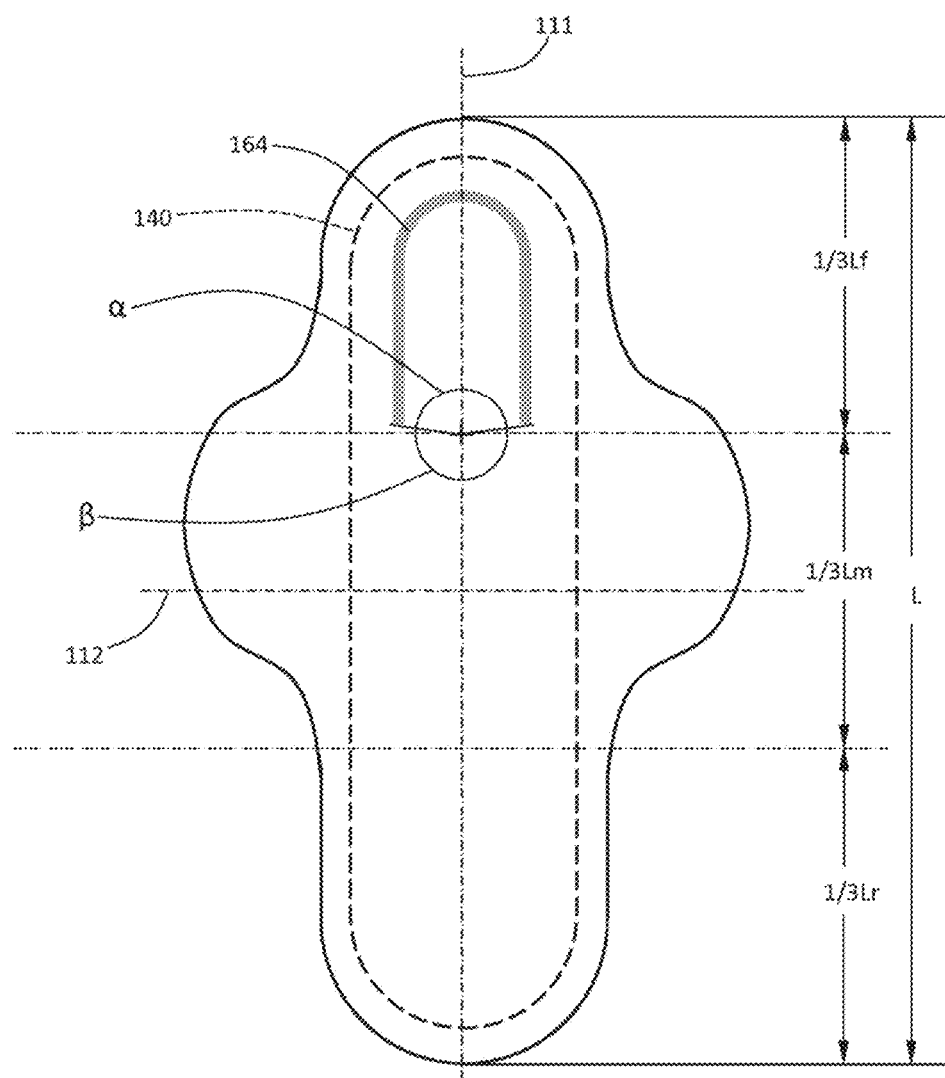
Figure 24E:
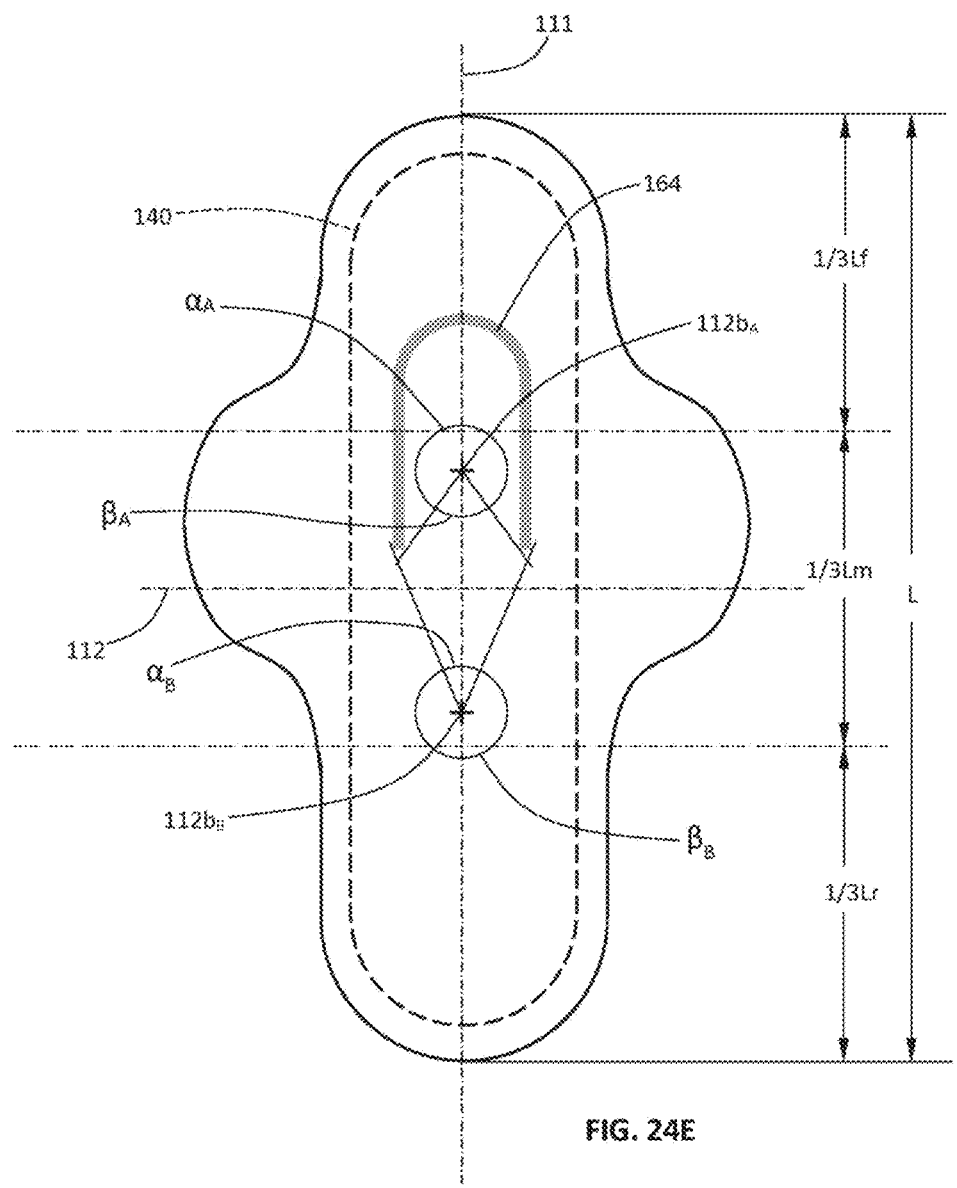

An example of a configuration of channel portion(s) 164 that does not predominately circumscribe a discharge locus is illustrated in FIG. 24D. The configuration shown in FIG. 24D does not predominately circumscribe a discharge locus because no discharge locus can be identified within the middle third (⅓Lm) of length L, where angle $\alpha$ is greater than angle $\beta$. In the example illustrated in FIG. 24D, even when a possible discharge locus is identified at the very edge of middle third (⅓Lm) of length L as shown, angle $\alpha$ is less than angle $\beta$. (In the example depicted in FIG. 24D, angle $\alpha$ is less than 180 degrees.)

From the foregoing description and from the associated figures, it will be appreciated that absence of a discharge locus within the middle third of the length of the pad, that is predominately circumscribed by a configuration of channel portion(s) 164, makes it less likely that a configuration of channel portion(s) 164 will be positioned to capture, channel, promote absorption of, and thereby help prevent migration of discharged fluid outwardly toward an edge of the topsheet.

Other non-limiting examples of configurations of channel portion(s) 164 are illustrated in FIGS. 23A-K, which are proportional as shown, and as shown, would predominately circumscribe a discharge locus located within the middle third of the length of a pad.

It may be desired that channel portion(s) 164 overlie the absorbent structure 140 of the article (in the z-direction), and preferably, be present only in locations on the topsheet overlying the absorbent structure. This is to ensure that any fluid channeled by channel portion(s) 164 is channeled along locations on the topsheet that are underlaid in the z-direction by the absorbent structure, such that channel portion(s) 164 are suitably disposed to facilitate absorption by the underlying absorbent structure 140, through the bottom(s) of the channel portion(s) 164.

Referring again to FIGS. 8-10, it can be seen that channel portions 164 are portions of the section of formed nonwoven web material forming topsheet 120 in which filaments 122 forming portions of the formed nonwoven web material are present in substantially lesser quantity than in built-up regions 166. The respective channel portions 164 and adjacent built-up regions 166 in a nonwoven web material may be formed by a process described below.

Figure 9:
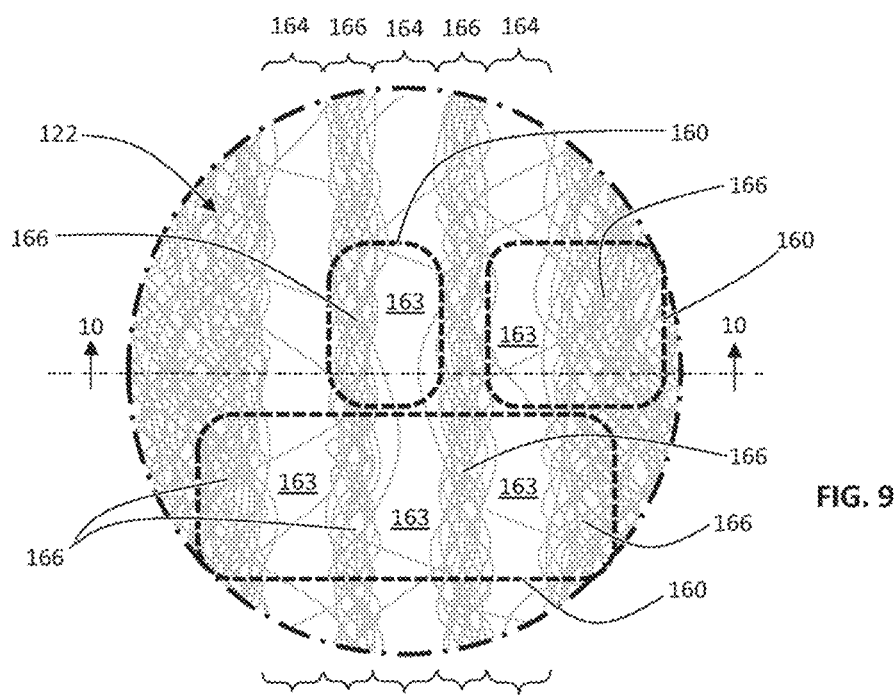
FIG. 9 is an expanded schematic view of the portion of the topsheet identified as "9" in FIG. 6.
Figure 10:
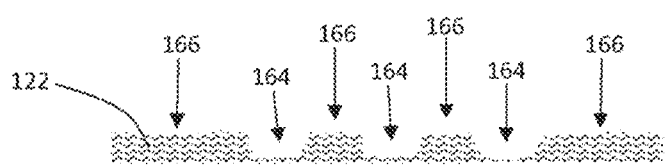
FIG. 10 is a schematic lateral cross section of the portion of the topsheet shown in FIG. 9.

Referring to FIG. 9, any number of zones 160 may be identified. Each zone includes at least one attenuated region 163 having a relatively substantially lesser fiber and/or filament area density adjacent to at least one built-up region 166 having a relatively substantially greater fiber and/or filament area density. Corresponding to the relatively lesser fiber and/or filament area density of the attenuated regions 163 and relatively greater fiber and/or filament area density of the built-up regions 166, attenuated regions 163 may have a relatively lower basis weight than adjacent built-up regions 166. The nonwoven web material may be manufactured as described below, such that these differences between adjacent regions 163, 166 within a zone 160 may be visually discernible. Visual discernibility of these regions and zones may be manifest in visible localized differences/variations in filament and/or fiber area density, web thickness/caliper and/or web transparency/opacity. For example, a viewer may perceive channel portions 164 in a section of formed nonwoven web material forming a topsheet 120 to be channels or grooves following oval-shaped paths along the surface of the topsheet 120, wherein the channels or grooves are visually discernible as regions of visually, discernibly lower filament and/or fiber area density, visually, discernibly lower web thickness/caliper and or visually, discernibly lower web opacity (conversely, higher translucency). In order to substantially ensure or enhance visual discernibility as well as the other functional aspects of the topsheet features described herein, it may be desired to control the filament deposition process and distribution between attenuated regions 163 and built-up regions 166, such that they differ in average basis weight by at least a factor of 2. As discussed below, distribution of filaments between attenuated regions and built-up regions may be controlled by selection of a substrate forming belt material for a given air permeability, and by control of the airflow drawing rate of the forming vacuum system.

Such channels or grooves may serve esthetic/decorative and functional purposes. A user/consumer of a feminine hygiene pad product having such features may perceive visible channels/grooves (with built-up regions therebetween and/or surrounding them) to serve a containment function by providing physical barriers to flow of exudate fluids across the surface of the pad and off the side(s) or end(s) thereof. In some configurations the combination of such channel portions with built-up regions therebetween or surrounding them may actually serve such a barrier function. The channel portions 164 may literally constitute channels in and along which exudate fluids may more freely collect and flow, while the surrounding built-up regions 166 may constitute physical barriers tending to inhibit fluid in the channels from flowing longitudinally or laterally outward toward the edge (outer perimeter 128) of the pad. This may be particularly true when filaments and/or fibers forming the pad have been spun from polymer resins (without or with hydrophobicity-enhancing melt additives) having hydrophobic surface energy properties, which can inhibit flow of aqueous fluids along their surfaces.

It will be appreciated that configurations of channel portions 164 such as those non-limiting examples described above and illustrated in FIGS. 6 and 23A-23K may provide visual appeal and liquid containment functionality not only to topsheets for feminine hygiene pads, but also to topsheets for adult incontinence pads, disposable absorbent pants and disposable diapers.

Referring to FIGS. 6-8, a section of formed nonwoven web material forming topsheet 120 of a feminine hygiene pad or adult incontinence pad may include one or more attenuated regions 163 defining hinge portions 168 formed therein, proximate to wing fold lines 115. Hinge portions 168 may extend approximately longitudinally along any portion, or substantially all, of the longitudinal length of wing portions 114 where they extend away from the main (central) portion of the pad. Hinge portions 168 may be formed in a manner similar to the manner in which channel portions 164 may be formed, as will be described below. Like channel portions 164, hinge portions 168 may be adapted to be visually discernible, and may include visually discernible attenuated regions of comparatively lesser filament and/or fiber area density and basis weight, adjacent visually discernible built-up regions of comparatively greater filament and/or fiber area density and basis weight, within visually discernible zones. Because they are arranged longitudinally proximate to line(s) 115 along which wing portions are desirably folded to wrap about the crotch portion of underpants, and because they may constitute areas of visibly reduced presence of filaments and/or fibers and/or visibly reduced topsheet thickness/caliper, hinge portions 168 may serve to visually indicate a folding location. Additionally, the reduced number of filaments and/or fibers in hinge portions 168 causes the web material therealong to be less stiff than the surrounding built-up regions 166, functionally promoting and facilitating folding along the hinge portions.

Figure 25:
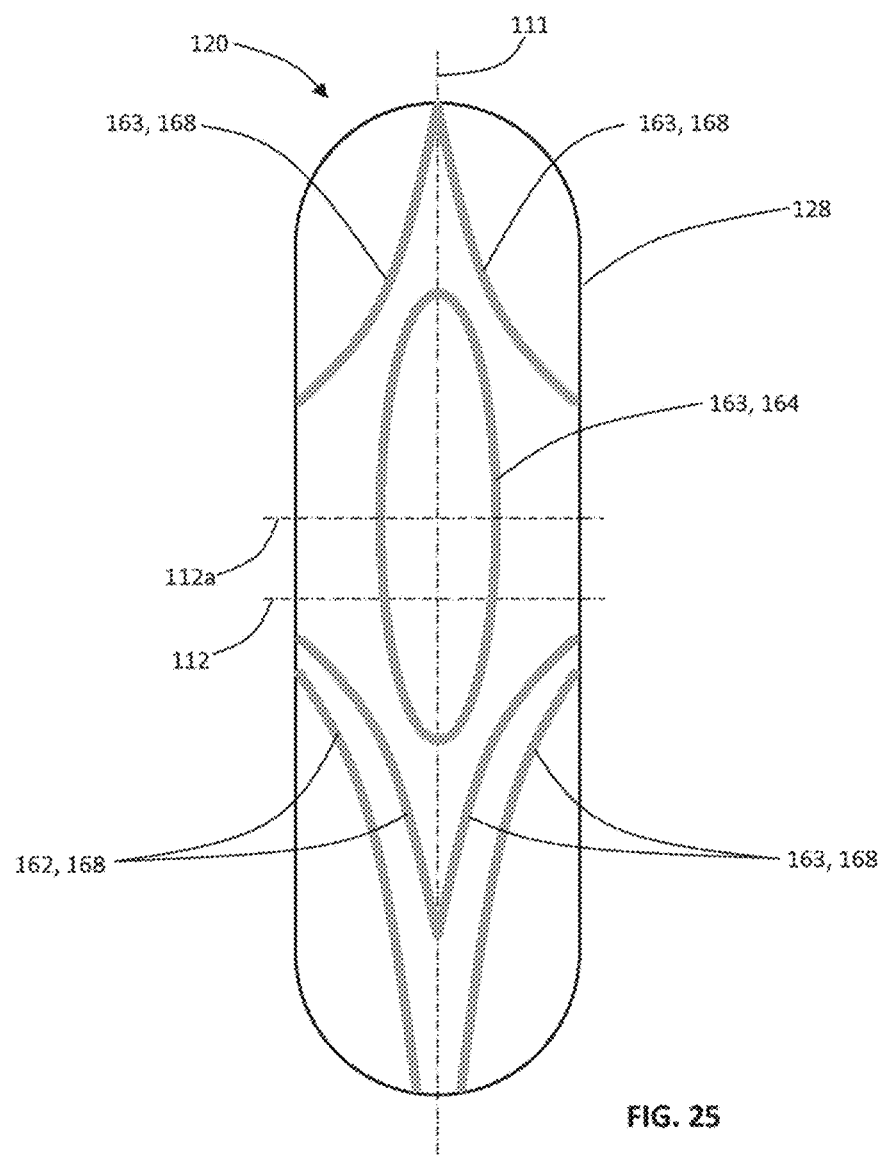
FIG. 25 is a plan view of an example of a topsheet with a configuration of channel portions and hinge portions.

In addition or as an alternative to providing hinge structures for wings, configurations of hinge portions 168 may be located along other portions of the topsheet to enhance flexibility, comfort and/or body conformity. Referring to FIG. 25, by way of non-limiting example, hinge portions 168 may be included to provide lines or paths along which the corners of the pad are enabled to more easily flex, to allow the pad to better and/or more comfortably conform to the user/wearer's body during wear.

It will be appreciated that a characteristic of a hinge portion 168 may be that it follows or parallels a path or line that extends between two edges of the topsheet where it defines wings 114, and one or more attenuated regions 163 occupy the majority of such path and form the hinge portion 168.

Other Ordered Arrangements

Figure 18:
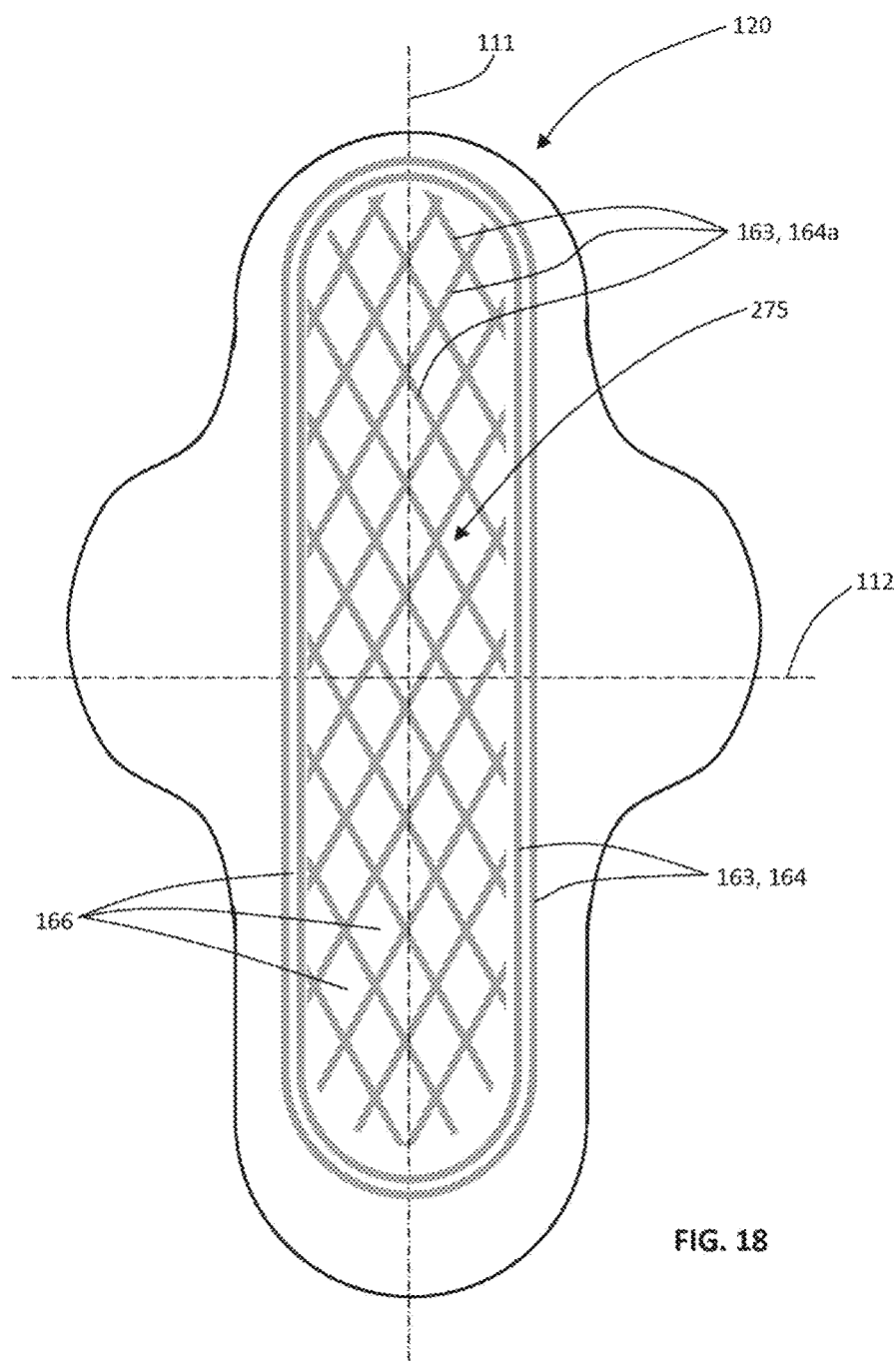
FIGS. 18 and 19 are schematic plan views of examples of topsheets having additional examples of features formed according to the processes described herein.
Figure 19:
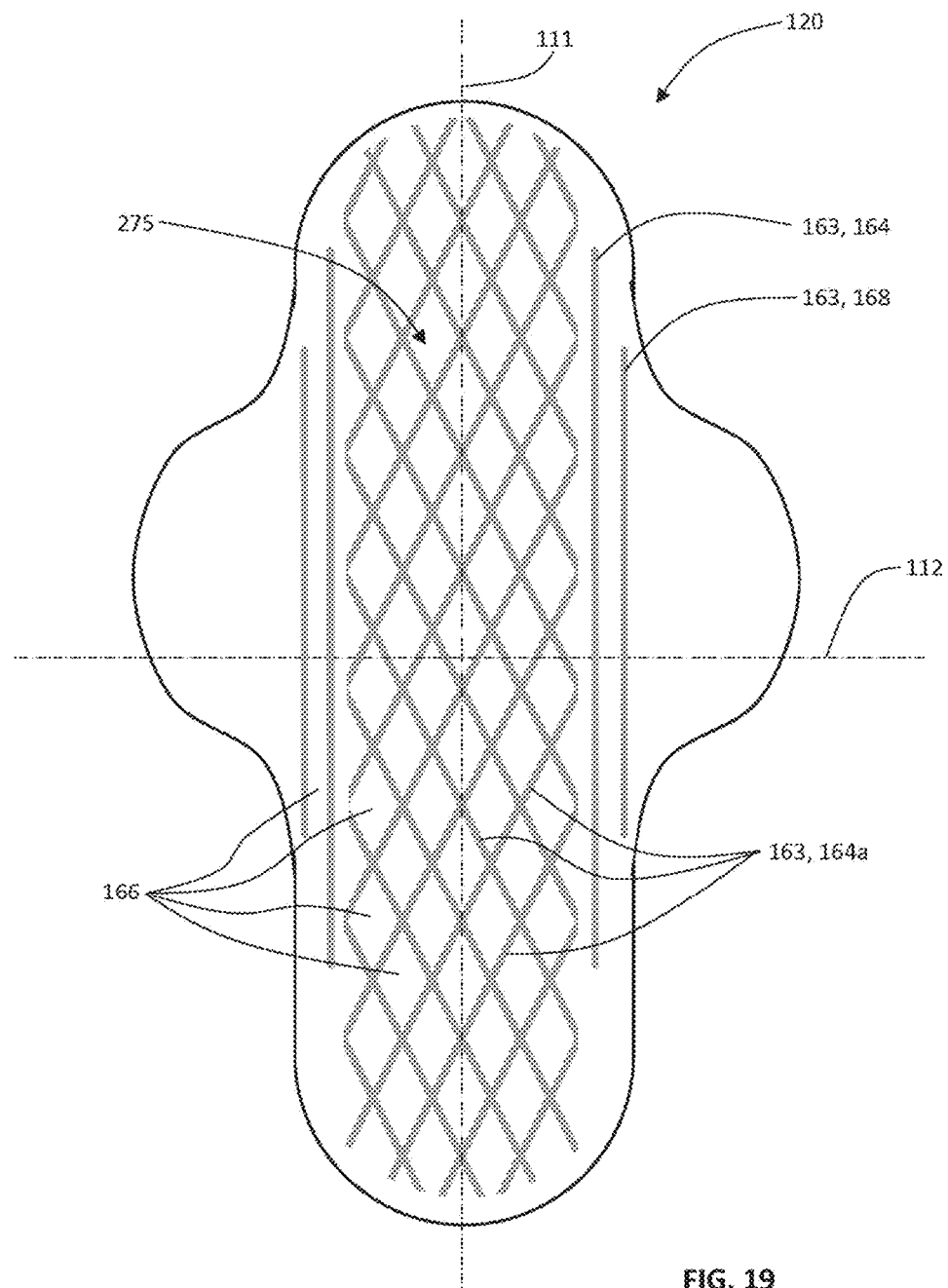

An advantage provided by the forming belt manufacturing technique described below and in the references incorporated by reference in the present disclosure, however, is that airflow blocking structures 262 may be formed and configured on a forming belt 260 according to an unlimited number of variants of desired combinations of recognizable, visually discernible shapes, images of natural or artificial objects, people, animals, fanciful characters, anthropomorphic characters, decorative elements, functional features, designs, patterns, sizes, spacings etc., by simply printing the negative of the desired configuration on the mask used to selectively block resin-curing light, as described below. It will be appreciated, therefore, that in addition to forming airflow blocking structures to impart the channel portions 164 and hinge portions 168 to a nonwoven web material formed on a forming belt as described herein, the airflow blocking structures may be designed and included on a forming belt to impart other functional features, decorative/ornamental features, or a combination thereof, to the nonwoven web material. FIGS. 18 and 19 illustrate two possible, non-limiting examples. In the examples shown in FIGS. 18 and 19, a pattern 275 of continuous low bulk portions 164a formed of attenuated region(s) 163, and defining a pattern of diamond-shaped built-up regions 166, may be formed on a section of formed nonwoven web material to form a feminine hygiene pad topsheet, in combination with one or more channel portions 164 and/or hinge portions 168. It will be appreciated that a pattern such as pattern 275 may be desired for functional and/or decorative purposes. In the examples depicted in FIGS. 18 and 19, pattern 275 of low bulk portions 164a may serve both purposes, by imparting a visually pleasing decorative appearance to the topsheet, and by providing a network of channel-like structures that may function as fluid channels in a manner similar to the channel portions 164 as described above, serving to help distribute flows of body exudate fluid across the pad surface area and drain them to underlying absorbent structure, while built-up regions 166 may serve to maintain separation between the channel-like structures' lower z-direction depths (and exudate fluid they carry) from the wearer's skin. Pattern 275 of low bulk portions 164a may be imparted by use of a forming belt with a suitable corresponding pattern of airflow blocking structures formed thereon, in the manner described below. As suggested by FIGS. 18 and 19, it may be desired in some circumstances that any pattern 275 configuration of continuous low bulk portions does not include portions that extend beyond the edges of the absorbent structure, or alternatively, to the edges of the topsheet, so as to avoid channeling exudate fluids to positions at which they may be unlikely to be absorbed by the absorbent structure, and/or might flow off the edges of the pad.

An unlimited number of other patterns 275 of attenuated regions and built-up regions are possible. As reflected in the additional non-limiting examples of FIGS. 26A, 26B and 27, it may be desired in some circumstances for a topsheet in its longitudinally and laterally central areas to include a pattern 275 of discrete low bulk portions 165 which, rather than being continuous across a substantial portion of the length or width of the topsheet in the manner of channel portions, and rather than intersecting or interconnecting with other low bulk portions 164a as suggested in FIGS. 18 and 19, are each discrete and entirely surrounded by a continuous area of built-up region 166, like "islands" (corresponding with low bulk portions 165) in a "sea" (corresponding with built-up region 166). A pattern of such discrete low bulk portions 165, without any traversing channel portions, may be included and may occupy a central area of the topsheet proximate a discharge locus and/or at the intersection of the longitudinal and lateral axes 111, 112. Non-limiting examples of such patterns are depicted in FIGS. 26A and 26B, appearing in the laterally central portions of the images and extending from top to bottom. In such examples each discrete low bulk portion 165, being relatively sparsely populated by filaments, can better serve as a pathway for fluid to move in a z-direction through the topsheet (behaving in a manner akin to a drain hole through the topsheet), while the surrounding, continuous built-up region 166 can serve as a barrier to inhibit x-y-direction lateral/longitudinal flow and thereby inhibit spreading of discharged fluid across the topsheet. These effects may be enhanced by manipulation of the hydrophobic/hydrophilic characteristics of various surfaces, portions and/or regions of the web from which the topsheet is made, through the techniques, materials and configurations described below. It has been learned that, generally, consumers/users of feminine hygiene pads prefer pads configured such that discharged menstrual fluid effectively moves suitably rapidly through the topsheet in a z-direction to absorbent material beneath, such that the x-y dimensions of staining of the topsheet by received fluid are as small as possible and centralized about the discharge locus. This visual signal indicates to the user that the absorbent system is working effectively to receive, capture and contain discharged fluid. Thus, a pattern of low bulk portions 164a such as depicted by way of non-limiting examples in FIGS. 26A and 26B, that does not include continuous channels such as depicted in FIGS. 18 and 19 at the intersection of the lateral and longitudinal axes and/or proximate the expected discharge locus 112b on the topsheet, may be preferred. Without intending to be bound by theory, it is believed that a pattern of discrete low bulk portions 165 occupying a total area (such as an area that is predominately circumscribed by one or more channel portions 164), is most effective at draining fluid in a z-direction when the discrete low bulk portions 165 occupy a fraction of the total area occupied by the pattern of 5 percent to 30 percent, more preferably 8 percent to 25 percent, and even more preferably 10 percent to 22 percent, of the total area occupied by the pattern.

For purposes herein, the percent fraction of the total area occupied by discrete low bulk portions reflects, and may be determined by, measurement of the corresponding area of the airflow blocked regions 264 in the x-y plane on the forming belt 260 used to form the topsheet material (described below), which, in turn, may also be reflected by corresponding resin curing regions 264a and/or resin non-curing regions 263a on a mask used to make the forming belt (according to the manufacturing method described below). Additionally, the percent fraction of a total area occupied by a pattern of discrete low bulk portions 165 may be measured directly from the topsheet web itself using a Pattern Analysis Test as described in either of U.S. Provisional Application Ser. Nos. 62/842,792 and 62/842,807. Where a range for percent fraction of a total area occupied by a pattern of discrete low bulk portions 165 is specified and/or recited in a claim herein, it is intended to apply to and cover such range as may be determined by any of the methods identified in this paragraph. If a Pattern Analysis Test set forth in one of the applications referenced above is found to be insufficient to measure such percent fraction under particular circumstances, resort to one of the other methods (e.g. measurement of area of airflow blocked regions 264 on forming belt, or measurement of area of resin curing regions 264a and/or resin non-curing regions 263a on a mask) may be had.

Figure 22:
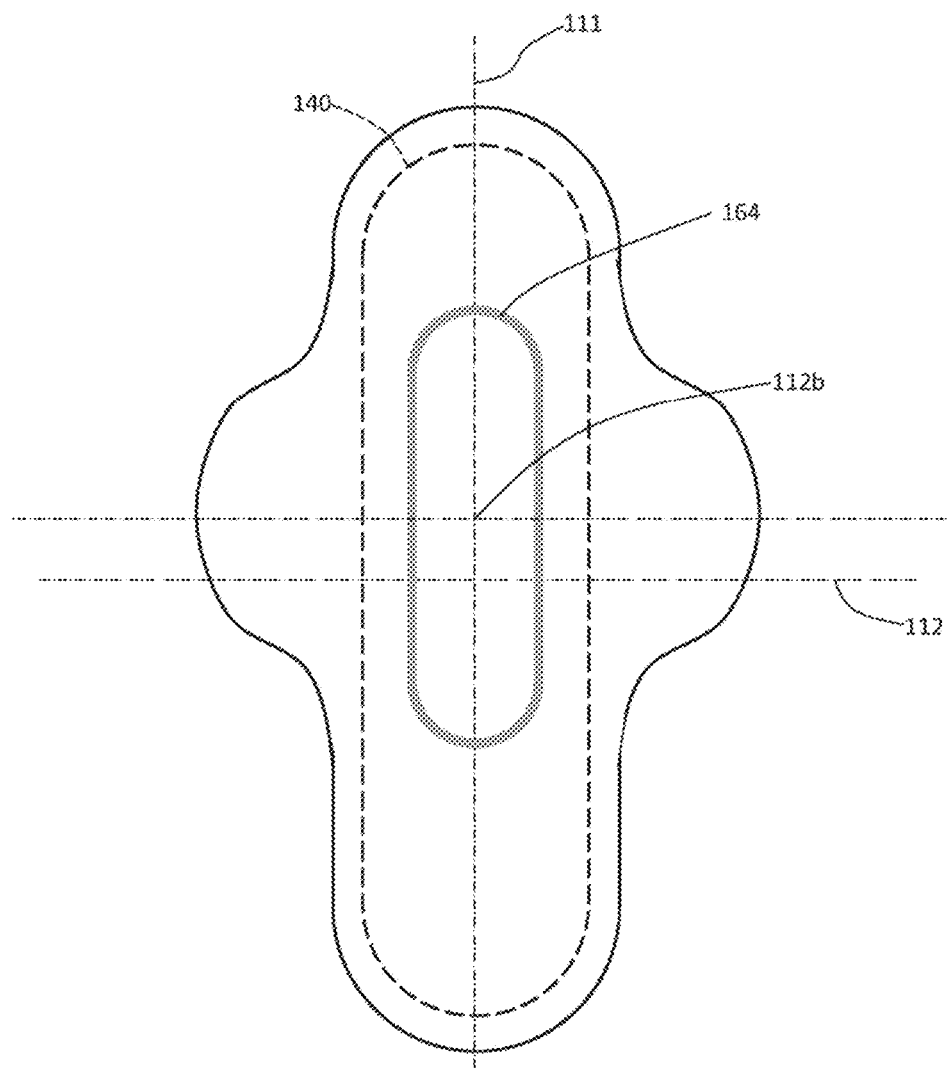
FIG. 22 is a plan view of an example of a feminine hygiene pad with a configuration of a channel portion.
Figure 23A:
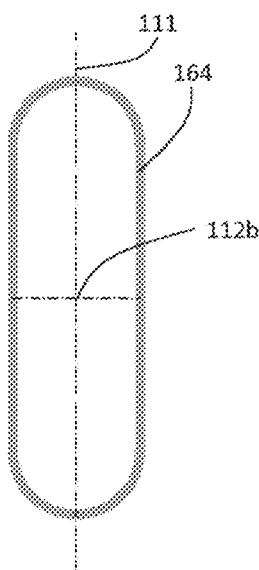
FIGS. 23A-23K are plan views of examples of configurations of channel portions for a topsheet.
Figure 23B:
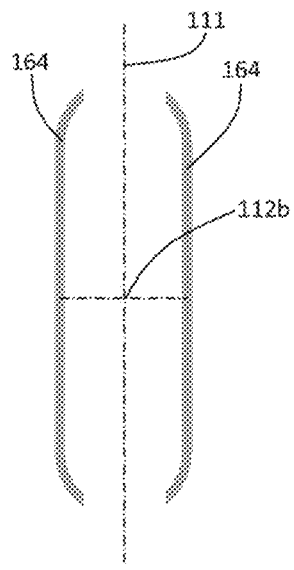
Figure 23C:
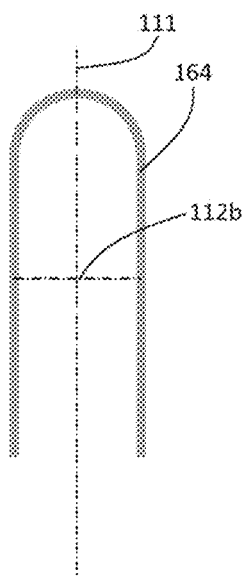
Figure 23D:
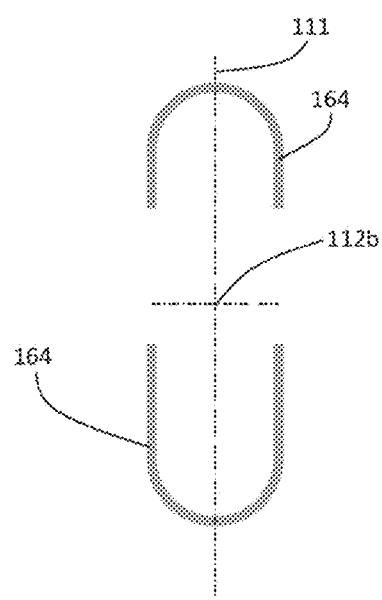
Figure 23E:
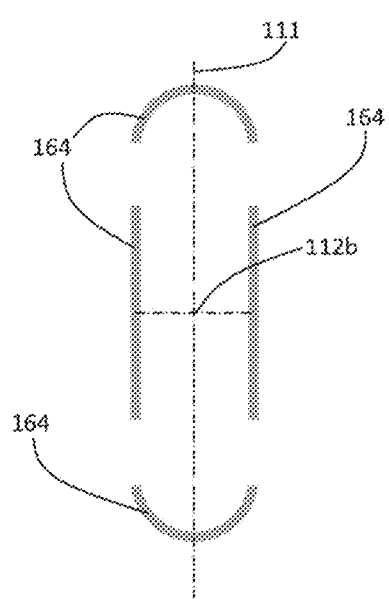
Figure 23F:
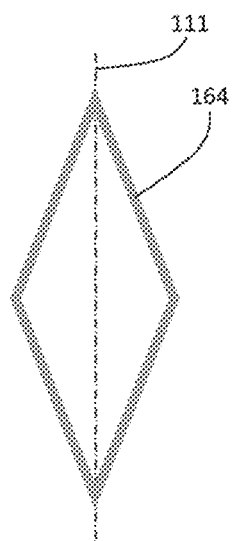
Figure 23G:
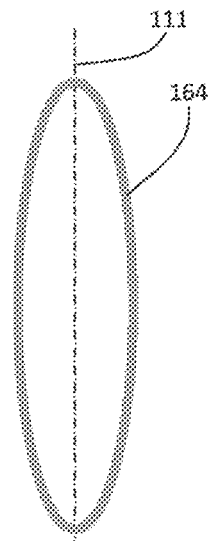
Figure 23H:
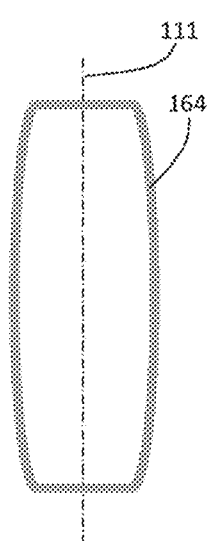
Figure 23I:
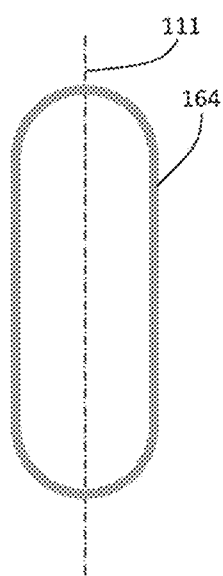
Figure 23J:
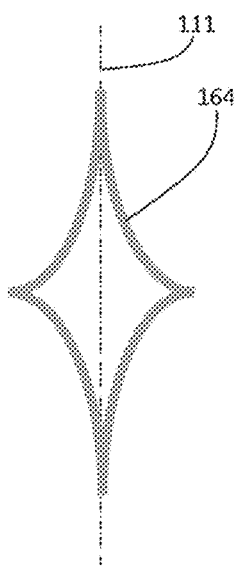
Figure 23K:
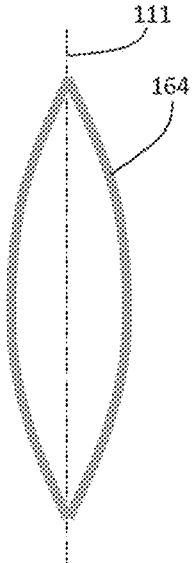

By way of particular, non-limiting example, referring to FIG. 22, if the total area circumscribed by channel portion 164 is occupied by a pattern of discrete low bulk portions collectively occupying 8 percent to 22 percent of the area occupied by the pattern, it is believed that optimal z-direction fluid draining effect may be achieved for the topsheet configuration.

In addition to controlling the area collectively occupied by discrete low bulk portions in a pattern thereof, their individual sizes may be regulated (via design of the forming belt 260, as described below) for beneficial effect. If a majority or all of the discrete low bulk portions 165 in the pattern each have an area of at least 0.8 mm$^2$ and no greater than 20 mm$^2$, more preferably no greater than 7 mm$^2$, user perceptions of tactile softness of the topsheet may be enhanced, while chances of exposure of the user's skin to the wet absorbent structure will be minimized while still maintaining optimal draining performance and control of stain spreading. (When the discrete low bulk portions have a circular shape, the ranges set forth immediately above equate with a low bulk portion diameter of at least 1 mm and no greater than 5 mm, more preferably no greater than 3 mm.)

As suggested in FIGS. 26A, 26B and 27, a pattern 275 of discrete low bulk portions 165 occupying longitudinally and/or laterally central portions of the topsheet of may be partially or entirely surrounded by one or more channel portions 164. One or more channel portions 164 may be configured to predominately circumscribe a discharge locus 112b and otherwise function as described above. A pattern of low bulk portions present proximate and/or about the intersection of the lateral and longitudinal axes and/or at the expected discharge locus 112b on the topsheet may be included within any of the configurations of channel portions 164 described herein, and illustrated by way of non-limiting example in FIGS. 6, 22, 23A-23K, 24A, 24B, 24C, 24E and 25.

As will be apparent from the description below, the method and process of formation of the web material will result in "sidedness," wherein one x-y surface of the formed web material exhibits a substantially greater visible topography with visible z-direction "heights" of well-defined built-up regions (on the side most proximate the forming belt during formation—forming belt side), than does the opposing x-y surface (opposite side). This sidedness makes it desirable that, when the web material is used to form a topsheet, the forming belt side faces the wearer on the end product. This makes the topography more visible to the wearer, may enhance visual and tactile softness signals conveyed by the topographical features, and facilitates the functionality of the topsheet as described herein.

Absorbent Structure

The absorbent structure 140 as contemplated herein may have any suitable x-y plane perimeter shape including but not limited to an oval shape, a stadium shape, a rectangle shape, an asymmetric shape, and an hourglass shape. In some examples, the absorbent structure 140 may be imparted with a contoured shape, e.g. narrower in an intermediate region than in the forward and rearward end regions. In other examples, the absorbent structure may have a tapered shape having a wider portion in one end region of the pad which tapers to a narrower end region in the other end region of the pad. The absorbent structure 140 may stiffness that varies along one or both the longitudinal and lateral directions.

The absorbent structure 140 may have one or more layers. In certain embodiments, there are two absorbent layers where there is a first absorbent layer and a second absorbent layer adjacent to the first absorbent layer. These materials are preferably compressible, conformable, non-irritating to the wearer's skin, and capable of absorbing and retaining liquids such as urine and other certain body exudates including menses.

The first absorbent layer may include a first layer of absorbent material, which may be 100% or less of particles of superabsorbent polymer (SAP) (also known as absorbent gelling material or AGM), such as 85% to 100% SAP, 90% to 100% SAP, or even 95% to 100% SAP, specifically including all 0.5% increments within the specified ranges and all ranges formed therein or thereby. The second absorbent layer may include a second layer of absorbent material, which may also be 100% or less of SAP (including the ranges specified above). Alternatively, either or both the first and second absorbent layer may include a combination of cellulose, commuted wood pulp, or the like, in combination with SAP. In some examples, the absorbent structure may include a first layer and a second layer, wherein the first layer is designed primarily for absorbing and retaining fluid (sometimes known as a storage layer). The storage layer may include particles of SAP and may include particles of SAP distributed within a batt of cellulosic fiber. The second layer (sometimes known as an acquisition/distribution layer or "secondary topsheet") may be designed to be disposed directly beneath the topsheet and configured for receiving and dispersing energy from a gush of fluid, and distributing the fluid across and down to the storage layer. The acquisition/distribution layer may be a batt or nonwoven structure of filaments or fibers which may be partially or entirely cellulosic fibers, or a blend of cellulosic fibers and polymeric fibers or filaments. In particular examples the acquisition/distribution layer may be an airlaid batt of cellulosic fibers.

Alternatively, the absorbent structure may be formed entirely/solely of cellulosic fiber (including cellulosic fiber material known as "airfelt") as the absorbent material.

The absorbent structure 140 may also comprise a carrier layer for either or both of first and second absorbent layers. This carrier layer may be a nonwoven web, which may be apertured. The absorbent structure 140 may also include a thermoplastic adhesive material at least partially bonding a layer of the absorbent material to a substrate material.

The absorbent structure 140 may include one or more grooves, channels or pockets that are defined by z-direction depressions or changes in caliper of layer(s) of the absorbent structure. The one or more grooves, channels or pockets may be provided in addition to one or more channels or instead of the one or more channels in the topsheet. The pockets may be areas in the absorbent structure that are free of, or substantially free of absorbent material, such as SAP (including the ranges specified above). Other forms and more details regarding channels and pockets that are free of, or substantially free of absorbent materials, such as SAP, within absorbent structures are discussed in greater detail in US 2014/0163500; US 2014/0163506; and US 2014/0163511.

The configuration and construction of the absorbent structure 140 may vary (e.g., the absorbent structure 140 may have varying caliper zones, a hydrophilic gradient, a superabsorbent gradient, or lower average density and lower average basis weight acquisition zones). Further, the size and absorbent capacity of the absorbent structure 140 may also be varied to accommodate a variety of wearers. However, the total absorbent capacity of the absorbent structure 140 should be compatible with the design loading and the intended use of the sanitary napkin or any other disposable absorbent article.

In some forms contemplated herein, the absorbent structure 140 may comprise a plurality of multi-functional layers in addition to the first and second absorbent layers. For example, the absorbent structure 140 may comprise a core wrap (not shown) useful for enveloping the first and second absorbent layers and other optional layers. The core wrap may be formed by two nonwoven materials, substrates, laminates, films, or other materials. The core wrap may only comprise a single material, substrate, laminate, or other material wrapped at least partially around itself.

The absorbent structure 140 may comprise one or more adhesives, for example, to help immobilize any superabsorbent gelling material or other absorbent materials that might be present in the core.

Absorbent structures comprising relatively high amounts of SAP with various core designs are disclosed in U.S. Pat. No. 5,599,335; EP 1 447 066; WO 95/11652; US 2008/0312622A1; and WO 2012/052172. These designs may be used to configure the first and second superabsorbent layers. Alternate core embodiments are also described in U.S. Pat. Nos. 4,610,678; 4,673,402; 4,888,231; and 4,834,735. The absorbent structure may further comprise additional layers that mimic a dual core system containing an acquisition/distribution core of chemically stiffened fibers positioned over an absorbent storage core as described in U.S. Pat. No. 5,234,423 and in U.S. Pat. No. 5,147,345.

Superabsorbent polymers as contemplated herein are typically used in the form of discrete particles. Such superabsorbent polymer particles can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of fluid absorbent gelling material particles may also be used.

The size of the fluid absorbent gelling material particles may vary over a wide range. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Fluid absorbent gelling material particles preferably have a particle size of about 30 microns to about 2 mm for substantially all of the particles. "Particle Size" as used herein means the weighted average of the smallest dimension of the individual particles.

These layers are preferably substantially free of airfelt and are thus distinct from mixed layers that may include airfelt. As used herein, "substantially free of airfelt" means less than 5%, 3%, 1%, or even 0.5% of airfelt. In a preferred case, there will be no measurable airfelt in the superabsorbent layers of the absorbent structure. In the case of the first superabsorbent layer, it is preferably disposed onto the first distribution layer discontinuously. As used herein "discontinuously" or "in a discontinuous pattern" means that the superabsorbent polymers are applied onto the first distribution layer in a pattern of disconnected shaped areas. These areas of superabsorbent polymers or areas free of superabsorbent polymer may include, but are not limited to linear strips, non-linear strips, circles, rectangles, triangles, waves, mesh, and combinations thereof. The first superabsorbent layer like the second superabsorbent layer may, however, be disposed onto its respective distribution layer in a continuous pattern. As used herein "continuous pattern" or "continuously" means that the material is deposited and or secured to a superabsorbent carrier material and/or the adjacent distribution layer in an uninterrupted manner such that there is rather full coverage of the distribution layer by the superabsorbent polymer.

In some examples the absorbent structure 140 may be formed of or include a layer of absorbent open-celled foam material. In some examples, the foam material may include at least first and second sublayers of absorbent open-celled foam material, the sublayers being in direct face-to-face contact with each other. In such examples, the wearer-facing sublayer may be a relatively larger-celled foam material, and the outward-facing sublayer may be a relatively smaller-celled foam material, for purposes explained in more detail below.

The open-celled foam material may be a foam material that is manufactured via polymerization of the continuous oil phase of a water-in-oil high internal phase emulsion ("HIPE").

A water-in-oil HIPE has two phases. One phase is a continuous oil phase comprising monomers to be polymerized, and an emulsifier to help stabilize the HIPE. The oil phase may also include one or more photoinitiators. The monomer component may be included in an amount of about 80% to about 99%, and in certain examples from about 85% to about 95% by weight of the oil phase. The emulsifier component, which is soluble in the oil phase and suitable for forming a stable water-in-oil emulsion may be included in the oil phase in an amount of about 1% to about 20% by weight of the oil phase. The emulsion may be formed at an emulsification temperature of about 20° C. to about 130° C. and in certain examples from about 50° C. to about 100° C.

In general, the monomers will may be included in an amount of about 20% to about 97% by weight of the oil phase and may include at least one substantially water-insoluble monofunctional alkyl acrylate or alkyl methacrylate. For example, monomers of this type may include C4-C18 alkyl acrylates and C2-C18 methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also include from about 2% to about 40%, and in certain examples from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type comprise monomers containing two or more activated acrylate, methacrylate groups, or combinations thereof. Non-limiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of about 0% to about 15% by weight of the oil phase, in certain examples from about 2% to about 8%, to modify properties of the HIPE foams. In certain cases, "toughening" monomers may be desired to impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better-formed HIPE foam which results in greater toughness, tensile strength, abrasion resistance, and the like. Monomers may also be added to confer flame retardancy, as disclosed, for example, in U.S. Pat. No. 6,160,028. Monomers may be added to impart color (for example vinyl ferrocene); to impart fluorescent properties; to impart radiation resistance; to impart opacity to radiation (for example lead tetraacrylate); to disperse charge; to reflect incident infrared light; to absorb radio waves; to make surfaces of the HIPE foam struts or cell walls wettable; or for any other desired property in a HIPE foam. In some cases, these additional monomers may slow the overall process of conversion of HIPE to HIPE foam, the tradeoff being necessary if the desired property is to be conferred. Thus, such monomers can also be used to slow down the polymerization rate of a HIPE. Examples of monomers of this type comprise styrene and vinyl chloride.

The oil phase may further include an emulsifier to stabilize the HIPE. Emulsifiers used in a HIPE can include: (a) sorbitan monoesters of branched C16-C24 fatty acids; linear unsaturated C16-C22 fatty acids; and linear saturated C12-C14 fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of-branched C16-C24 fatty acids, linear unsaturated C16-C22 fatty acids, or linear saturated C12-C14 fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of-branched C16-C24 alcohols, linear unsaturated C16-C22 alcohols, and linear saturated C12-C14 alcohols, and mixtures of these emulsifiers. See U.S. Pat. Nos. 5,287,207 and 5,500,451. Another emulsifier that may be used is polyglycerol succinate (PGS), which is formed from an alkyl succinate, glycerol, and triglycerol.

Such emulsifiers, and combinations thereof, may be added to the oil phase so that they constitute about 1% to about 20%, in certain examples about 2% to about 15%, and in certain other examples about 3% to about 12%, of the weight of the oil phase. In certain examples, coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain C12-C22 dialiphatic quaternary ammonium salts, short chain C1-C4 dialiphatic quaternary ammonium salts, long chain C12-C22 dialkoyl(alkenoyl)-2-hydroxyethyl, short chain C1-C4 dialiphatic quaternary ammonium salts, long chain C12-C22 dialiphatic imidazolinium quaternary ammonium salts, short chain C1-C4 dialiphatic imidazolinium quaternary ammonium salts, long chain C12-C22 monoaliphatic benzyl quaternary ammonium salts, long chain C12-C22 dialkoyl(alkenoyl)-2-aminoethyl, short chain C1-C4 monoaliphatic benzyl quaternary ammonium salts, short chain C1-C4 monohydroxyaliphatic quaternary ammonium salts. In certain examples, ditallow dimethyl ammonium methyl sulfate (DTDMAMS) may be used as a coemulsifier.

Any photoinitiators included may be included at between about 0.05% and about 10%, and in some examples between about 0.2% and about 10% by weight of the oil phase. Lower amounts of photoinitiator allow light to better penetrate the HIPE foam, which can provide for polymerization deeper into the HIPE foam. However, if polymerization is performed in an oxygen-containing environment, it may be desired that there be enough photoinitiator present to initiate the polymerization and overcome oxygen inhibition. Photoinitiators can respond rapidly and efficiently to a light source with the production of radicals, cations, and other species that are capable of initiating a polymerization reaction. Photoinitiators selected for use in forming foams within contemplation of the present disclosure may absorb UV light at wavelengths of about 200 nanometers (nm) to about 800 nm, in certain examples about 250 nm to about 450 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine]oxide in combination with 2-hydroxy-2-methyl-1-phenylpropan-1-one (50:50 blend of the two is sold by Ciba Specialty Chemicals, Ludwigshafen, Germany as DAROCUR 4265); benzyl dimethyl ketal (sold by Ciba Geigy as IRGACURE 651); α-,α-dimethoxy-α-hydroxy acetophenone (sold by Ciba Specialty Chemicals as DAROCUR 1173); 2-methyl-1-[4-(methyl thio)phenyl]-2-morpholino-propan-1-one (sold by Ciba Specialty Chemicals as IRGACURE 907); 1-hydroxy-cyclohexyl-phenyl ketone (sold by Ciba Specialty Chemicals as IRGACURE 184); bis(2,4,6-trimethylbenzoyl)-phenylphosphineoxide (sold by Ciba Specialty Chemicals as IRGACURE 819); diethoxyacetophenone, and 4-(2-hydroxyethoxy)phenyl-(2-hydroxy-2-methylpropyl)ketone (sold by Ciba Specialty Chemicals as IRGACURE 2959); and Oligo [2-hydroxy-2-methyl-1-[4-(1-methylvinyl)phenyl]propanone] (sold by Lamberti spa, Gallarate, Italy as ESACURE KIP EM.

The dispersed aqueous phase of a HIPE comprises water, and may also comprise one or more components, such as initiator, photoinitiator, or electrolyte, wherein in certain examples, the one or more components are at least partially water soluble.

One component included in the aqueous phase may be a water-soluble electrolyte. The water phase may contain from about 0.2% to about 40%, in certain examples from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte can include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be included in the aqueous phase is a water-soluble free-radical initiator. The initiator can be present at up to about 20 mole percent based on the total moles of polymerizable monomers present in the oil phase. In certain examples, the initiator may be included in an amount of about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, azo initiators, redox couples like persulfate-bisulfate, persulfate-ascorbic acid, and other suitable redox initiators. In certain examples, to reduce the potential for premature polymerization which may clog the emulsification system, addition of the initiator to the monomer phase may be performed near the end of the emulsification step, or shortly afterward.

Photoinitiator, if included in the aqueous phase, may be at least partially water soluble, and may constitute between about 0.05% and about 10%, and in certain examples between about 0.2% and about 10%, by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. Photoinitiators selected for use to form foams within contemplation of the present disclosure may absorb UV light at wavelengths of about 200 nanometers (nm) to about 800 nm, in certain examples from about 200 nm to about 350 nm, and in certain examples from about 350 nm to about 450 nm. If a photoinitiator is to be included in the aqueous phase, suitable types of water-soluble photoinitiators may include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane]disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis(2-methylpropionamidine)dihydrochloride; 2,2'-dicarboxymethoxydibenzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that can be used are listed in U.S. Pat. No. 4,824,765.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler particles, for example starch, titanium dioxide, carbon black, or calcium carbonate; fibers; chain transfer agents; odor absorbers, for example activated carbon particulates; dissolved polymers; dissolved oligomers; and the like.

HIPE foam is produced from the polymerization of the monomers comprising the continuous oil phase of a HIPE. In certain examples, a HIPE foam layer may have one or more sublayers, and may be either homogeneous or heterogeneous polymeric open-celled foams. Homogeneity and heterogeneity relate to distinct layers within the same HIPE foam, which are similar in the case of homogeneous HIPE foams and differ in the case of heterogeneous HIPE foams. A heterogeneous HIPE foam may contain at least two distinct sublayers that differ with regard to their chemical composition, physical properties, or both; for example, sublayers may differ with regard to one or more of foam density, polymer composition, specific surface area, or pore size (also referred to as cell size). For example, for a HIPE foam if the difference relates to pore size, the average pore size in the respective sublayers may differ by at least about 20%, in certain examples by at least about 35%, and in still other examples by at least about 50%. In another example, if the differences in the sublayers of a HIPE foam layer relate to density, the densities of the layers may differ by at least about 20%, in certain examples by at least about 35%, and in still other examples by at least about 50%. For instance, if one layer of a HIPE foam has a density of 0.020 g/cm$^3$, another layer may have a density of at least about 0.024 g/cm3 or less than about 0.016 g/cm3, in certain examples at least about 0.027 g/cm$^3$ or less than about 0.013 g/cm$^3$, and in still other examples at least about 0.030 g/cm$^3$ or less than about 0.010 g/cm$^3$. If the differences between the layers are related to the chemical composition of the HIPE or HIPE foam, the differences may reflect a relative amount difference in at least one monomer component, for example by at least about 20%, in certain examples by at least about 35%, and in still further examples by at least about 50%. For instance, if one sublayer of a HIPE or HIPE foam is composed of about 10% styrene in its formulation, another sublayer of the HIPE or HIPE foam may be composed of at least about 12%, and in certain examples of at least about 15%.

A HIPE foam layer structured to have distinct sublayers formed from differing HIPEs may provide a HIPE foam layer with a range of desired performance characteristics. For example, a HIPE foam layer comprising first and second foam sublayers, wherein the first foam sublayer has a relatively larger pore or cell size, than the second sublayer, when used in an absorbent article may more quickly absorb incoming fluids than the second sublayer. For example, when the HIPE foam layer is used to form an absorbent structure 140 of a feminine hygiene pad, the first foam sublayer may be layered over the second foam sublayer having relatively smaller pore sizes, as compared to the first foam sublayer, which exert more capillary pressure and draw the acquired fluid from the first foam sublayer, restoring the first foam sublayer's ability to acquire more fluid from above. HIPE foam pore sizes may range from 1 to 200 µm and in certain examples may be less than 100 µM. HIPE foam layers of the present disclosure having two major parallel surfaces may be from about 0.5 to about 10 mm thick, and in certain examples from about 2 to about 10 mm. The desired thickness of a HIPE foam layer will depend on the materials used to form the HIPE foam layer, the speed at which a HIPE is deposited on a belt, and the intended use of the resulting HIPE foam layer.

The HIPE foam layers of the present disclosure are preferably relatively open-celled. This refers to the individual cells or pores of the HIPE foam layer being in substantially unobstructed communication with adjoining cells. The cells in such substantially open-celled HIPE foam structures have intercellular openings or windows that are large enough to permit ready fluid transfer from one cell to another within the HIPE foam structure. For purpose of the present disclosure, a HIPE foam is considered "open-celled" if at least about 80% of the cells in the HIPE foam that are at least 1 µm in size are in fluid communication with at least one adjoining cell.

In addition to being open-celled, in certain examples HIPE foams are adapted to be sufficiently hydrophilic to permit the HIPE foam to absorb aqueous fluids. In some examples the internal surfaces of a HIPE foam may be rendered hydrophilic by residual hydrophilizing surfactants or salts left in the HIPE foam following polymerization, or by selected post-polymerization HIPE foam treatment procedures such as those as described in references cited herein.

In certain examples, for example when it is used to form an absorbent structure 140 of a feminine hygiene pad, a HIPE foam layer may be flexible and exhibit an appropriate glass transition temperature (Tg). The Tg represents the midpoint of the transition between the glassy and rubbery states of the polymer. In general, HIPE foams that have a Tg that is higher than the temperature of use can be strong but will also be relatively rigid and potentially prone to fracture (brittle). In certain examples, regions of the HIPE foams of the current disclosure which exhibit either a relatively high Tg or excessive brittleness will be discontinuous. Since these discontinuous regions will also generally exhibit high strength, they can be prepared at lower densities without compromising the overall strength of the HIPE foam.

HIPE foams intended for applications requiring flexibility should contain at least one continuous region having a Tg as low as possible, so long as the overall HIPE foam has acceptable strength at in-use temperatures. In certain examples, the Tg of this region will be less than about 40° C. for foams used at about ambient temperature conditions; in certain other examples Tg will be less than about 30° C. For HIPE foams used in applications wherein the use temperature is higher or lower than ambient temperature, the Tg of the continuous region may be no more than 10° C. greater than the use temperature, in certain examples the same as use temperature, and in further examples about 10° C. less than use temperature wherein flexibility is desired. Accordingly, monomers are selected as much as possible that provide corresponding polymers having lower Tg's.

HIPE foams useful for forming absorbent structures and/or sublayers within contemplation of the present disclosure, and materials and methods for their manufacture, also include but are not necessarily limited to those foams and methods described in U.S. Pat. Nos. 10,045,890; 9,056,412; 8,629,192; 8,257,787; 7,393,878; 6,551,295; 6,525,106; 6,550,960; 6,406,648; 6,376,565; 6,372,953; 6,369,121; 6,365,642; 6,207,724; 6,204,298; 6,158,144; 6,107,538; 6,107,356; 6,083,211; 6,013,589; 5,899,893; 5,873,869; 5,863,958; 5,849,805; 5,827,909; 5,827,253; 5,817,704; 5,817,081; 5,795,921; 5,741,581; 5,652,194; 5,650,222; 5,632,737; 5,563,179; 5,550,167; 5,500,451; 5,387,207; 5,352,711; U.S. Pat. Nos. 5,397,316; 5,331,015; 5,292,777; 5,268,224; 5,260,345; 5,250,576; 5,149,720; 5,147,345; and US 2005/0197414; US 2005/0197415; US 2011/0160326; US 2011/0159135; US 2011/0159206; US 2011/0160321; US 2011/0160689, and U.S. App. Ser. No. 62/804,864, which are incorporated herein by reference to the extent not inconsistent herewith.

An absorbent structure formed of HIPE foam may include one or more patterns of perforations therethrough, including at least a first pattern disposed within an expected discharge location overlying the intersection of longitudinal and lateral axes of the pad. Perforations may be punched, cut or otherwise formed through the entire z-direction depth of the HIPE foam absorbent structure, or only through a wearer-facing layer or partially into the wearer-facing portion thereof. When a HIPE foam absorbent structure is disposed in direct contact with a topsheet as described herein, with no intervening acquisition layer formed of another material, perforations therethrough may serve as a group of reservoirs to receive, temporarily hold, and aid in distributing rapid discharges of relatively small quantities of menstrual fluid, until the HIPE foam has sufficient time to distribute and absorb the fluid via capillary action. Additionally, such perforations help decrease bending stiffness of the absorbent structure, which may help increase comfort of the pad for the wearer. A pattern of perforations having an average radius or other largest dimension of 1.0 mm to 4.0 mm, and more preferably 1.5 mm to 3.5 mm may be included. The pattern may include perforations at a numerical density of 3.0 to 9.0 perforations per cm$^2$, and more preferably 4.0 to 8.0 perforations per cm$^2$. In selecting the appropriate average size, numerical density, and surface area occupied by the pattern of perforations, the manufacturer may wish to balance the volume of the "reservoirs" desired with the need to retain absorbent material in locations proximate to and about the expected discharge location. Additional details concerning configurations of such perforations in combination with examples of suitable absorbent structures may be found in U.S. Pat. No. 8,211,078.

An absorbent structure formed of HIPE foam should be imparted with sufficient size, capillarity and hydrophilicity to have capability to effectively draw discharged fluid from a topsheet over a time of use/wear of the pad during menstruation that is normal and expected for feminine hygiene pads, for example, from 4 to 8 hours. Thus, it may be desired that an absorbent structure 140 formed of HIPE foam have a caliper (prior to wetting) that provides satisfactory absorbency to a standard-sized pad. Of course, a relatively thick pad can be manufactured, but that is typically deemed undesirable for daytime use in view of desires for flexibility/pliability and thinness, for comfort and discreetness under clothing. The manufacture must balance these competing objectives. Accordingly a feminine hygiene pad with a HIPE foam absorbent structure as contemplated herein, it may be desired that the layer have a caliper in the majority of its wearer-facing surface area (prior to wetting) of 1 mm to 5 mm, or more preferably 1.5 mm to 3.5 mm, or even more preferably 2.0 mm to 3.0 mm. (The caliper of a HIPE foam layer may be measured visually, with assistance of magnification/microscopy and/or photography or any other facilitating techniques and equipment, to any extent deemed useful.) Where the absorbent structure 140 includes two sublayers as described herein, it may be desired that the upper sublayer have a caliper (prior to wetting) of 0.64 mm to 3.2 mm, or preferably 0.96 mm to 2.24 mm, or even more preferably 1.28 mm to 1.92 mm; and it may be desired that the lower sublayer have a caliper (prior to wetting) of 0.16 mm to 0.80 mm, or more preferably 0.24 mm to 0.56 mm, or even more preferably 0.32 mm to 0.48 mm.

In other examples, the absorbent structure may be a heterogeneous mass formed of a nonwoven layer of spun filaments, with discrete foam pieces within and interspersed/distributed through the nonwoven structure, the discrete foam pieces being formed about and enrobing portions of filaments. Examples of such an absorbent structure are described in U.S. Pat. Nos. 10,045,890; 10,016,779; 9,956,586; 9,993,836; 9,574,058; US 2015/0313770; US 2015/0335498; US 2015/0374876; US 2015/0374561; US 2016/0175787; US 2016/0287452; US 2017/0071795; US 2017/0119587; US 2017/0119596; US 2017/0119597; US 2017/0119588; US 2017/0119593; US 2017/0119594; US 2017/0119595; US 2017/0199598; US 2017/0267827; US 2018/0110660; US 2017/0119600; US 2017/0119589; US 2018/0169832; US 2018/0168884; and US 2018/0318150.

The absorbent structure may also include similar optional layers. They may be webs selected from the group consisting of a fibrous structure, an airlaid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown filaments, a coform web of staple fibers and melt blown filaments, and layered webs that are layered combinations thereof.

These optional layers of the core and of the chassis may include materials such as creped cellulose wadding, fluffed cellulose fibers, airlaid (airfelt), and textile fibers. The materials of the optional layers may also include filaments such as, for example, synthetic fibers or filaments, thermoplastic particulates, fibers or filaments, tricomponent filaments, and bicomponent fibers or filaments such as, for example, sheath/core filaments having, for example, any of the following polymer combinations: polyethylene/polypropylene, polyethylvinyl acetate/polypropylene, polyethylene/polyester, polypropylene/polyester, copolyester/polyester, and the like. The optional layers may include any combination of the materials listed above, copolymers thereof, and/or a plurality of the materials listed above, alone or in combination.

The materials of the optional layers may be hydrophobic or hydrophilic depending on their functions and placement within or relative to the absorbent structure.

The materials of the optional layers may be formed of constituent fibers or filaments including polymers such as polyethylene, polypropylene, polyester, copolymers thereof, and blends thereof. Filaments may be formed in a spunbond process. Filaments may be formed in a meltblowing process. Fibers or filaments may also be formed of or include cellulose, rayon, cotton, or other natural materials or blends of polymeric and natural materials. The fibers or filaments may also include a superabsorbent material such as polyacrylate or any combination of suitable materials. The fibers or filaments may be monocomponent, bicomponent, and/or biconstituent, non-round (e.g., capillary channel fibers), and may have major cross-sectional dimensions (e.g., diameter for round fibers) ranging from 0.1-500 microns. The constituent fibers or filaments of the nonwoven precursor web may also be a mixture of different types, differing in such features as chemistry (e.g. polyethylene and polypropylene), components (mono- and bi-), denier (micro denier and >20 denier), shape (i.e., capillary and round) and the like. The constituent fibers or filaments may range from about 0.1 denier to about 100 denier.

The optional layers may include thermoplastic particulates, fibers or filaments. The materials, and in particular thermoplastic fibers or filaments, may be made from a variety of thermoplastic polymers including polyolefins such as polyethylene and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers or filaments derived from, for example, polyolefins such as polyethylene or polypropylene, polyacrylics, polyamides, polystyrenes, and the like. The surface of the hydrophobic thermoplastic fiber or filament may be rendered hydrophilic by treatment with a surfactant, such as a nonionic or anionic surfactant, e.g., by spraying the fiber or filament with a surfactant, by dipping the fiber or filament into a surfactant or by including the surfactant as part of the polymer melt in producing the thermoplastic fiber. Upon melting and resolidification, the surfactant will tend to remain at the surfaces of the thermoplastic fiber or filament. Suitable surfactants include nonionic surfactants such as BRIJ 76 manufactured by ICI Americas, Inc. of Wilmington, Del., and various surfactants sold under the PEGOSPERSE by Glyco Chemical, Inc. of Greenwich, Conn. Besides nonionic surfactants, anionic surfactants may also be used. These surfactants may be applied to the thermoplastic fibers at levels of, for example, from about 0.2 to about 1 g/cm$^2$ of thermoplastic fiber or filament.

Suitable thermoplastic filaments may be made from a single polymer (monocomponent filaments), or may be made from more than one polymer (e.g., bicomponent filaments). Suitable bicomponent fibers for use in structures contemplated herein may include fibers with components having a sheath/core configuration, eccentric sheath/core configuration or side-by-side configuration. Side-by-side or eccentric sheath/core configurations may be preferred rather than coaxial sheath/core configurations because of their tendency to impart curl or crimp to the spun filaments resulting from differing contraction rates of the components upon cooling following spinning. This may be preferred in some circumstances because crimped or curled constituent filaments will impart greater loft to the web than uncrimped/uncurled filaments, and impart the web with greater perceivable softness and comfort attributes; such circumstances may include, for example, when the finished nonwoven web product is to be manufactured with a relatively low basis weight that would otherwise result in a relatively thin (low-caliper) product. Polymeric components may include any of the following combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON, CELBOND, or CHISSO bicomponent fibers).

The optional layers may also include synthetic fibers or filaments that typically do not contribute to bonding but alter the mechanical properties of the fibrous webs. Such synthetic fibers or filaments may fibers or filaments formed of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, and mixtures thereof. These might include, for example, polyesters such as polyethylene terephthalate (e.g., DACRON, and KODEL), high melting polyester (e.g., KODEL 431 made by Eastman Chemical Co.) hydrophilic nylon (HYDROFIL), and the like. Suitable fibers or filaments may also hydrophilized hydrophobic, for example, by surfactant- or silica-treating. In the case of nonbonding thermoplastic fibers, their length may vary depending upon the particular properties desired for these fibers. Typically they have a length from about 0.3 to 7.5 cm, such as, for example from about 0.9 to about 1.5 cm. Suitable nonbonding thermoplastic fibers may have a decitex in the range of about 1.5 to about 35 decitex, such as, for example, from about 14 to about 20 decitex.

Adjusting Topsheet Surface Chemistry for Hydrophilicity

Figure 20:
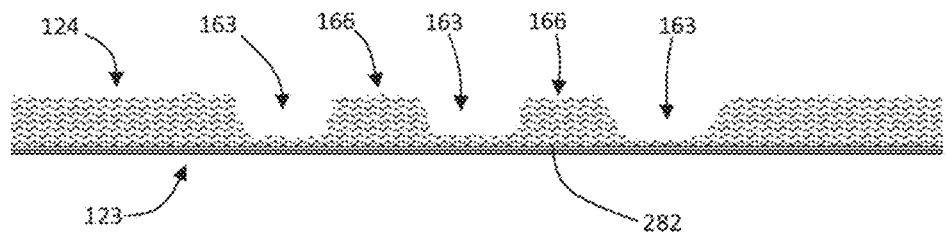
FIGS. 20 and 21 are schematic lateral cross-section views of portions of examples of topsheets formed of nonwoven web material, illustrating presence of materials added to primary filament components.

Referring to FIG. 20, the functions of a topsheet formed as described herein may be enhanced by adding hydrophilic material to the formed nonwoven web material at select locations. In some examples, a surfactant may be selectively applied to the absorbent-facing surface 123 of the topsheet material. In a more particular example, a surfactant, or solution or emulsion containing a surfactant, may be applied to an absorbent-facing side of the topsheet material via, for example, use of a kiss roll coater, spray application, printing technique, or any other suitable liquid deposition technique, to deposit an application of surfactant or solution or emulsion containing a surfactant 282 to the material. Under suitable conditions including suitable disposition of filaments and/or fibers in nonwoven web material, and process techniques/conditions, filaments and/or fibers and/or portions thereof occupying and defining the absorbent-facing surface 123 of the topsheet material and the bottoms of the channel portions 164 will have the surfactant applied to them, while filaments and/or fibers and/or portions thereof occupying and defining the wearer-facing surface 124, and built-up regions 166 thereof will have little or no applied surfactant on their wearer-facing surfaces, such that the surfactant is present in a quantity greater on filaments proximate the absorbent-facing side than on filaments proximate the wearer-facing side. In the resulting topsheet, aqueous fluid (liquid body exudate) may be more likely to flow in and along the channels 164 and/or drain into discrete low bulk portions 165, and through the bottom portions thereof generally along a z-direction, to reach absorbent material disposed below the topsheet in the absorbent article, and the built-up regions 166 adjacent the attenuated regions 163, having a relatively greater number of hydrophobic filaments and/or fibers, may tend to slow or block passage of aqueous fluid along the wearer-facing surface 124, along an x-y plane toward the outer perimeter 128 of the in-use wearer-facing portion 126 of the topsheet. It will be appreciated that, to refine or enhance the desired fluid channeling/barrier and/or draining effect, surfactant application techniques and equipment may be adapted to selectively apply surfactant to limited or defined portions of the section(s) of nonwoven web material forming the topsheet. For example, surfactant may be applied only to portions of the absorbent-facing surface 123 lying to the inside of one or more of the channel portions 164 (with respect to an x-y plane occupied by the material), or to portions of the absorbent-facing surface 123 that does not include wing portions 114, etc. Where the nonwoven is predominately formed of polypropylene, in a non-limiting example, a surfactant suitable for application via KISS roll equipment or alternatively inkjet printing equipment may include STANTEX 56887 surfactant spin finish, a product of Pulcra Chemicals/Fashion Chemicals GmbH & Co., Geretsried, Germany.

Figure 21:
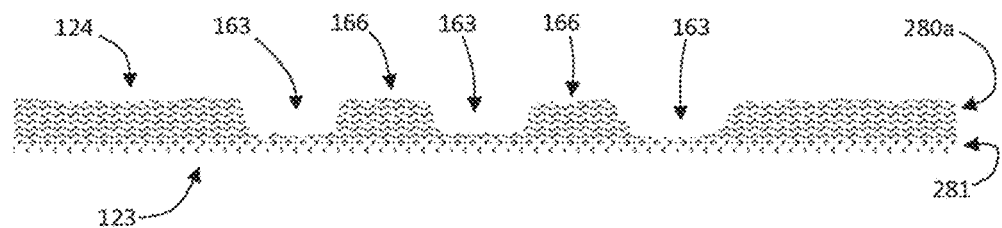

Referring to FIG. 21, in another example, for effects similar to those described immediately above, a nonwoven web material formed as described herein may be coupled via bonding or otherwise with a second layer 281 of filaments and/or fibers formed of hydrophilic material, to form the absorbent-facing surface of the topsheet. In some examples, this second layer 281 may be a second, separately manufactured web material. In other examples, this second layer 281 may be a deposit of filaments and/or fibers deposited over the primary (hydrophobic) filaments and/or fibers forming the built-up regions 166 and channel portions 164 and the wearer-facing surface 124, during the same web manufacturing process.

Coloration

Polymer component resins to be melt spun may include coloring agents such as tinting or pigmenting agents, and/or whitening and/or opacifying agents. In some examples, all of the filaments and/or fibers forming the nonwoven web material may be tinted or pigmented. Alternatively, a second layer 281, of nonwoven material, or of deposited, spun filaments and/or fibers may also include filaments and/or fibers spun from polymer resin blended with a tinting and/or pigmenting agent, to impart a color to the filaments and/or fibers that contrasts with the color of the filaments and/or fibers in first layer 280a. This may be desired for enhancing the visual impact of the ordered arrangement of changes in fiber and/or filament area density and basis weight between the attenuated regions 163 and the built-up regions 166 (see description below) of the web material. In one non-limiting example, filaments and/or fibers of the first layer 280a may include no tinting or pigmenting agents, while filaments and/or fibers of the second layer 281 may include one or more tinting or pigmenting agents. In another non-limiting example, filaments and/or fibers of the first layer 280a may include a whitening and/or opacifying agent (such as, for example, TiO$_2$), and filaments and/or fibers of the second layer may include a coloring agent such as a non-white pigmenting or tinting agent. It will be appreciated that these and other combinations of tinting, whitening, opacifying and/or pigmenting agents may be used to impart visible color contrast between first and second layers forming the web material. In still other examples, underlying materials such as materials forming the absorbent structure and/or the backsheet may include whitening, tinting or pigmenting agents selected to provide visual contrast with the topsheet.

Pigmenting, whitening and/or opacifying agents may be obtained pre-dispersed in carrier resins, in color masterbatch products suitable for blending with filament component resin(s) prior to or during introduction into the extruder(s). The agent(s) selected are preferably solid, powdered compositions that do not dissolve in or react chemically with the polymer resins when blended and dispersed within the filament component resins as they are melted, extruded and spun into filaments under ordinary melt-spinning process conditions. Suitable pigmenting agents may include solid inorganic or organic compositions, and in some examples may be solid organometallic compositions.

Suitable white pigment masterbatch products typically include solid metallic and/or organometallic compositions, for example, Antimony White, Barium Sulfate, Lithopone, Cremnitz White, Titanium White ($TiO_2$), and Zinc White (ZnO).

In some examples, filaments forming the finished, formed nonwoven web material 280, or at least a first layer 280a thereof, may be spun from polymer resin(s) to which a blue pigmenting agent has been added. The inventors believe that an appropriate concentration of blue pigment added to the filament component resin may have a dramatic impact on visibility of the variances in basis weight and caliper in the ordered arrangement, enhancing the appearance of z-direction depth and overall three-dimensional structure. Without intending to be bound by theory, the inventors believe that other single pigments or combinations of pigments, admixed with the filament resin(s) to select weight percent concentrations, may have a similar effect on enhancing the visibility of apparent depth and/or visibility of three-dimensional structural features of the nonwoven web 280.

Suitable blue pigment masterbatch products typically also include solid metallic and/or organometallic compositions, for example, Ultramarine, Persian Blue, Cobalt Blue, Cerulean Blue, Egyptian Blue, Han Blue, Azurite, Prussian Blue, YImMn Blue and Manganese Blue. In a particular example, a blue color masterbatch product may be admixed to a concentration of approximately 0.25% of total weight polypropylene filament spinning resin, where the masterbatch product comprises approximately 36% by weight blue pigment composition. It is believed that an effective weight percent concentration of blue pigment material within the total spinning resin blend, for purposes of enhancing visibility of apparent depth and/or visibility of three-dimensional structural features of the nonwoven web 280 as described above, may be from approximately 0.03 percent to approximately 0.15 percent, more preferably from approximately 0.06 percent to 0.12 percent.

In yet another approach, an ink of a non-white color or color that contrasts with the spun filament color, may be applied via any suitable technique to the surface of the nonwoven web material that will become the absorbent-facing surface of a topsheet, to enhance visual impact as described above.

Process for Manufacturing Topsheet Material

Formed nonwoven web material from which topsheets as described above may be formed using equipment, processes and materials described in, for example, any of US application pub. nos. US 2017/0191198; US 2017/0029994; US 2017/0029993 and US 2017/0027774, and U.S. application Ser. Nos. 15/840,455; 15/879,474; 15/879,477; 15/881,910; 62/527,216; 62/527,224, 62/819,729; and 62/819,744, the disclosures of which are incorporated by reference herein.

Formed nonwoven web materials may be manufactured from spun filaments in a spunbond process, utilizing a specially adapted forming belt. The topsheet may be formed predominately of spunbond filaments or substantially entirely of spunbond filaments. Additional web loft and manufacturing efficiency may be achieved when the topsheet is formed of spunbond, bicomponent filaments. Bicomponent filaments may spun so as to have a side-by-side bicomponent configuration, such that suitable selection of differing resin components will impart crimp or curl to the filaments as they cool; crimp or curl of the filaments can help contribute to loft of the resulting web.

Topsheet Formation Process Components

Figure 11:
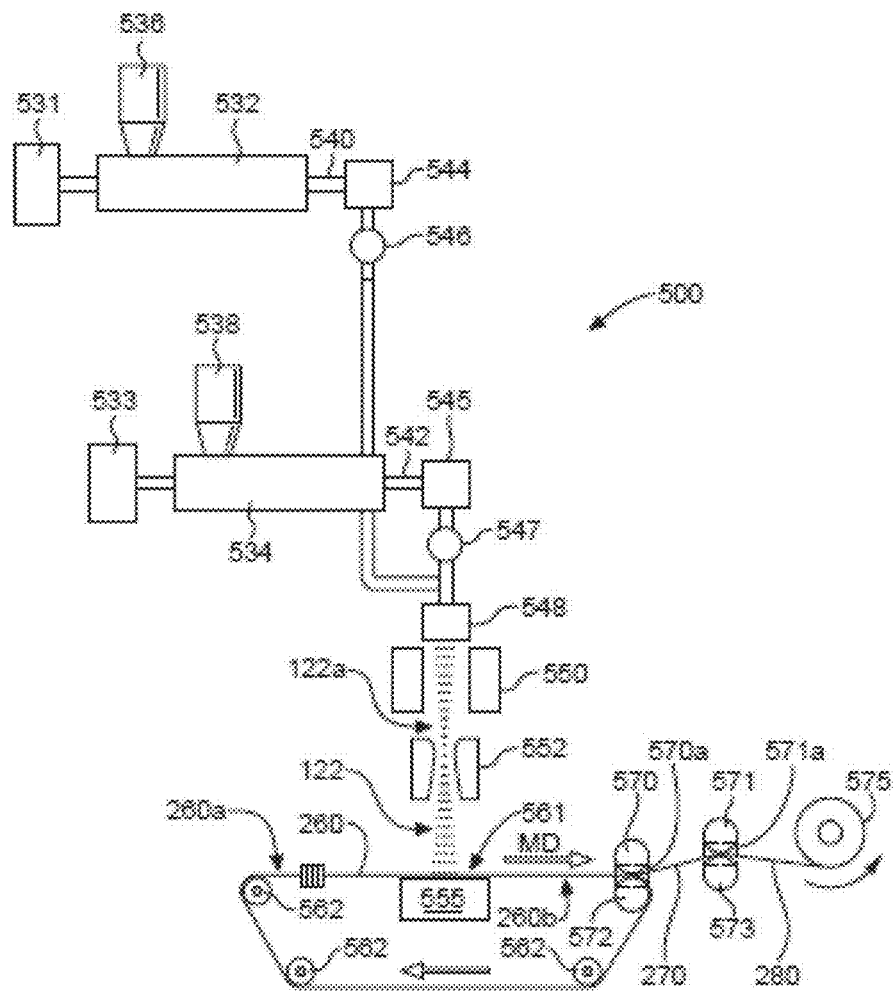
FIG. 11 is a schematic side-view illustration of an example of configuration of equipment for manufacturing a nonwoven web material.

For example, referring to FIG. 11, a process line 500 for manufacturing a formed nonwoven web material of bicomponent filaments may include a pair of melt extruders 532 and 534, driven by extruder drives 531 and 533, respectively, for separately melting and extruding a first polymer component resin and a second polymer component resin. The first polymer component resin may be fed into the respective extruder 532 from a first hopper 536 and the second polymer component resin may be fed into the respective extruder 534 from a second hopper 538. The first and second polymer component resins may melted and driven by the extruders 532 and 534 through respective polymer conduits 540 and 542 then through filters 544 and 545, to melt pumps 546 and 547, which help pump the polymer into and through a spin pack 548. Spin packs with spinnerets used in spinning bicomponent filaments are known in the art and therefore are not described here in great detail.

Generally described, a spin pack 548 may include a housing which includes a plurality of plates stacked one on top of the other with a pattern of openings arranged to create flow paths for directing the melted first and second polymer component resins separately through spinneret openings. The spin pack 548 may have spinneret openings arranged in one or more rows. As the melted polymer resins are forced through them, the spinneret openings emit a downward curtain of individual melted polymer streams 122a. For the purposes of the present disclosure, spinnerets may be arranged to form streams for sheath/core or side-by-side bicomponent filaments. Bicomponent filaments may be preferred in some circumstances for their particular characteristics. Side-by-side or eccentric or asymmetric core/sheath bicomponent filaments may be preferred where it is desired that the spun filaments have a spiral or curl imparted by differing cooling contraction rates of differing components, wherein spiral or curl in the spun filaments may contribute to enhanced loft and bulk of the nonwoven web material. Core/sheath bicomponent filaments may be preferred where it is desired that the respective components have differing attributes or properties that might be advantageously balanced. Such attributes or properties might include raw material (resin) cost, or spun tensile strength, or surface feel or surface friction. In one example, a core/sheath filament in which the core component is predominately polypropylene and the sheath component is predominately polyethylene may be preferred, wherein polypropylene is selected for the core component for its relatively lower cost and contribution to filament tensile strength, and polyethylene is selected for the sheath component for a relatively lower melting point (for purposes of thermal bonding between filaments) and a relatively lower-friction, silkier feel it imparts to the filament surfaces.

Although the above description contemplates spinning bicomponent filaments, it will be appreciated that the equipment and materials supplied may be adapted, selected and configured to spin monocomponent filaments, or multicomponent filaments having more than two components.

Spinnerets may be configured and adapted to form streams with generally circular cross-sections (to form filaments with generally round/circular cross sections), or streams with generally non-round cross sections such as asymmetric, multi-lobal, e.g., trilobal cross sections (to form asymmetric, lobed, e.g., trilobal filaments). Lobed filaments may be desired in some circumstances for their effects on fluid flow along their surfaces, for their effects on filament and nonwoven opacity, for their effects on fiber and nonwoven feel, or a combination of these effects. Generally, a nonwoven web material formed of lobed filaments such as trilobal filaments has greater opacity than an otherwise comparable nonwoven web material formed of round filaments, as a result of greater light refraction and/or diffusion through trilobal filaments. Fluid flow along filament surfaces may be enhanced or inhibited to a greater extent by lobed cross sections, depending upon whether the surfaces of the filaments are hydrophilic or hydrophobic, respectively.

The process line 530 also may include a quench blower 550 positioned beneath/adjacent the location the polymer streams 122a exit the spinnerets. Temperature, velocity and direction of air from the quench air blower 550 may be suitably controlled to quench the polymer streams, causing them to partially solidify. Quench air may be provided and directed at one (upstream or downstream) side of the curtain or both sides of the curtain.

An attenuator 552 may be positioned below the spinneret to receive the quenched polymer streams 122a. Filament draw units or aspirators for use as attenuators in melt spinning polymers are known in the art. Suitable filament draw units for use in the process of the present disclosure may include a linear filament attenuator of the type shown in U.S. Pat. No. 3,802,817, or eductive guns of the type shown in U.S. Pat. Nos. 3,692,618 and 3,423,266, the disclosures of which are incorporated herein by reference.

Generally, the attenuator 552 may include and define an elongate vertical passage through which the polymer streams 122a may be entrained in a downward air stream, drawn downward, elongated and reduced in cross section to form filaments 122. A shaped, at least partially foraminous forming belt 260 is positioned below the attenuator 552 and receives the downward-moving continuous filaments from the outlet opening of the attenuator 552. The forming belt 260 is a continuous belt, having an outer receiving side 260a and an inner side 260b, and cycles about guide rollers 562, one or more of which may be driven at a controlled speed to cause the belt to translate along an x-y plane and along a machine direction MD through a working location 561 beneath the attenuator. A forming vacuum system 555 may be positioned below the working location 561 of the belt 260 where the filaments are deposited, to draw the air of the air stream through the belt, and thereby draw the entrained filaments toward and against the belt surface. Although the forming belt 260 is shown and described as a belt herein, it will be understood that a forming device with a suitable forming surface may also have other forms, such as a rotatable drum with a suitable cylindrical forming surface. Features of examples of shaped forming belts are described below.

In operation of the process line 500, the hoppers 536 and 538 may be supplied with the respective desired first and second polymer component resin(s). First and second polymer component resin(s) may be melted by the respective extruders 532 and 534, and forced in their melted state through polymer conduits 540 and 542 to spin pack 548. The line may include filters 544, 545 to filter out solid impurities from the melted resins, and the line may also include supplemental melt pumps 546, 547 to increase pressure in the conduits and thereby assist in driving the polymer components to and through the spin pack 548. Although the temperatures of the melted polymer resins can be controlled and varied for the polymers used and desired process conditions, when one or both of polyethylene and polypropylene are predominately the component resins, the temperatures of the melted polymer resins may be controlled to be within a range from about 190 deg. C. to about 240 deg. C.

Topsheet Filament Spinning Resin Formulation

Non-limiting examples of particularly suitable polymeric resins for spinning bicomponent filaments contemplated herein include PH835 polypropylene obtained from LyondellBasell (Rotterdam, Netherlands) and Aspun-6850-A polyethylene obtained from Dow Chemical Company (Midland, Mich., USA). Although polypropylene and polyethylene are contemplated as predominant polymer resin constituents for spinning filaments, for their thermodynamic and mechanical attributes combined with their costs at the present time, a wide variety of polymers may be suitable for use within the scope of the present disclosure. Other suitable examples include PP3155 and ACHIEVE 3854 products available from ExxonMobil, Irving, Tex.

Non-limiting examples of potentially suitable synthetic polymers include thermoplastic polymers, such as polyesters, nylons, polyamides, polyurethanes, polyolefins (such as polypropylene, polyethylene and polybutylene), polyvinyl alcohol and polyvinyl alcohol derivatives, sodium polyacrylate (absorbent gel material), and copolymers of polyolefins such as polyethylene-octene or polymers comprising monomeric blends of propylene and ethylene, and biodegradable or compostable thermoplastic polymers such as polylactic acid, polyvinyl alcohol, and polycaprolactone. Potentially suitable natural polymers include starch, starch derivatives, cellulose and cellulose derivatives, hemicellulose, hemicelluloses derivatives, chitin, chitosan, polyisoprene (cis and trans), peptides and polyhydroxyalkanoates. In one example, a predominate polymer component for spinning filaments may be a thermoplastic polymer selected from the group consisting of: polypropylene, polyethylene, polyester, polylactic acid, polyhydroxyalkanoate, polyvinyl alcohol, polycaprolactone, styrene-butadiene-styrene block copolymer, styrene-isoprene-styrene block copolymer, polyurethane, and mixtures thereof. In another example, the thermoplastic polymer may be selected from the group consisting of: polypropylene, polyethylene, polyester, polylactic acid, polyhydroxyalkanoate, polyvinyl alcohol, polycaprolactone, and mixtures thereof. Alternatively, the polymer may comprise one derived from monomers which are partially produced by biological processes, such as bio-polyethylene or bio-polypropylene.

In some circumstances it may be desired to manipulate and/or the enhance features of the spun filaments such as color, opacity, pliability, hydrophilicity/hydrophobicity and/or surface feel (e.g., surface coefficient of friction) of fibers spun from the component resin(s). In such circumstances one or more melt additives may be included with the resin(s) fed to the extruder(s).

Inorganic fillers such as the oxides of magnesium, aluminum, silicon, and titanium may be added to the polymer resins as whiteners, opacifiers, fillers or processing aides. Other inorganic materials include hydrous magnesium silicate, titanium dioxide, calcium carbonate, clay, chalk, boron nitride, limestone, diatomaceous earth, mica glass quartz, and ceramics.

Topsheet Filament Surface Property Manipulation

Slip agent melt additives may be included in an amount sufficient to affect and/or enhance desired haptic properties (e.g., impart a soft/silky/slick feel) to the filaments. Some slip agents when melt-blended with the resin gradually migrate to the filament surfaces during cooling or after fabrication, hence forming a thin coating with lubricating effects, in the filament surfaces. It may be desired that the slip agent be a fast-bloom slip agent, and can be a hydrocarbon having one or more functional groups selected from hydroxide, aryls and substituted aryls, halogens, alkoxys, carboxylates, esters, carbon unsaturation, acrylates, oxygen, nitrogen, carboxyl, sulfate and phosphate. In one particular form, the slip agent is a salt derivative of an aromatic or aliphatic hydrocarbon oil, notably metal salts of fatty acids, including metal salts of carboxylic, sulfuric, and phosphoric aliphatic saturated or unsaturated acid having a chain length of 7 to 26 carbon atoms, preferably 10 to 22 carbon atoms. Examples of suitable fatty acids include the monocarboxylic acids lauric acid, stearic acid, succinic acid, stearyl lactic acid, lactic acid, phthalic acid, benzoic acid, hydroxystearic acid, ricinoleic acid, naphthenic acid, oleic acid, palmitic acid, erucic acid, and the like, and the corresponding sulfuric and phosphoric acids. Suitable metals include Li, Na, Mg, Ca, Sr, Ba, Zn, Cd, Al, Sn, Pb and so forth. Representative salts include, for example, magnesium stearate, calcium stearate, sodium stearate, zinc stearate, calcium oleate, zinc oleate, magnesium oleate and so on, and the corresponding metal higher alkyl sulfates and metal esters of higher alkyl phosphoric acids.

In other examples, the slip agent may be a non-ionic functionalized compound. Suitable functionalized compounds include: (a) esters, amides, alcohols and acids of oils including aromatic or aliphatic hydrocarbon oils, for example, mineral oils, naphthenic oils, paraffinic oils; natural oils such as castor, corn, cottonseed, olive, rapeseed, soybean, sunflower, other vegetable and animal oils, and so on. Representative functionalized derivatives of these oils include, for example, polyol esters of monocarboxylic acids such as glycerol monostearate, pentaerythritol monooleate, and the like, saturated and unsaturated fatty acid amides or ethylenebis(amides), such as oleamide, erucamide, linoleamide, and mixtures thereof, glycols, polyether polyols like Carbowax, and adipic acid, sebacic acid, and the like; (b) waxes, such as carnauba wax, microcrystalline wax, polyolefin waxes, for example polyethylene waxes; (c) fluoro-containing polymers such as polytetrafluoroethylene, fluorine oils, fluorine waxes and so forth; and (d) silicon compounds such as silanes and silicone polymers, including silicone oils, polydimethylsiloxane, amino-modified polydimethylsiloxane, and so on.

Fatty amides that may be useful for purposes of the present disclosure are represented by the formula: RC(O)NHR¹, where R is a saturated or unsaturated alkyl group having 7 to 26 carbon atoms, preferably 10 to 22 carbon atoms, and R1 is independently hydrogen or a saturated or unsaturated alkyl group having from 7 to 26 carbon atoms, preferably 10 to 22 carbon atoms. Compounds according to this structure include for example, palmitamide, stearamide, arachidamide, behenamide, oleamide, erucamide, linoleamide, stearyl stearamide, palmityl palmitamide, stearyl arachidamide and mixtures thereof.

Ethylenebis(amides) that may be useful for purposes of the present disclosure are represented by the formula:

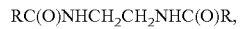

RC(O)NHCH$_2$CH$_2$NHC(O)R, where each R is independently is a saturated or unsaturated alkyl group having 7 to 26 carbon atoms, preferably 10 to 22 carbon atoms. Compounds according to this structure include for example, stearamidoethylstearamide, stearamidoethylpalmitamide, palmitamidoethylstearamide, ethylenebisstearamide, ethylenebisoleamide, stearylerucamide, erucamidoethylerucamide, oleamidoethyloleamide, erucamidoethyloleamide, oleamidoethylerucamide, stearamidoethylerucamide, erucamidoethylpalmitamide, palmitamidoethyloleamide and mixtures thereof.

Commercially available examples of fatty amides include Ampacet 10061 (Ampacet Corporation, White Plains, New York, USA) which comprises 5 percent of a 50:50 mixture of the primary amides of erucic and stearic acids in polyethylene; Elvax 3170 (E.I. du Pont de Nemours and Company/DuPont USA, Wilmington, Delaware, USA) which comprises a similar blend of the amides of erucic and stearic acids in a blend of 18 percent vinyl acetate resin and 82 percent polyethylene. Slip agents also are available from Croda International Plc (Yorkshire, United Kingdom), including Crodamide OR (an oleamide), Crodamide SR (a stearamide), Crodamide ER (an erucamide), and Crodamide BR (a behenamide); and from Crompton, including Kemamide S (a stearamide), Kemamide B (a behenamide), Kemamide O (an oleamide), Kemamide E (an erucamide), and Kemamide (an N,N'-ethylenebisstearamide). Other commercially available slip agents include Erucamid ER erucamide.

Other suitable melt additives for softness/reduction of the coefficient of friction include erucamide, stearamide, oleamide, and silicones e.g. polydimethylsiloxane. Some specific examples include CRODAMIDE slip & anti-block agents from Croda International Plc (Yorkshire, United Kingdom), and slip BOPP agents from Ampacet Corporation (White Plains, New York, USA). Some additional specific examples of softness/reduction of the coefficient of friction melt additives specifically tailored for polypropylene are available from Techmer PM Company (Clinton, Tennessee, USA).

Nonwoven web materials within contemplation of the present disclosure may include slip agents/softness melt additives independently, or in conjunction with other additives that affect the surface energy (hydrophilicity/hydrophobicity), or in conjunction with other filament feature variations including but not limited to filament size, filament cross-sectional shape, filament cross-sectional configuration, and/or curled filament variations. For examples of nonwoven web materials including two or more web layers, or two or more deposited layers of differing filaments, additives may be included in filaments of one layer but not the other, or differing additives may be included in filaments of differing layers.

As noted herein, in some examples it may be desired that filaments present at and proximate to the absorbent-facing surface 123 of the topsheet have hydrophilic surface energy properties. To impart the filaments with such properties, they may be spun from one or more resin(s) inherently having such properties, or alternatively, they may be spun from resin(s) blended with a melt additive that renders the resulting spun filaments hydrophilic. Alternatively, after spinning, the filaments, the batt or the finished web may be treated with a material such as a surfactant renders them hydrophilic. This may be desired for purposes of selectively imparting portions of the topsheet (such as the absorbent-facing surface 123) with hydrophilicity, to affect its fluid handling characteristics.

In conjunction therewith, it may be desired that filaments present within the topsheet at locations more removed from the absorbent-facing surface 123, including filaments present at and proximate to the wearer-facing surface 124, be spun from inherently hydrophobic resin, or additionally or alternatively, be spun from resin blended with a melt additive that renders the resulting spun filaments hydrophobic, or enhances hydrophobicity. Inherent and/or enhanced hydrophobicity of filaments as spun may help prevent unwanted migration of an applied solution, emulsion or concentrate of surfactant in a z-direction from the absorbent-facing surface toward the wearer-facing surface, and may also enhance the capability of the filaments in built-up regions 166 of the topsheet to serve as barriers to migration of aqueous body exudate across the topsheet along a direction in the x-y plane, toward the outer edges of the pad. Hydrophobicity of filaments may be enhanced via addition of hydrophobizing melt additives to the resin(s) from which the filaments are to be spun.

In some examples, a hydrophobizing melt additive may be added directly or as master batch to the polymer melt during the spinning process. Suitable melt additives may include, for example, lipid esters or polysiloxanes. When a hydrophobizing melt additive is blended into resin(s), the additive in the resulting spun filament can bloom to its external surface and create a film covering portions of the surface, form fibrils, flakes, particles, or other surface features that have low surface energy.

Any suitable hydrophobizing melt additive may be utilized. Examples of hydrophobizing melt additives include fatty acids and fatty acid derivatives. The fatty acids may originate from vegetable, animal, and/or synthetic sources. Some fatty acids may range from a C8 fatty acid to a C30 fatty acid, or from a C12 fatty acid to a C22 fatty acid. In other forms, a substantially saturated fatty acid may be used, particularly when saturation arises as a result of hydrogenation of fatty acid precursor. Examples of fatty acid derivatives include fatty alcohols, fatty acid esters, and fatty acid amides. Suitable fatty alcohols (R—OH) include those derived from C12-C28 fatty acids.

Suitable fatty acid esters include those fatty acid esters derived from a mixture of C12-C28 fatty acids and short chain (C1-C8, preferably C1-C3) monohydric alcohols preferably from a mixture of C12-C22 saturated fatty acids and short chain (C1-C8, preferably C1-C3) monohydric alcohols. The hydrophobizing melt additive may comprise a mixture of mono, di, and/or tri-fatty acid esters. An example includes fatty acid ester with glycerol as the backbone as illustrated in illustration [1], below:

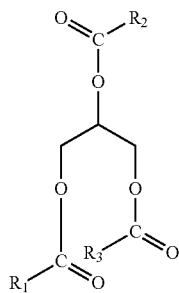

[1]

where R1, R2, and R3 each is an alkyl ester having carbon atoms ranging from 11 to 29. In some forms, the glycerol derived fatty acid ester has at least one alkyl chain, at least two, or three chains to a glycerol, to form a mono, di, or triglyceride. Suitable examples of triglycerides include glycerol thibehenate, glycerol tristearate, glycerol tripalmitate, and glycerol trimyristate, and mixtures thereof. In the case of triglycerides and diglycerides, the alkyl chains could be the same length, or different length. Example includes a triglyceride with one alkyl C18 chain and two C16 alkyl chain, or two C18 alkyl chains and one C16 chain. Preferred triglycerides include alkyl chains derived from C14-C22 fatty acids.

Suitable fatty acid amides include those derived from a mixture of C12-C28 fatty acids (saturated or unsaturated) and primary or secondary amines. A suitable example of a primary fatty acid amide includes those derived from a fatty acid and ammonia as illustrated in illustration [2], below:

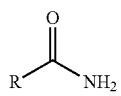

[2]

where R has a number of carbon atoms ranging from 11 to 27. In at least one other form, the fatty acids may range from a C16 fatty acid to a C22 fatty acid. Some suitable examples include erucamide, oleamide and behanamide. Other suitable hydrophobizing melt additives include hydrophobic silicones. Additional suitable hydrophobizing melt additives are disclosed in U.S. patent application Ser. No. 14/849,630 and U.S. patent application Ser. No. 14/933,028. Another suitable hydrophobizing melt additive is available from Techmer PM in Clinton, Tenn. under the trade name PPM17000 High Load Hydrophobic. One specific example of a hydrophobizing melt additive is glycerol tristearate. As used herein, glycerol tristearate is defined as a mixture of long-chained triglycerides containing predominately C18 and C16 saturated alkyl chain lengths. Additionally, there could be varying degrees of unsaturation and cis to trans unsaturated bond configurations. The alkyl chain lengths could range from about C10 to about C22. The degrees of unsaturation typically will range from 0 to about 3 double bonds per alkyl chain. The ratio of cis to trans unsaturated bond configurations can range from about 1:100 to about 100:1. Other suitable examples for use with polypropylene and/or polyethylene, a triglyceride which contains either stearic acid or palmic acid or both as the fatty acid components, or a mixture of such triglycerides. Other suitable hydrophobizing melt additives may comprise erucamide or polysiloxanes.

As noted herein, in some examples, it may be desired that constituents of the web material include filaments having surface energy properties that make them hydrophilic. As noted, it may be desired in some circumstances that filaments forming and proximate to the absorbent-facing surface of the topsheet have hydrophilic surfaces. In some examples this may be accomplished via use of hydrophilizing melt additives to the resin(s) from which filaments are spun.

Any suitable hydrophilizing additive can be used. Some suitable examples include those available from Techmer PM, Clinton, Tennessee sold under the trade name of TECHMER PPM15560; TPM12713, PPM19913, PPM 19441, PPM19914, PPM112221 (for polypropylene), PM19668, PM112222 (for polyethylene). Additional examples are available from Polyvel Inc. located in Hammonton, N.J., sold under the trade name of POLYVEL VW351 PP Wetting Agent (for polypropylene); from Goulston Technologies Inc. located in Monroe, N.C. sold under the trade name HYDROSORB 1001; as well as those hydrophilizing additives disclosed in U.S. Patent Application Publication No. 2012/0077886 and U.S. Pat. Nos. 5,969,026 and 4,578,414.

Nucleating agents may be included along with melt additives. Nucleating agents can help to drive more or faster blooming of either a hydrophilizing or hydrophobizing melt additive. A nucleating agent when melt-blended with constituent resin(s) and a hydrophilizing or hydrophobizing melt additive will enhance the hydrophilizing or hydrophobizing effect or wetting contact angle effect in the filaments (depending on the type of additive), as compared with the same hydrophilizing or hydrophobizing melt-additive used without a nucleating agent. Suitable nucleating agents may include a nonitol, a trisamide and/or a sorbitol-based nucleating agent. Specific but non-limiting examples include: organic nucleation agents such as MILLAD NX 8000 or (in its new trade name) NX ULTRACLEAR GP110B from Milliken & Company, Spartanburg, South Carolina. An example of an effective inorganic nucleating agent is $CaCO_3$, or other and especially nano-clay or nano-scale mineral molecules.

Some melt additives may serve to enhance tactile softness and/or reduce surface coefficient of friction, as well as modify surface energy, and thereby serve dual purposes. For example, fatty amides when used as melt additives may serve to both reduce surface friction, and enhance hydrophobicity of the filaments. These melt additives are listed herein under hydrophobic melt additives. Other non-limiting examples of potentially suitable softness-enhancing and hydrophobizing melt additives are identified in US 2017/0258651.

During manufacture or in a post-treatment or even in both, the formed nonwoven web materials contemplated herein may be treated with surfactants or other agents to either hydrophilize the material or make it hydrophobic. This is known in the fields of manufacturing and converting nonwoven web materials used to make components of absorbent articles. For example, a formed nonwoven web material used for a topsheet may be treated with a surfactant or other hydrophilizing agent so as to make it more receptive and/or permeable by aqueous body exudates such as urine. For other absorbent articles, the topsheet may allowed to remain at its naturally hydrophobic state or be made even more hydrophobic, through the addition of a hydrophobizing material or surfactant.

Spinning

As the polymer streams 122a exit the spinnerets, a stream of quenching air from the quench blower 550 at least partially quenches the polymers forming the streams, and, for certain polymers, induces crystallization in the polymers. To increase the rate of crystallization/solidification if desired, the quench blower(s) may be configured to direct quench air in a direction approximately perpendicular to the length of the streams. The quenching air may be cooled or heated as deemed suitable to be at a temperature of about 0 deg. C. to about 35 deg. C. and a velocity from about 100 to about 400 feet per minute when it contacts the polymer streams. The streams may be quenched sufficiently to reduce their surface tackiness so as to prevent them from bonding or fusing together to any undesirable extent, upon contact therebetween, as they travel to and are deposited and accumulate on the forming belt 260.

After quenching, the polymer streams 122a may be drawn into the vertical passage of an attenuator 552 and entrained by downward air flow generated by the attenuator 552. The attenuator may in some examples be positioned 30 to 60 inches below the bottom of the spinnerets. The air flow generated by the attenuator moves at a higher downward velocity than that of the entering quenched polymer streams. The attenuating air flow entrains the polymer streams and draws them downwardly, and thereby elongates and reduces their cross sections, thereby forming filaments 122.

The filaments 122 exit the attenuator 552 and travel downwardly substantially in a z-direction with respect to the cycling forming belt 260 having an upward-facing portion moving along the machine direction MD through the working location 561, beneath the attenuator 552. The entraining air exiting the attenuator may be drawn through the air-permeable portions of the forming belt 260 by the forming vacuum system 555, and the filaments 122 are stopped in their z-direction travel by the outer receiving side 260a of the forming belt 260, are deposited and accumulated thereon, and then travel with the forming belt 260 in the machine direction along therewith. It will be appreciated that the rate of deposit and accumulation of the filaments on the forming belt 260 may be controlled by controlling the speed at which the forming belt is cycled, the rate at which the filaments are spun, or a combination of these. As will be further explained below, the forming belt 260 may be configured with features that affect localized rates and depths of accumulation of filaments across its overall surface area in the x-y plane, to result in formation of a batt of filaments 270 and subsequent finished nonwoven web material 280 with a desired ordered arrangement of regions of varying basis weight and/or filament area density and/or thickness or caliper.

In some circumstances it may be desired to include discrete filaments of differing compositions in the nonwoven web material. It will be appreciated that this may be accomplished by configuring equipment carrying differing polymer resins arranged in parallel or in series/sequentially to one or more combinations of spin pack(s), quenching equipment and attenuating equipment configured to spin filaments and direct them at the forming belt. In one non-limiting example, it may be desired that the nonwoven web material have layered deposits of filaments of differing compositions with differing levels of hydrophilicity/hydrophobicity. Referring to FIG. 21, in a particular example, it may be desired that hydrophobic filaments are predominately present proximate the wearer-facing surface 124 of a topsheet material, while hydrophilic filaments are predominately present proximate the absorbent-facing surface 123. It will be appreciated that, to produce such a configuration, the filament spinning equipment may be configured to spin and deposit a first layer 280a of hydrophobic filaments onto the forming belt, and sequentially downstream in the process, to spin and deposit a second layer 281 of differing, hydrophilic filaments over the hydrophobic filaments, as the batt moves along a machine direction on the moving forming belt.

Compaction and Bonding

The process line 500 may further include one or more consolidating devices such as compaction rolls 570 and 572, which form a nip 570a through which the batt 270 may be compacted. Optionally, one or both compaction rolls 570, 572 may be heated to promote partial softening and plastic deformation of the filaments. It may be desired, further, to apply a combination of heat and pressure to the filaments in the nip 570a sufficient to induce some bonding between intermeshing/crossing filaments traveling through nip 570a.

Compaction facilitates neat removal of the batt 270 from the forming belt, and some bonding may enhance this effect as well as impart added machine- and/or cross-direction tensile strength to the finished material. The compaction rolls 570, 572 may be a pair of smooth surface stainless steel rolls with independent heating controllers. One or both compaction rolls may be heated by electric elements or hot oil circulation. The gap between the compaction rolls may be controlled, e.g., hydraulically, to impose desired pressure on the batt as it passes through the nip 570a. In one example, with a forming belt caliper of 1.4 mm, and a spunbond nonwoven having a basis weight of 30 gsm, the nip gap between the compaction rolls 570, 572 may be about 1.35 to 1.50 mm.

In one example, upper compaction roll 570 may be heated to a temperature sufficient to induce melting of bond filaments on the upper surface of the batt 270, to impart cohesion and strength to the batt that may facilitate its removal from forming belt 260 without losing integrity. As shown in FIG. 11, for example, as rolls 570 and 572 rotate, forming belt 260 with the batt laid down on it enter the nip 570a between rolls 570 and 572. Heated roll 570 can heat the portions of nonwoven fabric 10 that are pressed against it most closely, by land surfaces 262a of airflow blocking structures 262 on forming belt 260 (described below), to deform and/or flatten and/or bond filaments proximate the upper surface (i.e., attenuator-side) surface of batt 270, to an extent desired. As can be understood by the description herein, the attenuated regions in which filaments are so deformed will reflect the pattern of the airflow blocking structures 262 on forming belt 260.

After compaction, the compacted batt may be lifted away or separated from the forming belt 260 and be directed through a second nip 571a formed by calender rolls 571, 573. The calender rolls 571, 573 may be stainless steel rolls, one having an engraved or otherwise formed pattern of raised bonding protrusions about its cylindrical surface (bonding roller), and the other being a smooth roll (anvil roller). The bonding roller, or both bonding and anvil rollers, may be heated such that they heat and partially melt the filaments so as to cause them to fuse together in the nip, between the radially outermost surfaces of the bonding protrusions and the anvil roller. The bonding protrusions on the bonding roller may be configured in any suitable regular pattern of relatively closely-spaced bonding "pins" that will effect a like pattern of point bonds in the finished web material 280. The radially outermost surfaces of the bonding protrusions effect localized elevated compression of the batt in the nip 571a, between the bonding protrusions and the anvil roller. These surfaces may have a cumulative surface area about the bonding roller that amounts to a percent fraction of the total cylindrical surface area of the working portion of the bonding roller (bonding area percentage), which will be approximately reflected in the percent fraction of the surface area, in the x-y plane, of the web material that is bonded (bonded area percentage). The bonding area percentage of the bonding roller, and the resulting bonded area percentage of the web material, may be approximately from 3% to 30%, from 6% to 20%, or from 7% to 15%. A pattern of thermal calender point-bonds may serve to improve cohesiveness of the web, and enhance machine direction and cross-direction tensile strength and dimensional stability, useful in downstream processing and incorporation of the formed nonwoven web material into finished products.

Additionally or alternatively, in some examples the batt may be bonded via a hot air bonding process. Through-air thermal bonding may be another approach to create higher loft nonwoven structures which may be desired in some circumstances. Through-air thermal bonding involves the application of hot air to the surface of the filament batt. The hot air flows through holes in a plenum positioned just above the nonwoven. However, the air is not pushed through the nonwoven, as in common hot air ovens. Negative pressure or suction pulls the air through the open conveyor apron that supports the nonwoven as it passes thorough the oven. Pulling the air through the nonwoven fabric allows much more rapid and even transmission of heat and minimizes fabric distortion. As an alternative to use of a conventional through-air bonding unit, it is contemplated placing the bonding unit over the forming belt 260 while a vacuum is operated beneath the belt to draw hot air through the batt, effecting a process similar to that effected by a conventional through-air bonding unit.

Forming Belt Manufacture

A forming belt 260 may be made according to the methods and processes described in U.S. Pat. Nos. 6,610,173; 5,514,523; 6,398,910; or US 2013/0199741, each with the improved features and patterns disclosed herein for making spunbond nonwoven webs. The '173, '523, '910 and '741 disclosures describe belts that are representative of papermaking belts made with cured resin on a belt substrate member, which belts, with improvements and suitable configurations, may be utilized as described herein.

A forming belt 260 having three-dimensional features and patterns for making spunbond nonwoven webs may also be made by the following methods and processes and/or on the following apparatuses, including with modifications as desired for structures taught herein: rotary screen processes as taught in U.S. Pat. No. 7,799,382; polymer extrusion as taught in US 2007/0170610; resin system grafting as taught in U.S. Pat. No. 7,105,465; perforated film as taught in U.S. Pat. No. 8,815,057; successive layer treatment as taught in US 2006/0019567; polymeric droplet deposition as taught in U.S. Pat. No. 7,005,044; polymeric droplet deposition with a sacrificial material as taught in U.S. Pat. No. 7,014,735; air permeable film technology as taught by U.S. Pat. Nos. 8,454,800 or 8,822,009; multilayer belt structures as taught in US 2016/0090692; laser etching as taught by U.S. Pat. Nos. 8,758,569 or 8,366,878; extruded mesh technology as taught in US 2014/0272269; nonwoven belts as described in US 2008/0199655; and additive manufacturing methods and processes as taught in US 2015/0102526A1, or US 2016/0159007, or WO 2016/085704, or US 2016/0185041.

Figure 12:
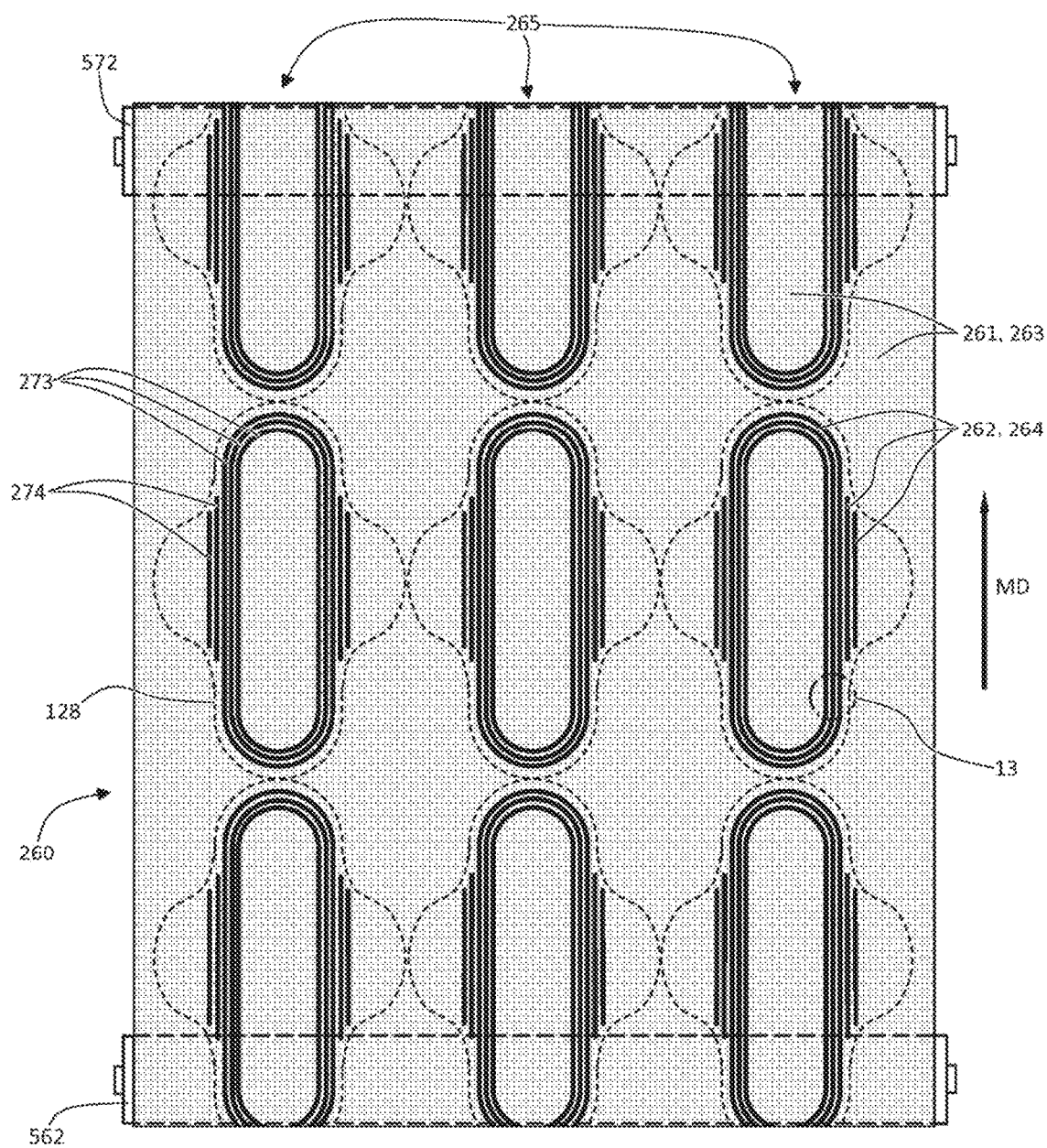
FIG. 12 is a schematic plan view of an example of a portion of a forming belt receiving side as it might appear with the belt disposed about guide/drive rollers.
Figure 13:
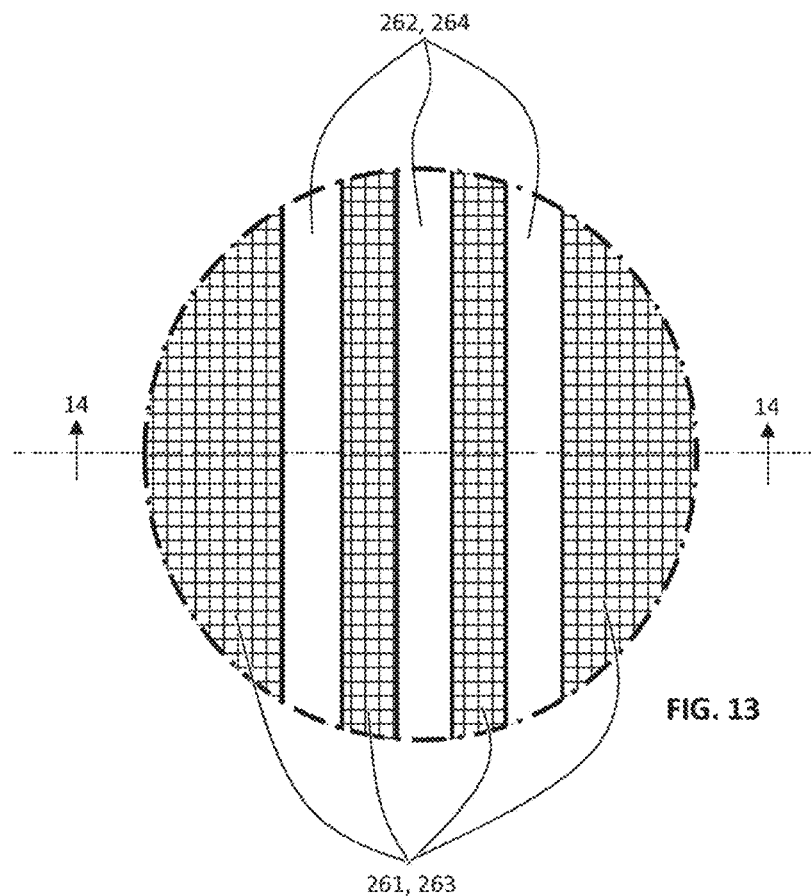
FIG. 13 is an expanded schematic view of the portion of the forming belt receiving side identified as "13" in FIG. 12.
Figure 14:
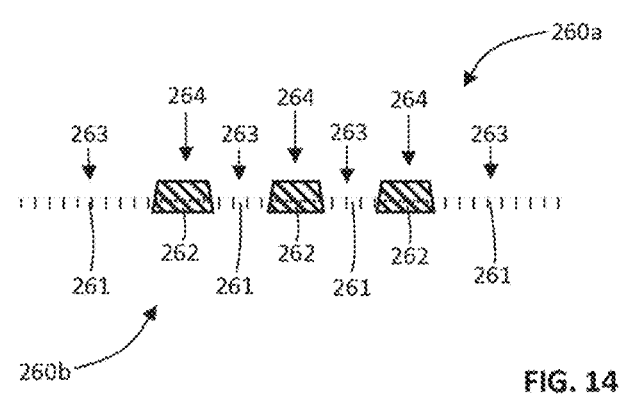
FIG. 14 is a schematic lateral cross section of the portion of the forming belt shown in FIG. 13.

An example of a forming belt 260 of the type useful for purposes of the present disclosure and which may be made according to the disclosure of U.S. Pat. No. 5,514,523, is schematically depicted in FIGS. 12-14. As taught in the '523 patent, a flat sheet of substrate belt material 261 is thoroughly coated with a liquid photosensitive polymeric resin to a preselected thickness. The substrate belt material 261 (called a "reinforcing structure" in the '523 patent) may be an air-permeable wire mesh or screen material, a woven mat or sheet material, an apertured metal or polymer sheet material, or any other material that provides suitable process dimensional stability and durability under conditions of use contemplated herein, and a relatively high degree of air permeability in a z-direction combined with a relatively small spacing and sizing of air passageways, such that spun filaments striking the belt will accumulate thereon rather than being blown or drawn through air passageways to any substantial extent, by air moving therethrough in the z-direction. A transparent film or mask printed with, or otherwise reflecting in the negative, opaque portions having defining a desired pattern, arrangement, sizes and shape(s) for desired airflow blocking structures 262, is laid down over the liquid photosensitive resin. The resin is then exposed to light of an appropriate wavelength through the film, such as UV light for a UV-curable resin. This exposure to light causes curing of the resin beneath the transparent portions (e.g., non-printed portions) of the mask. Uncured resin (beneath the opaque portions in the mask) may then be removed from the substrate (e.g., via use of a solvent), leaving behind solid, airflow blocking structures formed of the cured resin formed on the substrate, arranged in the desired pattern and shape(s), for example, the pattern of airflow blocking structures 262 shown in FIG. 12. Other patterns of airflow blocking structures for imparting any desired decorative or functional features to a nonwoven web material can also be formed. Airflow blocking structures 262 form and define airflow blocked regions 264 of forming belt 260, through which z-direction air flow through the belt is blocked. The portions of the substrate belt material 261 on which the resin was left uncured, and from which it was removed, form and define airflow permeable regions 263 of forming belt 260, through which z-direction air flow through the belt is permitted. The resin may be formed and cured on the belt to a depth and in a manner such that airflow blocking structures 262 have a desired z-direction depth, and flat land surfaces 262a generally along an x-y plane. Following formation of the airflow blocking structures, ends of the sheet of substrate belt material with the airflow blocking structures formed thereon may be joined in any suitable manner to form a continuous forming belt 260.

Batt and Web Formation

Figure 15:
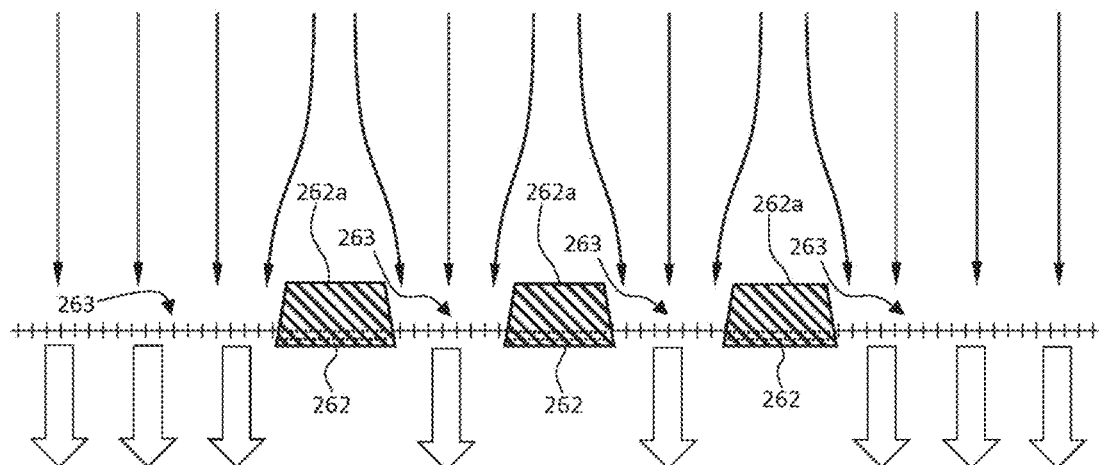
FIG. 15 is an expanded schematic view of the cross section of FIG. 14, illustrating the general directions of filament travel to, and air flow through, the forming belt when in operation.
Figure 16:
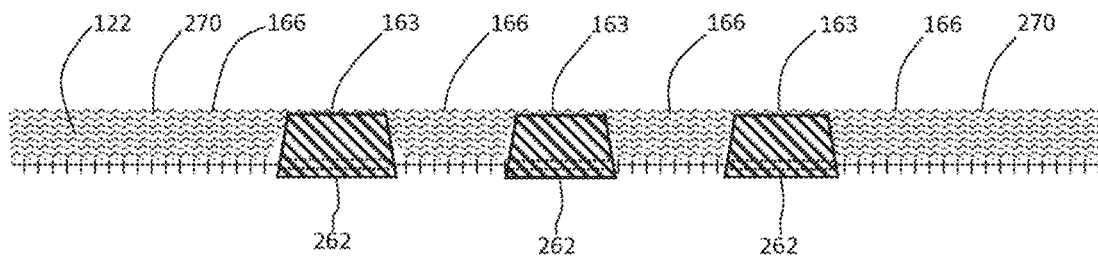
FIG. 16 is a schematic lateral cross section view of filament accumulation on the portion of the forming belt as shown in FIG. 15, following deposition of filaments thereon to form a batt.
Figure 17:
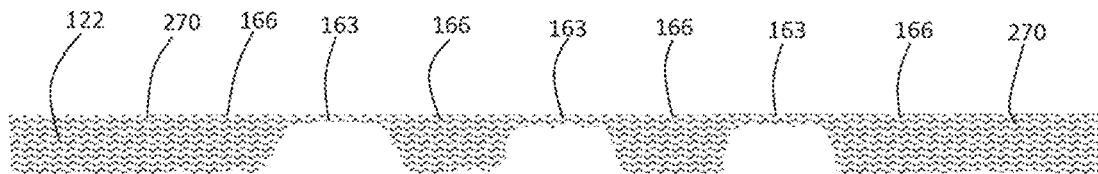
FIG. 17 is a schematic lateral cross section view of a batt of filaments formed on the portion of a forming belt shown in FIG. 16, following removal therefrom.

FIGS. 15-17 illustrate the manner in which spun filaments may be accumulated on forming belt 260, with the location and depth of filament accumulation being affected by the arrangement and depth of airflow blocking structures 262 on the forming belt. Because the filaments are entrained in attenuating air being driven downward and drawn through the belt in the z-direction by the forming vacuum system 555 (see FIG. 11) they follow the air as it finds its way around and past the blocking structures 262 and are deposited predominately on/over airflow permeable regions 263 of the forming belt. Accordingly, the filaments accumulate to a greater depth and/or filament area density and weight over the airflow permeable regions 263, to form built-up regions 166 of a batt 270 of filaments accumulated on the belt. As previously noted, the extent of filament accumulation on the forming belt, generally, may be controlled by controlling the belt cycling speed and the filament spinning rate, or a combination thereof. Turbulence and resulting randomness in the air flow as it approaches the belt, and machine direction movement of the belt, will cause a smaller accumulation of filaments (which are generally continuous as spun) crossing over and thereby accumulating to a lesser extent over the land surfaces 262a of the airflow blocking structures 262, forming attenuated regions 163 in the batt 270 of accumulated filaments. This effect is schematically illustrated in FIG. 9, which depicts a relatively small accumulation of filaments 122 crossing through channel portions 164, as they may be formed by appropriately configured airflow blocking structures, and also in FIG. 16. The relative distribution of filaments between attenuated regions 163 and built-up regions 166, and resulting relative basis weights therebetween, may be adjusted at least in part by regulating the air flow rate drawn through the forming belt 260 by the forming vacuum system 555. Generally, a relatively lesser number of filaments will accumulate over the land surfaces 262a of the airflow blocking structures 262, and a relatively greater number of filaments will accumulate over the airflow permeable regions 263, with a relatively greater air flow rate into vacuum system 555—and vice versa. Alternatively or in combination with regulation of air flow rate drawn by the forming vacuum system 555, the relative distribution of filaments between the attenuated regions 163 and the built-up regions 166 may be controlled by selection of the substrate forming belt material 261. Generally, a relatively lesser number of filaments will accumulate over the land surfaces 262a of the airflow blocking structures 262, and a relatively greater number of filaments will accumulate over the airflow permeable regions 263, with a relatively greater air permeability of the substrate belt material 261 and consequently, of the airflow permeable regions 263, of the forming belt 260—and vice versa.

Following compaction between compaction rollers 571, 572 (shown in FIG. 11) and subsequent removal from the forming belt, as illustrated in FIG. 17 the batt 270 will have a structure with built-up regions 166 and attenuated regions 163 substantially corresponding to the arrangement of airflow blocking structures on the forming belt. As noted, filaments and/or portions thereof occupying the attenuated regions 163 may be somewhat plastically deformed (e.g., flattened) as a result of compaction between compaction roller 570 and the land surfaces 262a of the airflow blocking structures 262. Correspondingly, filaments and/or portions thereof occupying the built-up regions 166 generally will not be deformed by compaction or may be deformed to a substantially lesser extent, because during compaction they are disposed in the spaces between the airflow blocking structures and thus are not so closely compressed as the batt passes through compaction nip 270a.

Using a forming belt 260 and process as described above, a difference between the fiber and/or filament area density, and/or the basis weight, of the batt, of the built-up regions versus the attenuated regions can be achieved to a level of 2:1, 3:1 or even 4:1 or greater.

From the description above and the figures, it will also be appreciated that a formed nonwoven web material manufactured according to the process described will exhibit "sidedness," meaning a difference between features of the surface that will be comprised by a wearer-facing surface of a topsheet, and features of the opposing surface that will be comprised by an absorbent-facing surface of the topsheet. Referring to FIGS. 16 and 17, for example, it will be appreciated that the surface of the batt (and subsequent nonwoven web material) formed by filaments that reached the forming belt first in time (first-formed surface) will exhibit topographic features and/or texture, according to the ordered arrangement, that have substantially greater z-direction depth, than any topographic features and/or texture of the opposing surface, i.e., the surface formed by filaments that reached the forming belt last in time (last-formed surface), prior to compaction of the batt. As a result of such sidedness, visual discernibility of zones reflecting an ordered arrangement may be substantially greater on the first-formed surface (which may form the wearer-facing surface of a topsheet). Consequently, the visual impact of the zones and of the resulting topographic/textural features may be more dramatic on the first-formed surface, than on the opposing last-formed surface. In conjunction therewith and with the method of manufacture, those portions of filaments occupying the attenuated regions will generally be closer in the z-direction, to the last-formed surface.

Although a melt spinning/spunbond process and deposition of filaments onto a forming belt is described above, it is also contemplated that other filaments and/or fiber deposition and basis weight distribution techniques and processes may be employed, including so-called co-forming processes described in, for example, U.S. Pat. Nos. 9,944,047; 8,017,534; 5,508,102; 4,100,324; and US 2003/0211802; PCT application publication number WO 2018/064595 A1; and US 2018/002848; US 2017/002486; US 2017/000695; US 2017/0342617; US 2016/0355950; and other techniques such as spunlace formation techniques in which a web formed of airlaid fibers (including natural and/or synthetic/polymeric fibers) have fiber location and distribution within the web material modified by controlled and ordered hydroenhancement/hydroentanglement, to form the ordered arrangement of channel portions, hinge portions, built-up and attenuated regions contemplated herein, and resulting ordered arrangements of features, which may be formed so as to be visually discernible.

Balancing Filament Surface Hydrophobicity and Hydrophilicity

As discussed above, filaments to be spun and accumulated to form the nonwoven web may be extruded from a polymer resin or blend of resins selected for various properties they impart to the filaments including tensile strength, tactile softness (affected by properties such as filament stiffness and surface coefficient of friction), hydrophilicity/hydrophobicity, etc., as well as cost. Additionally, the filaments and/or the formed nonwoven web may receive post-formation treatments applied, such as, for example, application of a surfactant to one or more surfaces.

Depending on the polymeric resin(s) used to spin them, surfaces of individual synthetic fibers or filaments may be slightly to highly hydrophilic, slightly to highly hydrophobic, or neutral, affecting the extent of the fibers'/filaments' tendency, or lack thereof, to attract aqueous fluid and draw it along their surfaces. Within a nonwoven web structure that includes numerous fiber/filament surfaces of varying geometry and/or spatial orientation, the extent of hydrophilicity or hydrophobicity of individual fiber surfaces in the aggregate, together with the extent of fiber consolidation that affects the porosity of the structure, will on a macroscopic level impart overall hydrophilicity, hydrophobicity, wicking, and absorption properties to the web structure. Including fibers or filaments of differing composition in the nonwoven will also have impact. Thus, depending upon the type(s) of constituent fibers or filaments used to form it, the macroscopic surface of a nonwoven web may be neutral, slightly to highly hydrophilic or slightly to highly hydrophobic, affecting the extent of its tendency to attract aqueous fluid, conduct ("wick") the fluid through interstices or pores within the fibrous structure, and retain (i.e., absorb) the fluid within the structure.

The extent to which a nonwoven as an overall structure tends to repel, or alternatively to attract, wick and/or retain aqueous fluid may be manipulated through selection of fiber/filament material composition, fiber spinning/processing, web structuring and fiber consolidation, and post formation treatment. Additives may be blended with polymer resins, which will modify the extent of hydrophilicity or hydrophobicity of the surfaces of the fibers or filaments spun from the resins. Following spinning of the fibers or filaments and/or formation of the nonwoven web material, hydrophobizing or hydrophilizing agents may be applied to the surfaces of the fibers or filaments and/or nonwoven.

In designing a nonwoven suitable for use as topsheet material for a wearable absorbent article such as a feminine hygiene pad, the manufacturer may face an inherent conflict. On one hand, the material must be sufficiently hydrophilic and have suitable porosity to accept a discharge of fluid such as urine or menses, and wick it in the z-direction so as to pass it through to an absorbent structure disposed beneath the topsheet. A topsheet that does not sufficiently and rapidly accept discharged fluid and move it in the z-direction down to the absorbent structure beneath increases the risk that the fluid will escape the article and soil underwear, outer garments, bedclothes, etc. On the other hand, if the material is hydrophilic and has a porosity level conducive to effective wicking, it may also be prone to incomplete drainage and/or rewetting, i.e., retaining and holding some portion of the discharged fluid, or reacquiring fluid from the absorbent structure. A topsheet that retains discharged fluid or is prone to rewetting is generally not preferred by users/wearers because it tends to feel unpleasantly wet and can promote overhydration of the skin.

It has been learned that a balance of hydrophobic and hydrophilic filament/nonwoven properties may be achieved within the structured topsheet material described herein, between suitable fluid acquisition rate and suitable low rewet tendency. Through prototyping and consumer testing it has been learned that consumer-users of feminine hygiene pads, for example, most prefer a pad configured with a topsheet that exhibits a maximum Rewet (expressed in grams of fluid) of no greater than 0.50 g, more preferably no greater than 0.45 g., and even more preferably no greater than 0.40 g, when the pad is tested using the Rewet measurement method set forth herein. Rewet as measured for purposes herein is a reflection of the absorbent structure/topsheet combination's tendency (or lack thereof) to pass absorbed fluid back into the topsheet under particular conditions, which reflect the topsheet's tendency to undesirably feel wet to the user under use conditions. Using the materials and topsheet structuring methods described herein, for example, a combination of polymeric spinning resin (e.g., polyolefin, e.g., polypropylene and/or polyethylene) whose inherent hydrophobicity may be supplemented by inclusion of a suitable hydrophobizing melt additive, rewet tendencies can be reduced, even down to substantially little or no rewet tendency.

However, a topsheet formed of a nonwoven of spun filaments with very low rewet tendency will necessarily be quite hydrophobic and/or of low porosity—and therefore, resistant to fluid penetration and movement in the z-direction therethrough. Upon contacting the wearer-facing surface of such a topsheet, fluid will tend to roll over the surface along an x-y direction without penetrating it, increasing the risk that the fluid will remain in contact with the user's skin and create an insecure wet feeling, and the risk that it will escape the pad and soil surrounding underwear, outer garments, etc. Accordingly, while a low rewet tendency for a topsheet may be desirable in theory, it must be balanced with other features that enable the topsheet to receive and move the fluid in a z-direction.

An ordered arrangement of zones including attenuated regions and built-up regions as described herein, which may be combined with application of a surfactant as described herein, provides a way of striking this balance. The attenuated regions, being relatively sparsely populated by filaments, provide pathways for fluid to move in a z-direction through the topsheet. Additionally, application of a surfactant to the absorbent-facing side of the topsheet web (where the absorbent-facing side is the side of the web that faced away from the forming belt 260 during formation of the web) results in a predominant number of filaments in the attenuated regions having surfactant on their surfaces and thereby being rendered hydrophilic, while filaments on the wearer-facing side of the built-up regions 166 remain relatively hydrophobic. On a macroscopic level, the attenuated regions exhibit behavior akin to small drains in the topsheet through which fluid will be drawn in a z-direction down through the topsheet. The surfactant may be selected and applied at a chosen coverage quantity to adjust the rapidity with which fluid will move through the topsheet.

However, just as excessive hydrophobicity can frustrate fluid acceptance and movement within the topsheet, excessive hydrophilicity imparted by, e.g., excessive application of surfactant, can impart unacceptable rewet tendency. Through prototyping and consumer testing it has been learned that consumer-users of feminine hygiene pads most prefer a pad configured with an absorbent structure and a topsheet that exhibits an Acquisition Time (expressed in seconds) of no greater than 25 s, when the pad is tested using the Acquisition Time measurement method set forth herein. Acquisition Time as measured for purposes herein is a reflection of the absorbent structure/topsheet combination's tendency (or lack thereof) to receive and transfer fluid in a z-direction to the absorbent structure under particular conditions. Rapid acquisition is preferable, but cannot be reduced freely without adversely increasing rewet tendency of the topsheet. Using the materials and topsheet structuring methods described herein, for example, a combination of fibers having inherent and/or supplemented hydrophobicity, Acquisition Time can be reduced. It has been learned that consumer users most prefer a combination of absorbent structure and topsheet in which a balance has been struck between an Acquisition Time no greater than 25 s, more preferably no greater than 20 s, and even more preferably no greater that 15 s and Rewet no greater than 0.50 g.

Data collected through experimentation and consumer testing suggests that lower limits on these ranges may exist, within the context of the materials and structures described herein. Through experimentation the lowest Rewet level achieved with an Acquisition Time no greater than 15 s was about 0.24 g. The lowest Acquisition Time with a Rewet no greater than 0.50 g was about 4 s. Without intending to be bound by theory, however, it is believed that these combined values may be reduced further with suitable experimentation with materials and structures as described herein. The operative combination of maximum Rewet and maximum Acquisition Time is believed to be an important discovery of consumer preference for and consumer satisfaction with a pad with a functionally structured, visually appealing topsheet as described herein.

Experimental Examples

Figure 28:
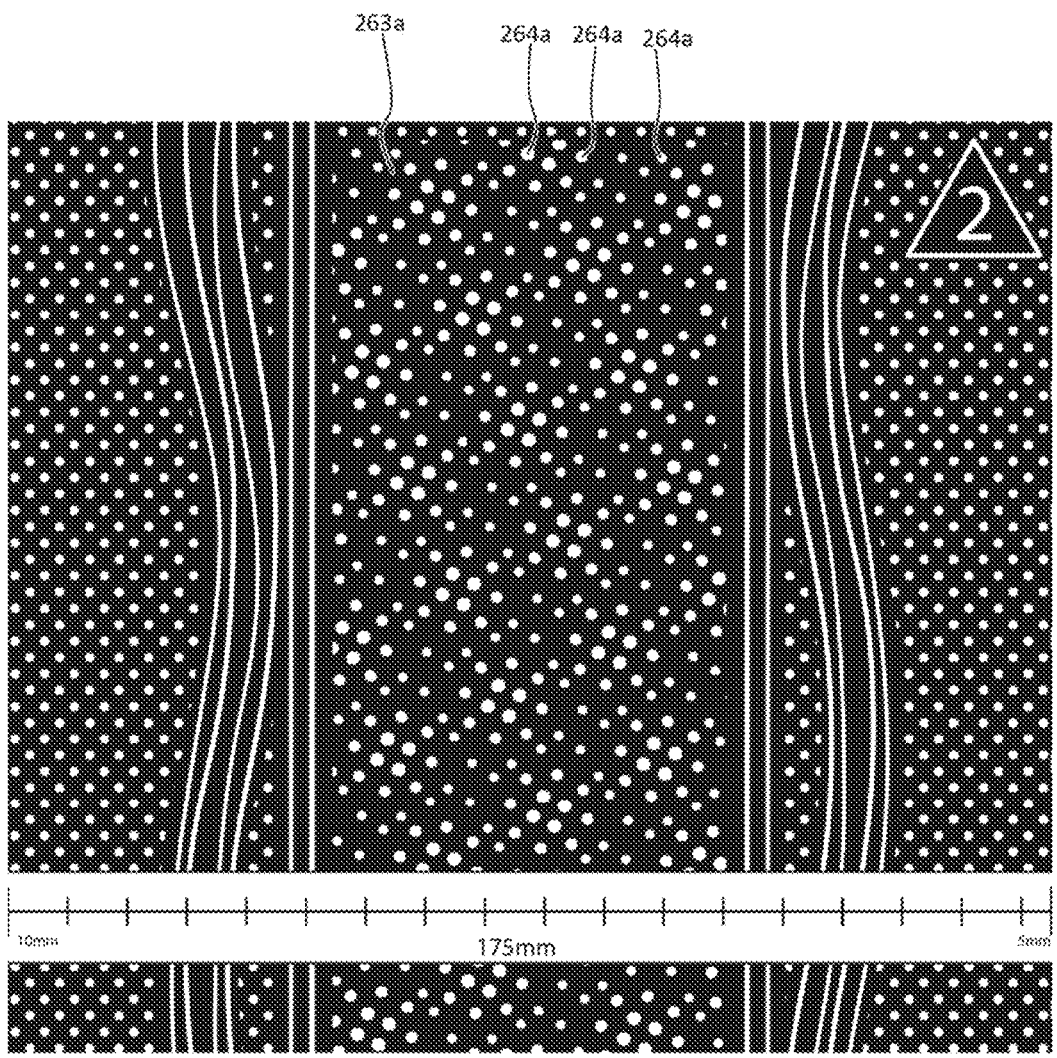
FIG. 28 is an image of portion of a mask used to produce a forming belt used to make the nonwoven web material sample depicted in FIG. 26B, with a superimposed dimension scale indicator.

Prototype/sample feminine hygiene pads were manufactured having the following components:

Each pad had a topsheet cut from a nonwoven web material formed of side-by-side bicomponent spunbond filaments with a 70:30 component weight ratio of two differing polypropylene resin compositions. Approximately 1 percent by weight titanium dioxide was blended into the resin compositions. Erucamide was added to the resin compositions for the differing samples, in quantities shown in Table 1 below. The differing polypropylene components exhibited differing contraction rates on cooling, resulted in helically crimped or curled spun filaments. Spinning and attenuating equipment was adjusted to impart the spun filaments with an average diameter of approximately 18 μm. The spun filaments were deposited onto a moving forming belt formed with airflow blocking structures of shapes and sizes reflected by the image of the mask depicted in FIG. 28, to result in a nonwoven having the ordered arrangement of zones depicted in FIG. 26B. Filament spinning and deposition rates were controlled to impart the nonwoven with an average basis weight of approximately 32 gsm. Following filament spinning and deposition on the forming belt, the batt was compacted in a nip as schematically depicted as element 570a in FIG. 11, wherein the compaction roller was heated to approximately 140 C. Following compaction and removal from the forming belt the batt was calender bonded in a nip between patterned and anvil bonding rollers heated to approximately 140-145 C. The patterned bonding roller was configured to impart a regular pattern of regularly-spaced circular bonds each having a diameter of approximately 0.8 mm, and suitable numerical density per unit surface area to result in a total bonded area for the finished web product of approximately 10 percent of the total surface area on one side.

The topsheet was overlaid directly onto a secondary topsheet/acquisition/distribution layer having a basis weight of 55 gsm and formed of carded spunlace staple fibers consisting of a blend of 40 percent by weight viscose fibers of 1.7 decitex, 40 percent by weight polyethylene/polypropylene bicomponent fibers of 1.7 decitex, and 20 percent by weight PET fibers of 4.4 decitex.

The secondary topsheet directly overlaid an additional absorbent structure layer formed of an blend of cellulose fibers, bicomponent polymer staple fibers and particles of absorbent gelling material, airlaid to a basis weight of 160 gsm, an absorbent structure composition appearing in ALWAYS ULTRA feminine hygiene pads currently marketed by The Procter & Gamble Company in Western Europe.

The additional absorbent structure layer directly overlaid a backsheet formed of liquid impervious polyethylene film, which was bonded about its perimeter via adhesive to the topsheet, whereby the topsheet and the backsheet formed an envelope containing the absorbent structure including the secondary topsheet and the additional absorbent structure layer.

For purposes of studying the effects and interactions between an example of a melt additive and an example of a surfactant and consumer preferences, the polypropylene resins used to spin the topsheet filaments, for varying sample, had varying levels of erucamide added and blended into the melted resin as melt additive prior to spinning. The finished topsheet materials for the varying samples had the indicated varying levels of surfactant applied to the outward/core-facing surface, via inkjet printing equipment. The surfactant applied was STANTEX S6887, obtained via a U.S. sales office representing Pulcra Chemicals/Fashion Chemicals GmbH & Co., Geretsried, Germany. The amount of melt additive included and the amount of surfactant applied for various samples is set forth in Table 1 below.

For each sample, the Acquisition Time and the Rewet were measured using the Acquisition Time and Rewet Measurement methods set forth below. From the data, it can be seen that Acquisition Time and Rewet in combination may be manipulated by manipulation of the amounts of melt additive added and surfactant applied. As noted, it has been concluded from consumer testing that a pad having a combination of Rewet of no greater than 0.50 g, more preferably no greater than 0.45 g, and even more preferably no greater than 0.40 g, and an Acquisition Time of no greater than 25 seconds, more preferably no greater than 20 seconds, and even more preferably no greater than 15 seconds, is acceptable or preferred by consumers, over a pad that falls outside these parameters. Generally, the data reflected that, while a relatively shorter Acquisition Time was preferred, a tradeoff was a relatively greater Rewet, which was not preferred. Manipulation of features described herein, including a topsheet formed as described herein, enabled a suitable balance of acceptable levels of these fluid handling characteristics.

nonwoven web material. It is based on analysis of a 3D x-ray sample image obtained on a micro-CT instrument (a suitable instrument is the Scanco μCT 50 available from Scanco Medical AG, Switzerland, or equivalent). The micro-CT instrument is a cone beam microtomograph with a shielded cabinet. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. A 3D image of the sample is generated by collecting several individual projection images of the sample as it is rotated, which are then reconstructed into a single 3D image. The instrument is interfaced with a computer running software to control the image acquisition and save the raw data. The 3D image is then analyzed using image analysis software (a suitable image analysis software is MATLAB available from The Mathworks, Inc., Natick, MA, or equivalent) to measure the basis weight, thickness and volumetric density intensive properties of regions within the sample.

Sample Preparation

To obtain a sample for measurement, lay a single layer of the formed nonwoven web material of interest out flat on a work surface, and die cut therefrom a circular piece with a diameter of 30 mm.

TABLE 1

| Sample # | Melt additive % by weight | Surfactant level (gsm) | Acquisition Time (seconds) | Rewet (g) | Consumer acceptable/ preferred (Yes or No) |
| --- | --- | --- | --- | --- | --- |
| 17 | 0.0% | 1.00 | 5.5 | 0.644 | N |
| 20 | 0.5% | 1.00 | 5.5 | 0.556 | N |
| 16 | 0.0% | 0.35 | 6.2 | 0.593 | N |
| 26 | 1.5% | 0.85 | 6.2 | 0.416 | Y |
| 5A | 1.5% | 1.00 | 6.7 | 0.464 | Y |
| 19 | 0.5% | 0.35 | 7.2 | 0.463 | Y |
| 25 | 1.5% | 0.30 | 8.3 | 0.364 | Y |
| 18 | 0.5% | 0.15 | 8.7 | 0.386 | Y |
| 2A | 1.5% | 0.35 | 8.8 | 0.424 | Y |
| 15 | 0.0% | 0.15 | 9.0 | 0.548 | N |
| 1 | 1.5% | 0.15 | 11.2 | 0.347 | Y |
| 24 | 1.5% | 0.13 | 13.7 | 0.288 | Y |
| 30 | 1.5% | 0.10 | 25.5 | 0.269 | N |
| 31 | 1.5% | 0.05 | 48.0 | 0.183 | N |

Test/Measurement Methods

Localized Basis Weight

Localized basis weight of a region of a formed nonwoven web material may be determined by several available techniques, but a simple representative technique when the region is suitably large involves cutting a sample piece of the web representing the selected region from the overall area of the material. The sample piece is then weighed and divided by its area to yield the localized basis weight of the nonwoven fabric in, units of grams per square meter (gsm). Results are reported as a mean of 2 samples per selected region.

Micro-CT Intensive Property Measurement Method

The micro-CT intensive property measurement method measures the basis weight, thickness and volumetric density values within visually discernable regions of a sample of If the material is a layer of an absorbent article, for example a topsheet, backsheet nonwoven, acquisition layer, distribution layer, or other component layer; tape the absorbent article to a rigid flat surface in a planar configuration. Carefully separate the layer from the absorbent article. A scalpel and/or cryogenic spray (to substantially deactivate adhesives) (such as Cyto-Freeze, Control Company, Houston TX) may be used as necessary to remove a substrate layer from additional underlying layers, if necessary, to avoid any longitudinal and lateral extension of the material. Once the substrate layer has been removed from the article proceed with die cutting the sample as described above.

A sample may be cut from any location containing the zone to be analyzed. Within a zone, regions to be analyzed are ones associated with an ordered arrangement as defined herein. The zone includes a least two regions. A zone and regions thereof may be visually discernible or otherwise identifiable due to changes in fiber and/or filament area density, basis weight, opacity, caliper/thickness or z-direction elevation. Regions within different samples taken from the same substrate material may be analyzed and compared to each other. Care should be taken to avoid folds, wrinkles or tears when selecting a location on the formed nonwoven web material of interest for sampling.

Image Acquisition

Set up and calibrate the micro-CT instrument according to the manufacturer's specifications. Place the sample into the appropriate holder, between two rings of low density material, which have an inner diameter of 25 mm. This will allow the central portion of the sample to lay horizontal and be scanned without having any other materials directly adjacent to its upper and lower surfaces. Measurements should be taken in this region. The 3D image field of view is approximately 35 mm on each side in the x-y plane with a resolution of approximately 5000 by 5000 pixels, and with a sufficient number of 7 micron thick slices collected to fully include the z-direction of the sample. The reconstructed 3D image resolution contains isotropic voxels of 7 microns. Images are acquired with the source at 45 kVp and 133 µA with no additional low energy filter. These current and voltage settings may be optimized to produce the maximum contrast in the projection data with sufficient x-ray penetration through the sample, but once optimized held constant for all substantially similar samples. A total of 1500 projections images are obtained with an integration time of 1000 ms and 3 averages. The projection images are reconstructed into the 3D image, and saved in 16-bit RAW format to preserve the full detector output signal for analysis.

Image Processing

Load the 3D image into the image analysis software. Threshold the 3D image at a value which separates, and removes, the background signal due to air, but maintains the signal from the sample fibers within the substrate.

Three 2D intensive property images are generated from the threshold 3D image. The first is the Basis Weight Image. To generate this image, the value for each voxel in an x-y plane slice is summed with all of its corresponding voxel values in the other z-direction slices containing signal from the sample. This creates a 2D image where each pixel now has a value equal to the cumulative signal through the entire sample.

In order to convert the raw data values in the Basis Weight Image into real values a basis weight calibration curve is generated. Obtain a substrate that is of substantially similar composition as the sample being analyzed and has a uniform basis weight. Follow the procedures described above to obtain at least ten replicate samples of the calibration curve substrate. Accurately measure the basis weight, by taking the mass to the nearest 0.0001 g and dividing by the sample area and converting to grams per square meter (gsm), of each of the single layer calibration samples and calculate the average to the nearest 0.01 gsm. Following the procedures described above, acquire a micro-CT image of a single layer of the calibration sample substrate. Following the procedure described above, process the micro-CT image, and generate a Basis Weight Image containing raw data values. The real basis weight value for this sample is the average basis weight value measured on the calibration samples. Next, stack two layers of the calibration substrate samples on top of each other, and acquire a micro-CT image of the two layers of calibration substrate. Generate a basis weight raw data image of both layers together, whose real basis weight value is equal to twice the average basis weight value measured on the calibration samples. Repeat this procedure of stacking single layers of the calibration substrate, acquiring a micro-CT image of all of the layers, generating a raw data basis weight image of all of the layers, the real basis weight value of which is equal to the number of layers times the average basis weight value measured on the calibration samples. A total of at least four different basis weight calibration images are obtained. The basis weight values of the calibration samples must include values above and below the basis weight values of the original sample being analyzed to ensure an accurate calibration. The calibration curve is generated by performing a linear regression on the raw data versus the real basis weight values for the four calibration samples. This linear regression must have an R2 value of at least 0.95, if not repeat the entire calibration procedure. This calibration curve is now used to convert the raw data values into real basis weights.

The second intensive property 2D image is the Thickness Image. To generate this image the upper and lower surfaces of the sample are identified, and the distance between these surfaces is calculated giving the sample thickness. The upper surface of the sample is identified by starting at the uppermost z-direction slice and evaluating each slice going through the sample to locate the z-direction voxel for all pixel positions in the x-y plane where sample signal was first detected. The same procedure is followed for identifying the lower surface of the sample, except the z-direction voxels located are all the positions in the x-y plane where sample signal was last detected. Once the upper and lower surfaces have been identified they are smoothed with a 15×15 median filter to remove signal from stray fibers. The 2D Thickness Image is then generated by counting the number of voxels that exist between the upper and lower surfaces for each of the pixel positions in the x-y plane. This raw thickness value is then converted to actual distance, in microns, by multiplying the voxel count by the 7 µm slice thickness resolution.

The third intensive property 2D image is the Volumetric Density Image. To generate this image divide each x-y plane pixel value in the Basis Weight Image, in units of gsm, by the corresponding pixel in the Thickness Image, in units of microns. The units of the Volumetric Density Image are grams per cubic centimeter (g/cc).

Micro-CT Basis Weight, Thickness and Volumetric Density Intensive Properties

Begin by identifying the region to be analyzed. A region to be analyzed is one associated with a zone. The zone includes a least two regions. A zone and regions thereof, may be visually discernible or otherwise identifiable due to changes in fiber and/or filament area density, basis weight, opacity, caliper/thickness or z-direction elevation. Next, identify the boundary of the region to be analyzed. The boundary of a region is identified by visual discernment of differences in intensive properties when compared to other regions within the sample. For example, a region boundary may be identified based by visually discerning a thickness/caliper difference when compared to another region in the sample. Any of the intensive properties may be used to discern region boundaries on either the physical sample itself of any of the micro-CT intensive property images. Once the boundary of the region has been identified, draw an oval or circular "region of interest" (ROI) within the interior of the region. The ROI should have an area of at least 0.1 mm², and be selected to measure an area with intensive property values representative of the identified region. From each of the three intensive property images calculate the average basis weight, thickness and volumetric density within the ROI. Record these values as the region's basis weight to the nearest 0.01 gsm, thickness to the nearest 0.1 micron and volumetric density to the nearest 0.0001 g/cc.

Acquisition Time and Rewet Measurement

Artificial Menstrual Fluid (AMF) Preparation

The Artificial Menstrual Fluid (AMF) is composed of a mixture of defibrinated sheep blood, a phosphate buffered saline solution and a mucous component. The AMF is prepared such that it has a viscosity between 7.15 to 8.65 centistokes at 23° C.

Viscosity on the AMF is performed using a low viscosity rotary viscometer (a suitable instrument is the Cannon LV-2020 Rotary Viscometer with UL adapter, Cannon Instrument Co., State College, PA, or equivalent). The appropriate size spindle for the viscosity range is selected, and instrument is operated and calibrated as per the manufacturer. Measurements are taken at 23° C.±1° C. and at 60 rpm. Results are reported to the nearest 0.01 centistokes.

Reagents needed for the AMF preparation include: defibrinated sheep blood with a packed cell volume of 38% or greater (collected under sterile conditions, available from Cleveland Scientific, Inc., Bath, Ohio, or equivalent), gastric mucin with a viscosity target of 3-4 centistokes when prepared as a 2% aqueous solution (crude form, available from Sterilized American Laboratories, Inc., Omaha, NE, or equivalent), 10% v/v lactic acid aqueous solution, 10% w/v potassium hydroxide aqueous solution, sodium phosphate dibasic anhydrous (reagent grade), sodium chloride (reagent grade), sodium phosphate monobasic monohydrate (reagent grade) and distilled water, each available from VWR International or an equivalent source.

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add distilled water to volume. Mix thoroughly. To prepare the phosphate buffered saline solution, add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. To determine the amount of gastric mucin needed to achieve AMF within the target viscosity range (7.15-8.65 centistokes at 23° C.) prepare 3 batches of AMF with varying amounts of gastric mucin in the mucous component, and then interpolate the exact amount needed from a concentration versus viscosity curve with a least squares linear fit through the three points. A successful range of gastric mucin is usually between 38 to 50 grams.

To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5° C. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range. After the 2.5 hours has elapsed, remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1° C.

Allow the temperature of the sheep blood and mucous component to come to 23° C.±1° C. Using a 500 mL graduated cylinder, measure the volume of the entire batch of the previously prepared mucous component and add it to a 1200 mL beaker. Add an equal volume of sheep blood to the beaker and mix thoroughly. Using the viscosity method previously described, ensure the viscosity of the AMF is between 7.15-8.65 centistokes. If not the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1° C. Any unused portion is discarded after testing is complete.

Measurement

Acquisition Time is measured for an absorbent article loaded with Artificial Menstrual Fluid (AMF), prepared as described herein.

A known volume of AMF is introduced three times, each successive dose starting two minutes after the previous dose has absorbed. The time required for each dose to be absorbed by the article is recorded. Subsequent to the acquisition test, a rewet method is performed to determine the mass of fluid expressed from the article under pressure.

Sample feminine hygiene pads are conditioned at 23° C.±2° C. and 50%±2% relative humidity for 2 hours prior to testing, and all testing is performed under these conditions.

The confining weight used for the rewet test has a flat level base with a contact surface that is 64±1 mm wide by 83±1 mm long and a mass of 2268±2 grams (5 pounds). This weight provides a confining pressure of 4.1 kPa (0.60 psi) on the test article. The rewet substrate is two sheets of filter paper with dimensions 4 inch by 4 inch. A suitable filter paper is Ahlstrom Grade 989 (available from Ahlstrom-Munksjo North America LLC, Alpharetta, GA) or equivalent.

Perform the Acquisition Time measurement as follows. Remove the sample from its wrapper. If folded, gently unfold and smooth out any wrinkles. Place the sample flat on a horizontal planar work surface, with the topsheet facing upward. Position the tip of a mechanical pipette about 1 cm above the center (intersection of longitudinal and lateral axes) of the article's absorbent structure, and accurately pipette 1.00 ml±0.05 ml of AMF onto the surface. The fluid is dispensed without splashing, within a period of 2 seconds.

As soon as the fluid makes contact with the test sample, start a timer accurate to 0.01 seconds. After the fluid has been acquired (no pool of fluid left on the surface), stop the timer and record the acquisition time to the nearest 0.01 second. Wait 2 minutes. In a similar manner, respective second and third doses of AMF are applied to the test sample, and the acquisition times are recorded to the nearest 0.01 second. Proceed with the Rewet test 2 minutes after the third dose has been acquired.

Perform the Rewet part of the test as follows. Measure the dry mass of two filter papers together to the nearest 0.0001 grams, and record as MassDry. Gently place the dry filter papers over the center (intersection of longitudinal and lateral axes) of the sample's absorbent structure, with the filter papers themselves also centered about such point. Gently place the base of the confining weight over such center, positioning the length (long side) of the weight parallel to the longitudinal direction of the sample. Immediately upon placement of the weight to rest over the sample and filter papers, start a timer accurate to 0.01 seconds. After 30 seconds, carefully remove the weight. Measure the mass of the filter papers to the nearest 0.0001 grams and record as MassWet. Calculate Rewet as the difference between MassWet and MassDry for the filter papers and record as Rewet to the nearest 0.0001 grams.

This entire procedure is repeated on five substantially similar replicate articles. The reported value is the average of the five individual recorded measurements for each Acquisition Time (first, second and third) to the nearest 0.01 second and Rewet to the nearest 0.0001 gram.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. An absorbent article comprising a liquid permeable continuous topsheet, a liquid impermeable backsheet, and an absorbent structure disposed between the continuous topsheet and the backsheet, the continuous topsheet having a lateral axis, a longitudinal axis and an in-use wearer-facing portion having an elongate outer perimeter, the article having a central longitudinally elongate absorbent portion comprising the absorbent structure, flanked by two wing portions opposingly laterally extending from the absorbent portion and being substantially without any portion of the absorbent structure, the continuous topsheet at least partially forming the wing portions;

wherein the continuous topsheet is formed of a section of formed nonwoven web material comprising an accumulation of filaments and having an absorbent-facing side and a wearer-facing side, the wearer-facing side comprising an ordered arrangement of zones, each zone comprising one or more attenuated regions adjacent to one or more built-up regions, wherein the attenuated regions have a first average basis weight and the built-up regions have a second average basis weight, wherein the first average basis weight is less than the second average basis weight, the difference in basis weights corresponding to disposition of the filaments according to the ordered arrangement;

wherein the attenuated regions are comprised by a configuration of channel portions following one or a plurality of paths, the one or plurality of paths being substantially symmetric about the longitudinal axis and predominately circumscribing a discharge locus on the longitudinal axis; and wherein the one or plurality of paths predominately circumscribing the discharge locus are discontinuous.

2. The absorbent article of claim 1 wherein the configuration of the channel portions follows a path proximate to but inside the outer perimeter and at least partially approximately paralleling the perimeter to the inside thereof.

3. The absorbent article of claim 1 wherein the attenuated region(s) and built-up region(s) are visually discernible.

4. The absorbent article of claim 1 wherein the continuous topsheet has a surfactant applied to the absorbent-facing side such that the surfactant is present in a quantity greater on filaments proximate the absorbent-facing side than on filaments proximate the wearer-facing side.

5. The absorbent article of claim 4 wherein a melt additive comprising a compound selected from the group consisting of erucamide, stearamide, oleamide, silicones, petroleum-based hydrocarbons having from about 4 to about 32 carbon atoms, fatty alcohols having from about 12 to about 24 carbon atoms, polysiloxane compounds, fatty acid esters, alkyl ethoxylates, fatty alcohol ethers having from about 12 to about 28 carbon atoms in their fatty chain, lanolin and its derivatives, glyceride derivatives including acetoglycerides and ethoxylated glycerides of C12-C28 fatty acids, fatty amides, and combinations thereof has been added to polymeric resin(s) from which the filaments have been spun.

6. The absorbent article of claim 1 wherein the second average basis weight differs from the first average basis weight by at least a factor of 2.

7. The absorbent article of claim 1 wherein the filaments are spun bicomponent filaments.

8. An absorbent article in the form of feminine hygiene pad or adult incontinence pad, comprising a liquid permeable continuous topsheet, a liquid impermeable backsheet, and an absorbent structure disposed between the continuous topsheet and the backsheet, the article having a central longitudinally elongate absorbent portion comprising the absorbent structure, flanked by two wing portions opposingly laterally extending from the absorbent portion and being substantially without any portion of the absorbent structure, the continuous topsheet at least partially forming the wing portions;

wherein the continuous topsheet is formed of a section of formed nonwoven web material comprising an accumulation of filaments and having an absorbent-facing side and a wearer-facing side, the wearer-facing side comprising an ordered arrangement of zones, each zone comprising one or more attenuated regions adjacent to one or more built-up regions, wherein the attenuated regions have a first average basis weight and the built-up regions have a second average basis weight, wherein the first average basis weight is less than the second average basis weight, the difference in basis weights corresponding to disposition of filaments according to the ordered arrangement;

wherein the attenuated regions are comprised by a hinge portion following a path extending generally longitudinally along one of the wing portions;

wherein the attenuated regions are comprised by a configuration of channel portions following one or a plurality of paths, the one or plurality of paths predominately circumscribing a discharge locus on the longitudinal axis; and wherein the one or plurality of paths predominately circumscribing the discharge locus are discontinuous.

9. The absorbent article of claim 8 wherein the attenuated region(s) and built-up region(s) are visually discernible.

10. The absorbent article of claim 8 wherein the continuous topsheet has a surfactant applied to the absorbent-facing side such that the surfactant is present in a quantity greater on filaments proximate the absorbent-facing side than on filaments proximate the wearer-facing side.

11. The absorbent article of claim 10 wherein a melt additive comprising a compound selected from the group consisting of erucamide, stearamide, oleamide, silicones, petroleum-based hydrocarbons having from about 4 to about 32 carbon atoms, fatty alcohols having from about 12 to about 24 carbon atoms, polysiloxane compounds, fatty acid esters, alkyl ethoxylates, fatty alcohol ethers having from about 12 to about 28 carbon atoms in their fatty chain, lanolin and its derivatives, glyceride derivatives including acetoglycerides and ethoxylated glycerides of C12-C28 fatty acids, fatty amides, and combinations thereof has been added to polymeric resin(s) from which the filaments have been spun.

12. The absorbent article of claim 8 wherein the second average basis weight differs from the first average basis weight by at least a factor of 2.

13. The absorbent article of claim 8 wherein the filaments are spun bicomponent filaments.

14. An absorbent article comprising a liquid permeable continuous topsheet, a liquid impermeable backsheet, and an absorbent structure disposed between the continuous topsheet and the backsheet, the continuous topsheet having lateral axis, a longitudinal axis and an in-use wearer-facing portion having an elongate outer perimeter, the article having a central longitudinally elongate absorbent portion comprising the absorbent structure, flanked by two wing portions opposingly laterally extending from the absorbent portion and being substantially without any portion of the absorbent structure, the continuous topsheet at least partially forming the wing portions;

wherein the continuous topsheet is formed of a section of formed nonwoven web material comprising an accumulation of filaments and having an absorbent-facing surface and a wearer-facing surface, wherein the nonwoven web material has been formed via continuous deposition of spun filaments onto a continuous forming belt having an outer receiving side and an inner side and moving along a machine direction through a working location, to form a batt of filaments deposited on the receiving side of the forming belt, the forming belt comprising an airflow permeable substrate belt and an ordered arrangement of airflow blocking structures disposed on the substrate belt, thereby imparting to the forming belt an ordered arrangement of airflow-permeable regions and airflow-blocked regions coextensive with the airflow blocking structures, the airflow blocking structures extending in a z-direction outward from the substrate belt so has to have a z-direction depth on the receiving side of the forming belt;

wherein before and as they contact the forming belt the filaments are entrained in air flow directed at and through the belt generally along the z-direction, such that the filaments accumulate on the forming belt to a greater second average basis weight over the airflow-permeable regions and to a lesser first average basis weight over the airflow-blocked regions, to create built-up regions of the batt over the airflow-permeable portions and attenuated regions of the batt over the airflow-blocked regions;

wherein the batt is consolidated into a nonwoven web material following its formation on the forming belt;

whereby the attenuated regions form one or more z-direction depressions predominately in the wearer-facing surface of the section of formed nonwoven web material, the one or more depressions defining a configuration of channel portions following one or a plurality of paths, the one or plurality of paths being substantially symmetric about the longitudinal axis and predominately circumscribing a discharge locus on the longitudinal axis; and wherein the one or plurality of paths predominately circumscribing the discharge locus are discontinuous.

15. The absorbent article of claim 14 wherein the consolidation step includes a compaction step wherein the batt is compacted between a compaction roller and land surfaces of the airflow blocking structures, thereby plastically deforming filaments in the attenuated regions.

16. The absorbent article of claim 14 wherein the consolidation step includes a calender bonding step wherein the batt is conveyed through a nip between a pair of calender bonding rollers thereby consolidating and imparting a pattern of bonds to the nonwoven web material.

17. The absorbent article of claim 14 wherein the configuration of the channel portions follows a path proximate to but inside the outer perimeter and at least partially approximately paralleling the perimeter to the inside thereof.

18. The absorbent article of claim 14 wherein the attenuated region(s) and built-up region(s) are visually discernible.

19. The absorbent article of claim 14 wherein the continuous topsheet has a surfactant applied to the absorbent-facing side such that the surfactant is present in a quantity greater on filaments proximate the absorbent-facing side than on filaments proximate the wearer-facing side.

20. The absorbent article of claim 14 wherein the filaments are spun bicomponent filaments.

* * * * *